(12) United States Patent
Lamble et al.

(10) Patent No.: US 9,050,433 B2
(45) Date of Patent: Jun. 9, 2015

(54) DISPENSING DEVICE

(75) Inventors: Ralph George Lamble, Cambridgeshire (GB); Allen John Pearson, Cambridgeshire (GB); Paul Kenneth Rand, Hertfordshire (GB)

(73) Assignee: Glaxo Group Limited, Brentford, Middlesex (GB)

( * ) Notice: Subject to any disclaimer, the term of this patent is extended or adjusted under 35 U.S.C. 154(b) by 888 days.

(21) Appl. No.: 12/745,298

(22) PCT Filed: Nov. 27, 2008

(86) PCT No.: PCT/GB2008/003954
§ 371 (c)(1),
(2), (4) Date: May 28, 2010

(87) PCT Pub. No.: WO2009/068877
PCT Pub. Date: Jun. 4, 2009

(65) Prior Publication Data
US 2010/0308082 A1 Dec. 9, 2010

(30) Foreign Application Priority Data

Nov. 29, 2007 (GB) .................................. 0723418.0
May 29, 2008 (GB) .................................. 0809770.1

(51) Int. Cl.
*B67D 7/84* (2010.01)
*B67D 7/06* (2010.01)
(Continued)

(52) U.S. Cl.
CPC ............. *A61M 15/08* (2013.01); *A61M 15/009* (2013.01); *B05B 1/3436* (2013.01);
(Continued)

(58) Field of Classification Search
USPC ............ 222/162, 160, 556, 183; 128/200.14, 128/200.23, 203.15, 200.17, 200.22, 203.28
See application file for complete search history.

(56) References Cited

U.S. PATENT DOCUMENTS 3,405,843 A * 10/1968 Watson, Jr. ..................... 222/95
4,581,022 A 4/1986 Leonard et al.
(Continued)

FOREIGN PATENT DOCUMENTS

| BY | 5161 C1 | 6/2003 |
|---|---|---|
| DE | 19610456 | 9/1997 |

(Continued)

OTHER PUBLICATIONS

European Search Report dated Apr. 8, 2014 for EP Application No. 13187273.

*Primary Examiner* — Kevin P Shaver
*Assistant Examiner* — Stephanie E Williams
(74) *Attorney, Agent, or Firm* — James P. Riek

(57) ABSTRACT

A device for dispensing a substance having a dispensing outlet, a dispensing member mounted for movement in a dispensing direction U from a first position to a second position, such movement, in use, causing the substance to be dispensed from the dispensing outlet, and an actuator mechanism for moving the dispensing member from the first position to the second position. The actuator mechanism has a first member mounted for movement in a predetermined direction and a second member pivotally mounted on the first member for pivotal movement in a predetermined pivotal sense A. The actuator mechanism is adapted such that movement of the first member in the predetermined direction results in the second member moving therewith and pivoting in the predetermined pivotal sense and the pivotal movement of the second member in the predetermined pivotal sense results in the dispensing member moving from the first position to the second position.

57 Claims, 45 Drawing Sheets

(51) Int. Cl.
*A61M 11/00* (2006.01)
*B05D 7/14* (2006.01)
*A61M 15/08* (2006.01)
*A61M 15/00* (2006.01)
*B05B 1/34* (2006.01)
*B05B 11/00* (2006.01)

(52) U.S. Cl.
CPC ........ *B05B 11/0037* (2013.01); *B05B 11/3004* (2013.01); *B05B 11/3046* (2013.01); *B05B 11/3057* (2013.01); *B05B 11/307* (2013.01); *B05B 11/3074* (2013.01); *A61M 15/0025* (2014.02)

(56) References Cited

U.S. PATENT DOCUMENTS

| | | | |
|---|---|---|---|
| 4,623,337 A | 11/1986 | Maurice | |
| 4,710,178 A | 12/1987 | Henri et al. | |
| 4,771,769 A | 9/1988 | Hegemann et al. | |
| 4,860,738 A | 8/1989 | Hegemann et al. | |
| 4,969,584 A | 11/1990 | Joulia | |
| 5,110,052 A | 5/1992 | Graf et al. | |
| 5,147,087 A | 9/1992 | Fuchs | |
| 5,310,092 A | 5/1994 | Targell | |
| 5,487,489 A | 1/1996 | Weiss et al. | |
| 5,514,365 A | 5/1996 | Mardente et al. | |
| 6,338,422 B1 | 1/2002 | DeJonge | |
| 6,478,196 B2 | 11/2002 | Fuchs | |
| 6,510,847 B1 | 1/2003 | Helgesson et al. | |
| 6,527,144 B2 | 3/2003 | Ritsche et al. | |
| 6,595,205 B2* | 7/2003 | Andersson et al. | 128/200.23 |
| 6,745,760 B2 | 6/2004 | Grychowski et al. | |
| 6,860,411 B2 | 3/2005 | Stradella | |
| 6,948,639 B2 | 9/2005 | Albisetti et al. | |
| 6,964,381 B2 | 11/2005 | Stradella et al. | |
| 7,070,071 B2 | 7/2006 | Pavlu et al. | |
| 7,124,916 B2 | 10/2006 | Groh et al. | |
| 7,175,053 B2 | 2/2007 | Simon et al. | |
| 7,331,944 B2* | 2/2008 | Py et al. | 604/298 |
| 7,353,971 B2 | 4/2008 | Stradella | |
| 7,699,052 B2 | 4/2010 | Schiewe et al. | |
| 8,147,461 B2* | 4/2012 | Bonney et al. | 604/187 |
| 2002/0017294 A1* | 2/2002 | Py | 128/200.23 |
| 2002/0130195 A1 | 9/2002 | Jaeger et al. | |
| 2002/0170928 A1 | 11/2002 | Grychowski et al. | |
| 2003/0136800 A1 | 7/2003 | Brand et al. | |
| 2004/0094146 A1 | 5/2004 | Schiewe et al. | |
| 2005/0006412 A1 | 1/2005 | Albisetti et al. | |
| 2005/0040188 A1 | 2/2005 | Herry et al. | |
| 2005/0077315 A1 | 4/2005 | Pavlu et al. | |
| 2005/0139615 A1 | 6/2005 | Stradella et al. | |
| 2005/0236434 A1 | 10/2005 | Bonney | |
| 2005/0284890 A1 | 12/2005 | Heldt et al. | |
| 2006/0082039 A1 | 4/2006 | Godfrey | |
| 2006/0278225 A1 | 12/2006 | MacMichael et al. | |
| 2007/0095853 A1* | 5/2007 | Bonney et al. | 222/21 |
| 2007/0138207 A1 | 6/2007 | Bonney et al. | |
| 2007/0164049 A1* | 7/2007 | Bonney et al. | 222/162 |
| 2008/0116223 A1 | 5/2008 | Stradella | |
| 2008/0237264 A1 | 10/2008 | Auerbach et al. | |

FOREIGN PATENT DOCUMENTS

| | | |
|---|---|---|
| EA | 007403 B1 | 10/2006 |
| EP | 0925799 | 6/1999 |
| EP | 1132143 | 9/2001 |
| EP | 1197266 | 4/2002 |
| EP | 1974828 | 10/2008 |
| EP | 1237607 | 7/2009 |
| EP | 2222411 B1 | 10/2013 |
| FR | 2637870 A1 | 4/1990 |
| FR | 2671294 | 7/1992 |
| FR | 2 812 826 | 2/2002 |
| FR | 2812826 | 2/2002 |
| FR | 2859464 | 3/2005 |
| FR | 2889691 | 2/2007 |
| FR | 2889692 | 2/2007 |
| GB | 659132 A | 10/1951 |
| GB | 2243880 A | 11/1991 |
| JP | 0457264 U | 5/1992 |
| JP | 04057264 U | 5/1992 |
| JP | 04057264 U | 10/1994 |
| JP | 10179739 A | 7/1998 |
| JP | 2003504280 A | 2/2003 |
| JP | 2003252390 A | 9/2003 |
| JP | 2004516075 A | 6/2004 |
| JP | 2009132396 A | 6/2009 |
| RU | 2067896 C1 | 10/1996 |
| RU | 2093236 C1 | 10/1997 |
| RU | 2093276 C1 | 10/1997 |
| RU | 2097064 C1 | 11/1997 |
| RU | 2277501 C1 | 6/2006 |
| RU | 2287377 C1 | 11/2006 |
| WO | 8910881 A1 | 11/1989 |
| WO | 0103851 A1 | 1/2001 |
| WO | 0220370 A1 | 3/2002 |
| WO | 0249698 A1 | 6/2002 |
| WO | 2005044354 A1 | 5/2005 |
| WO | 2005075103 A1 | 8/2005 |
| WO | 2005087615 A1 | 9/2005 |
| WO | 2007138084 A2 | 12/2007 |
| WO | 2008145714 A2 | 12/2008 |
| WO | 2009147306 A1 | 12/2009 |
| WO | 2009147350 A2 | 12/2009 |
| WO | 2009153512 A1 | 12/2009 |
| WO | 2009153513 A1 | 12/2009 |

* cited by examiner

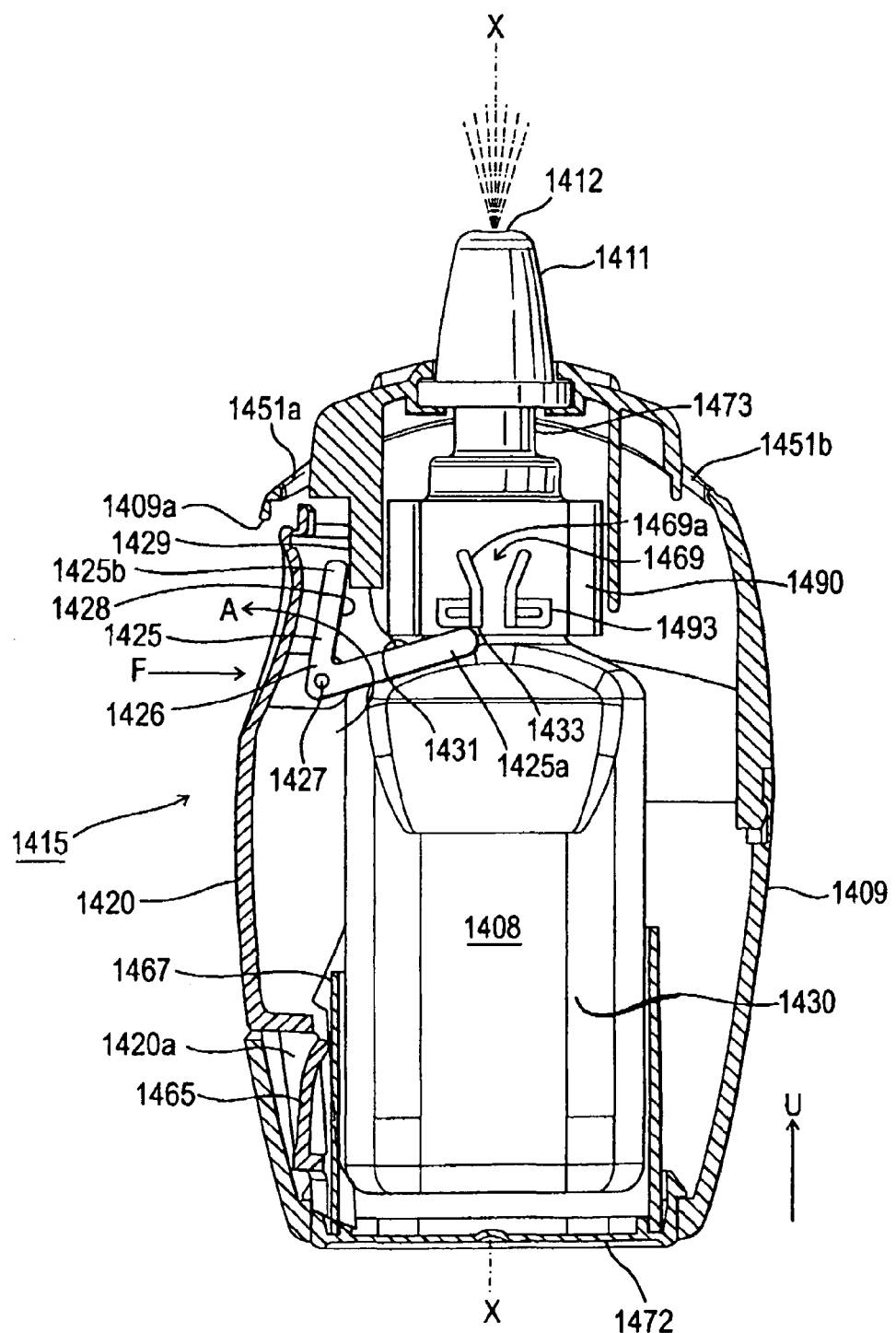

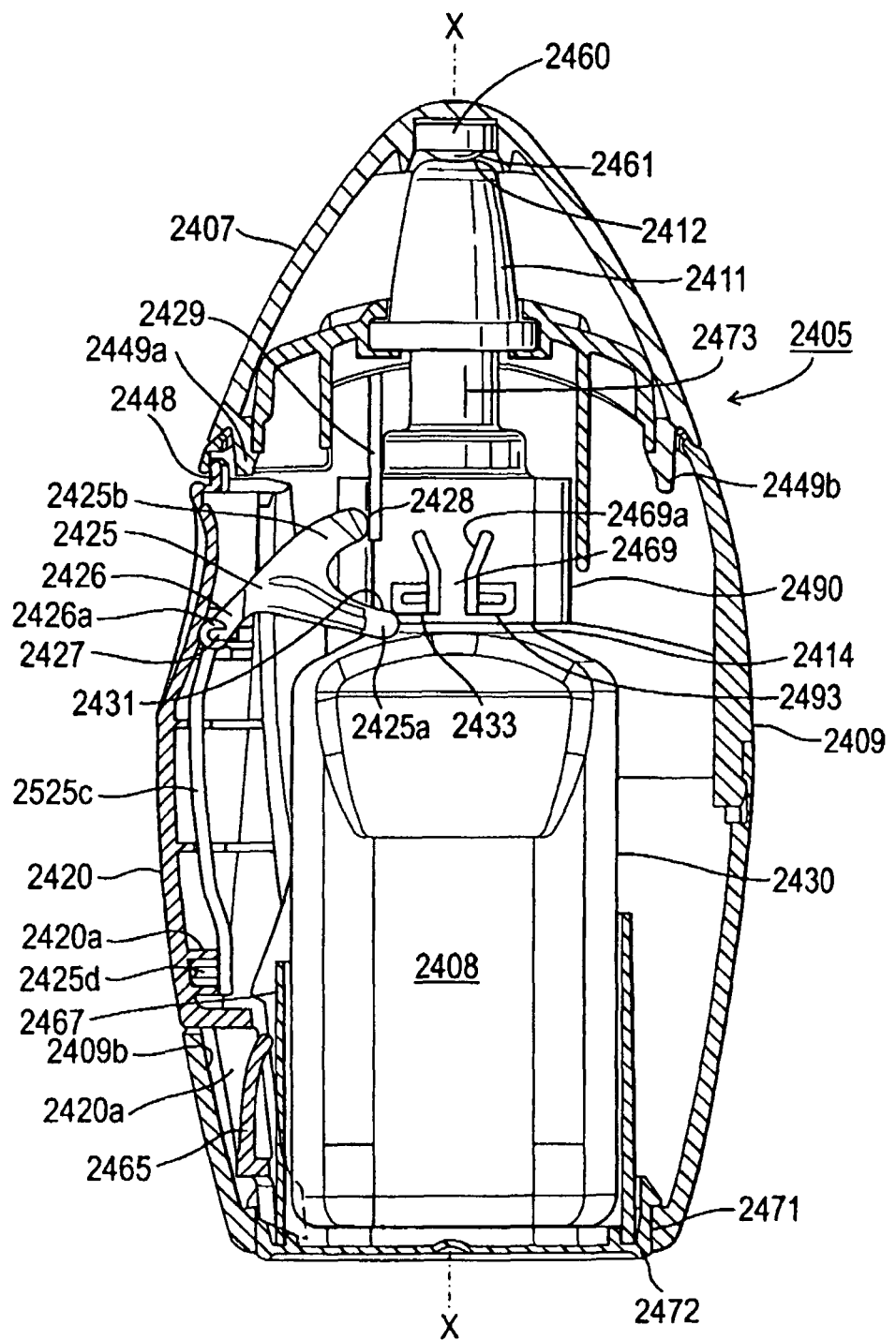

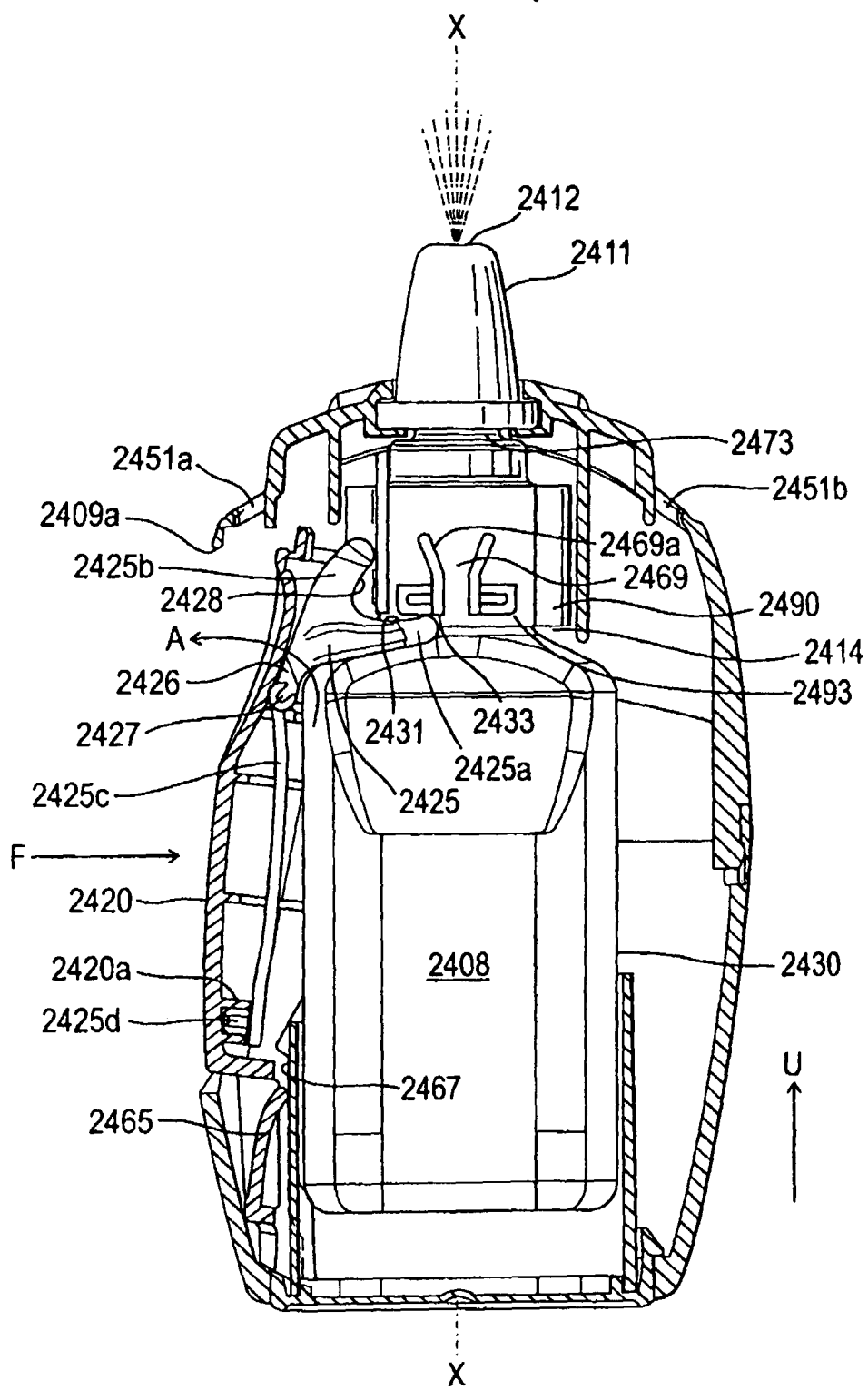

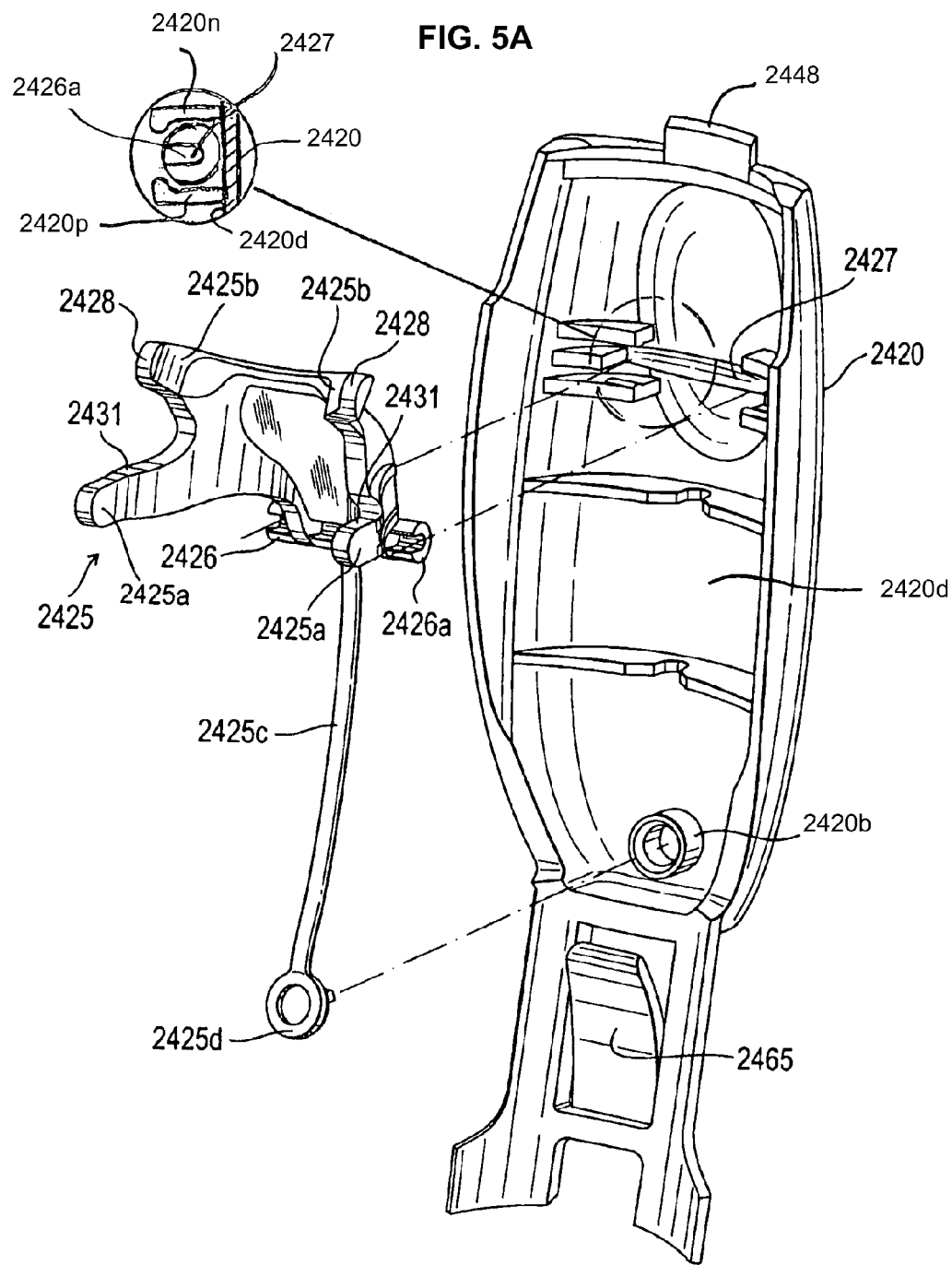

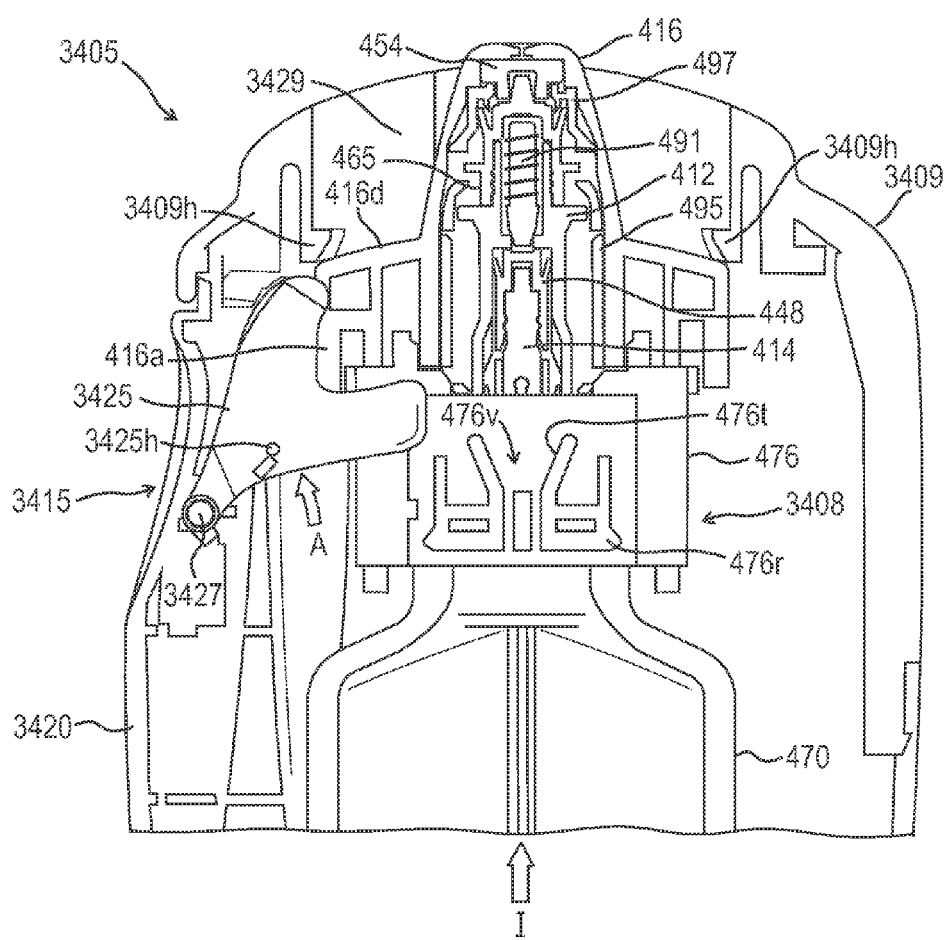

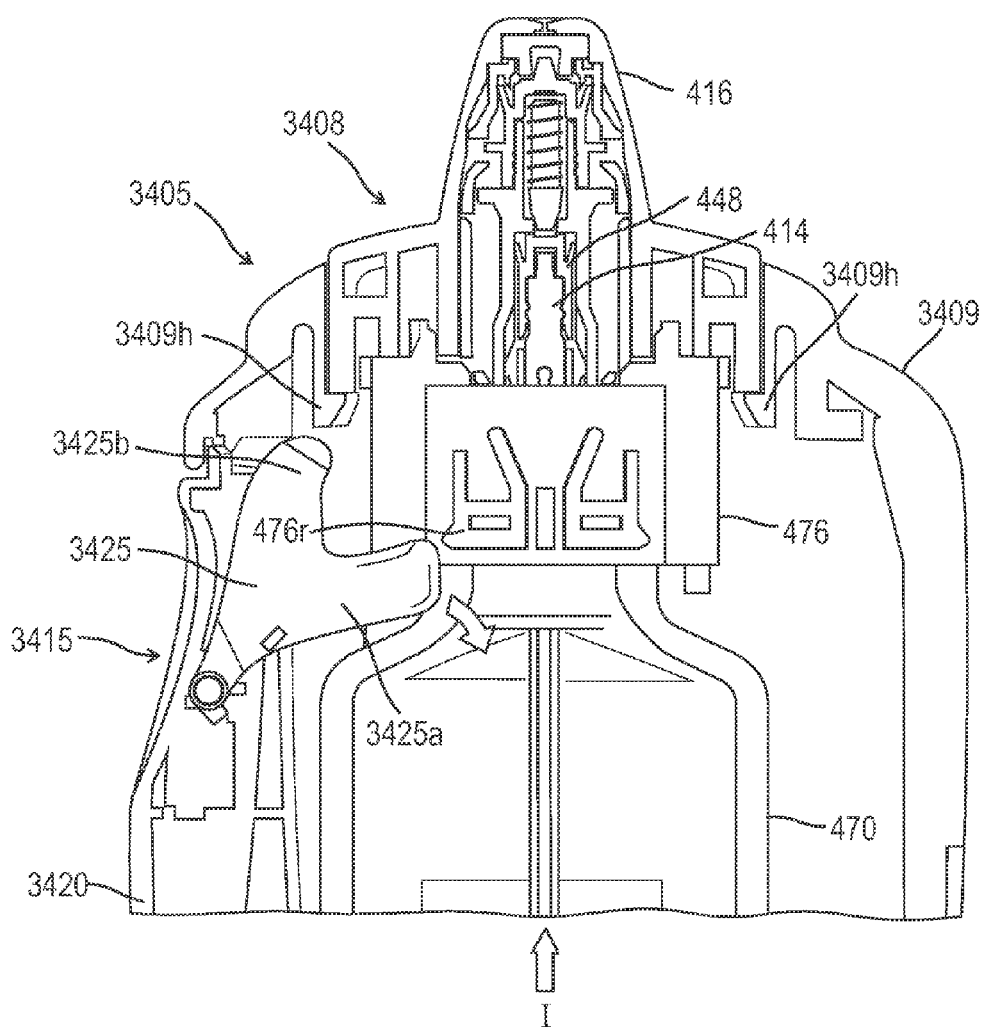

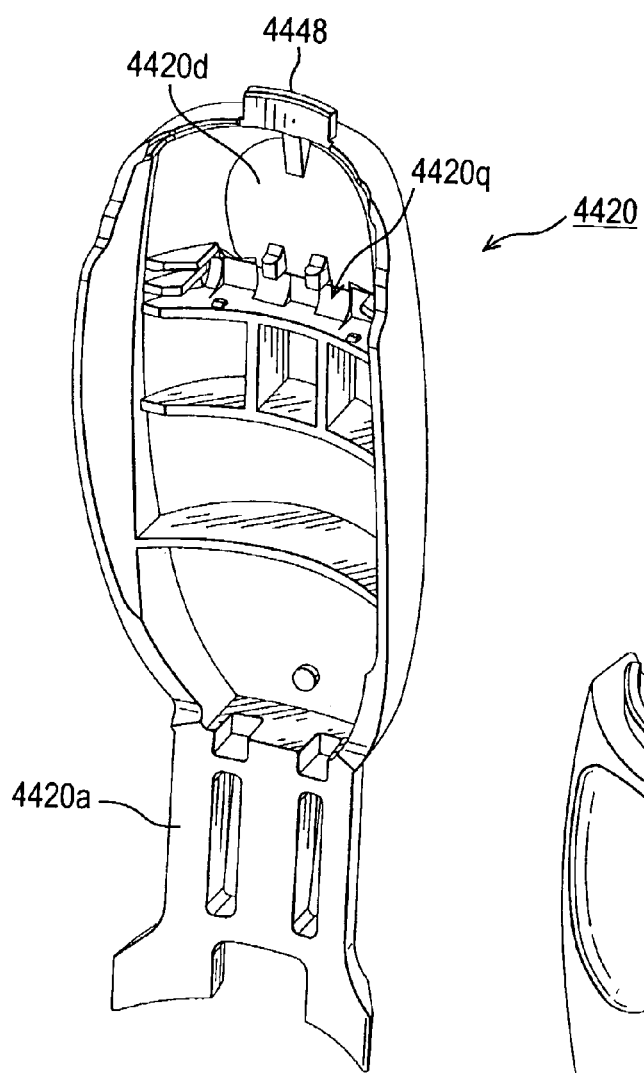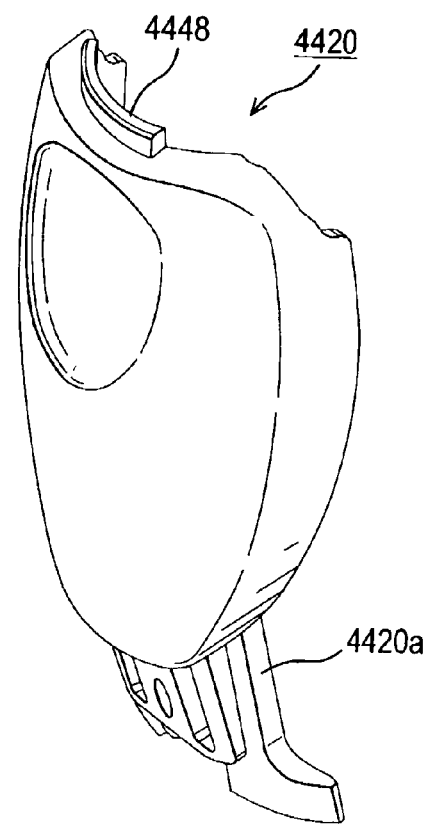

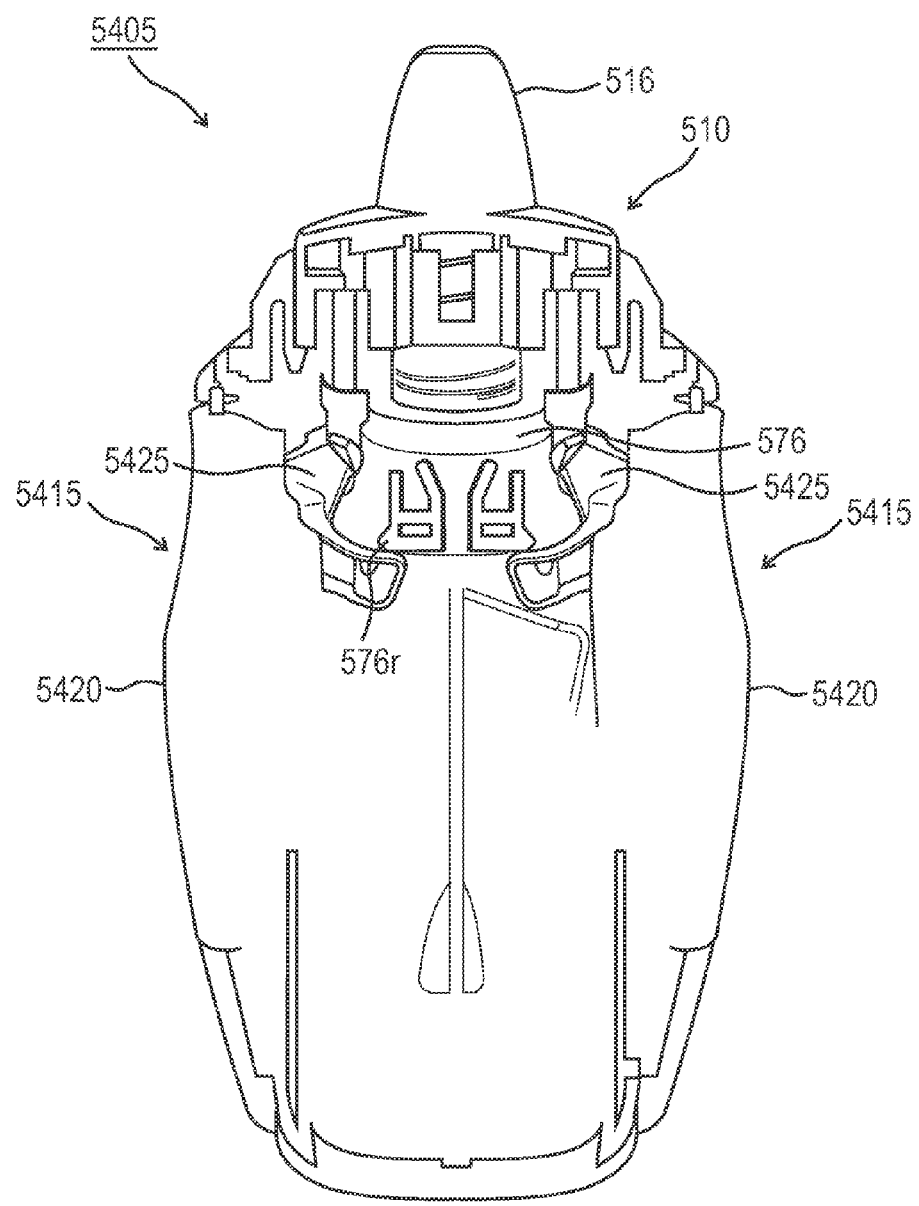

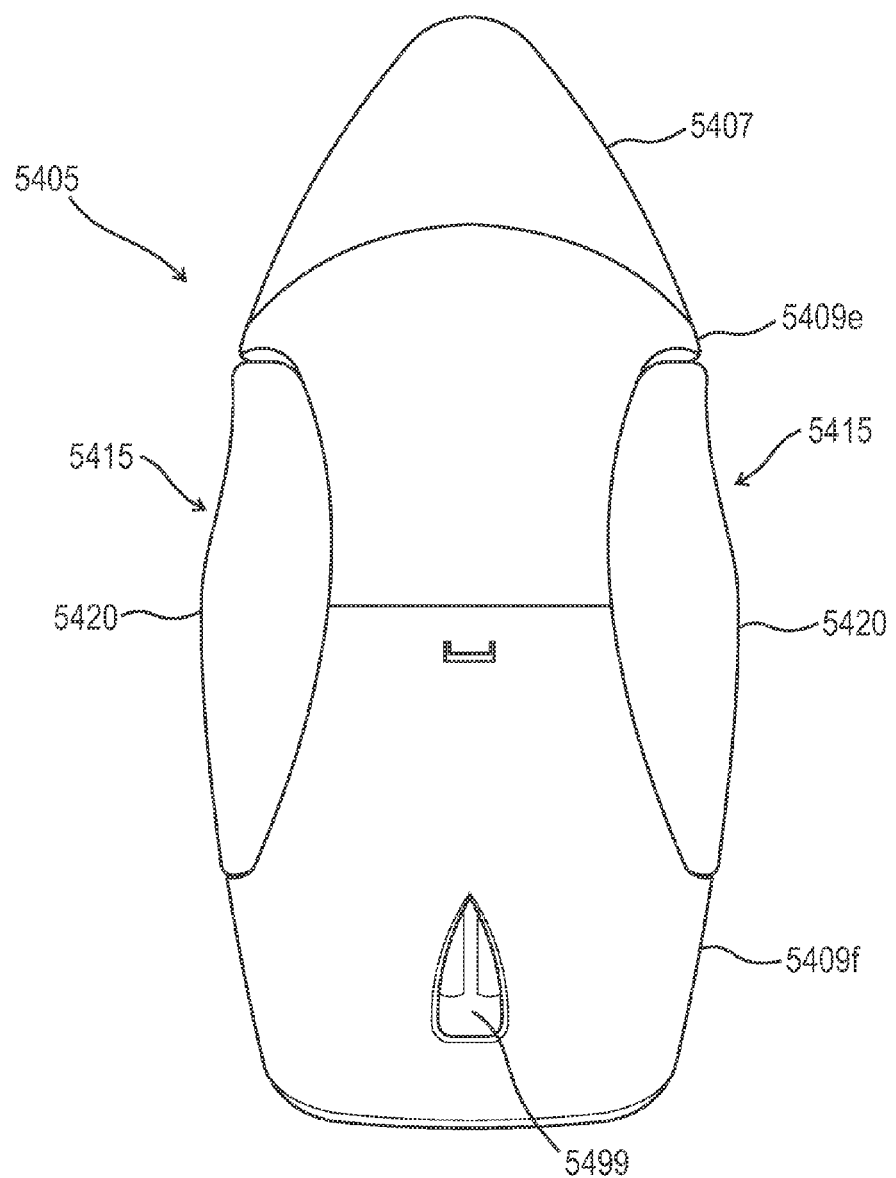

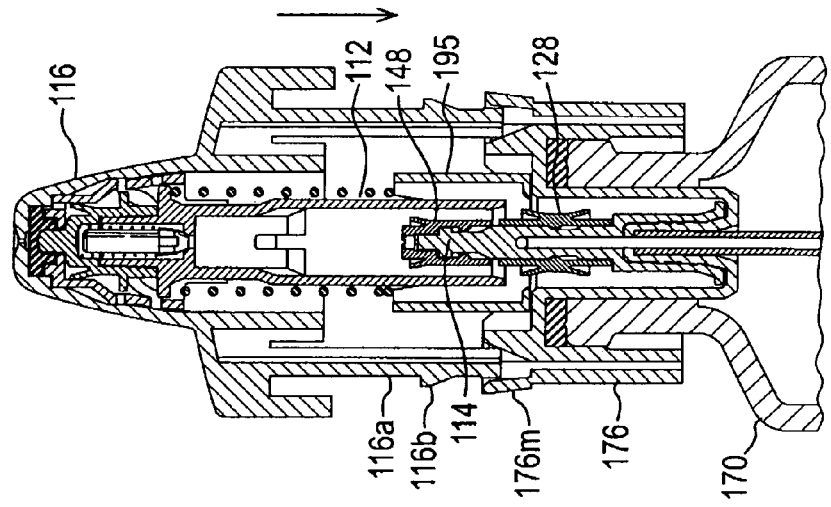
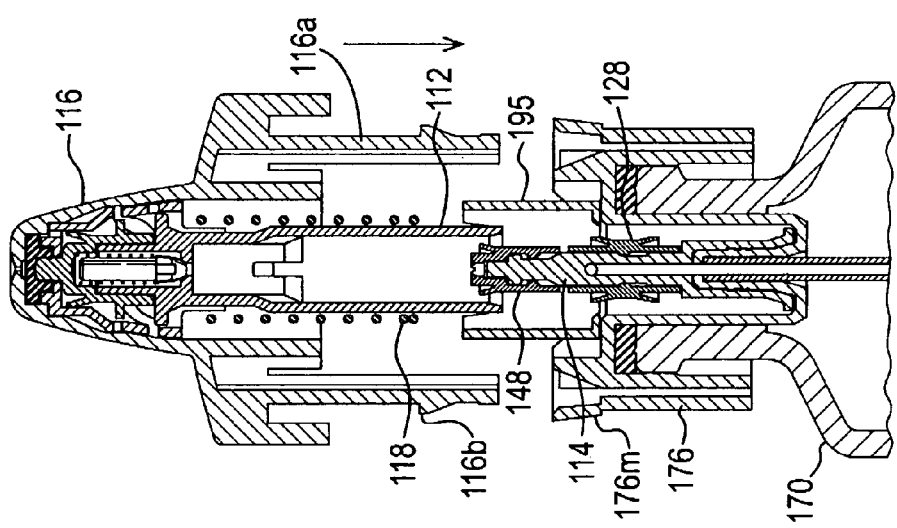
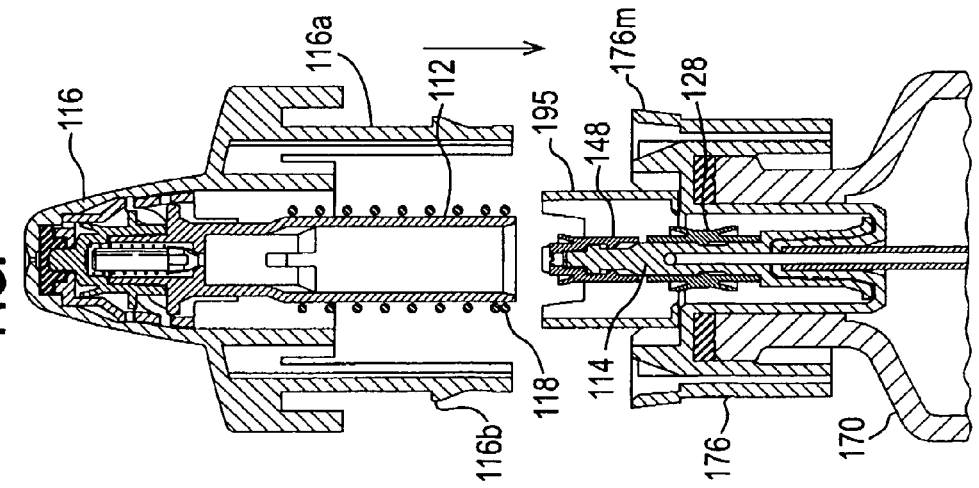

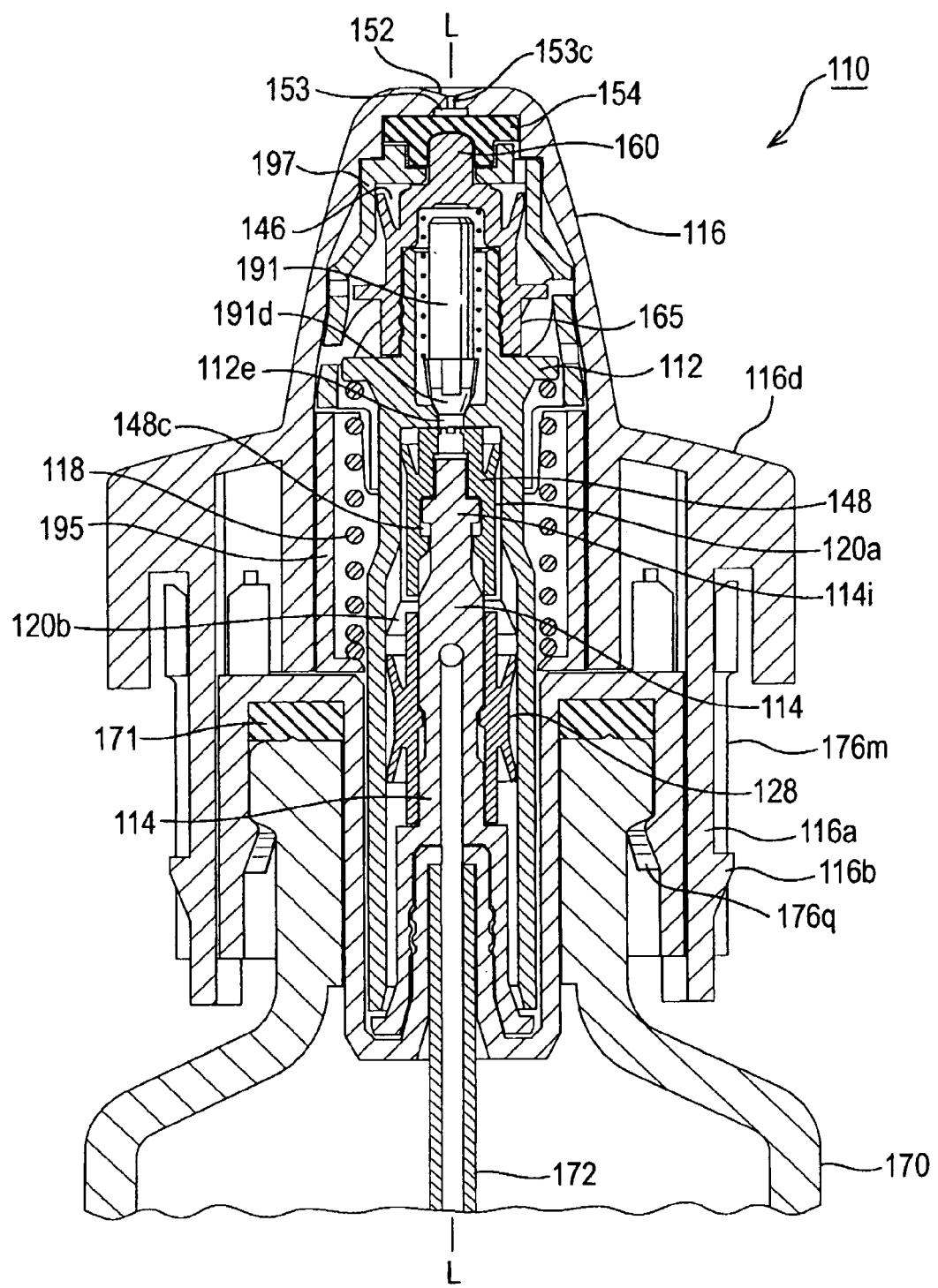

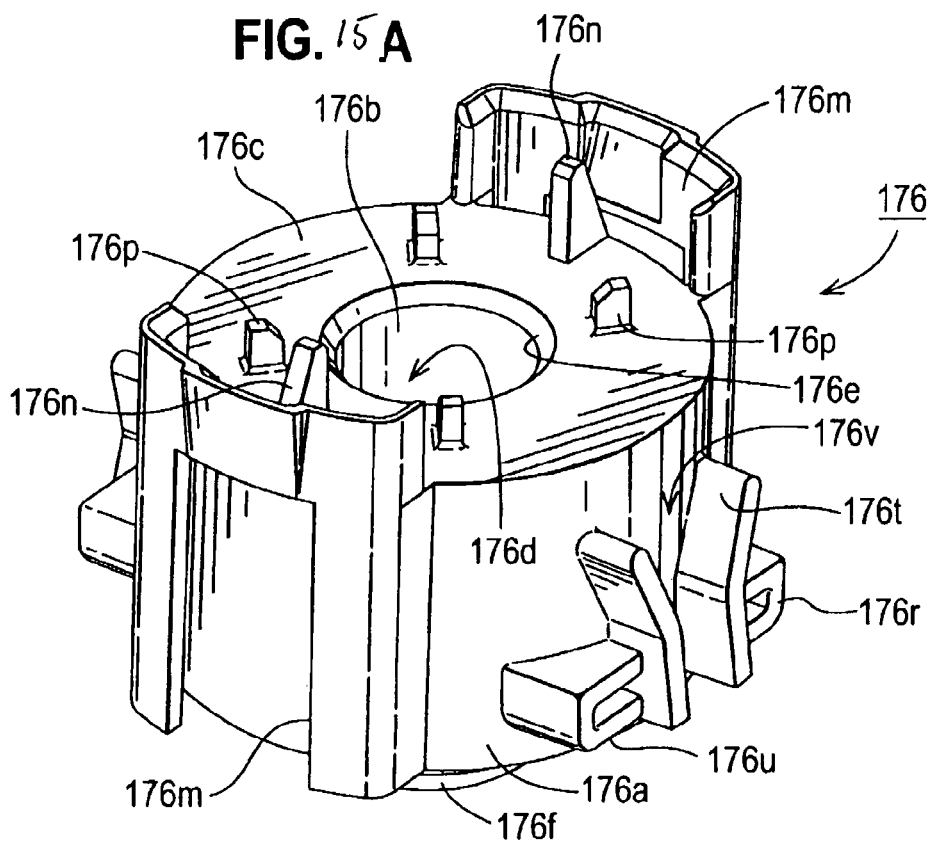
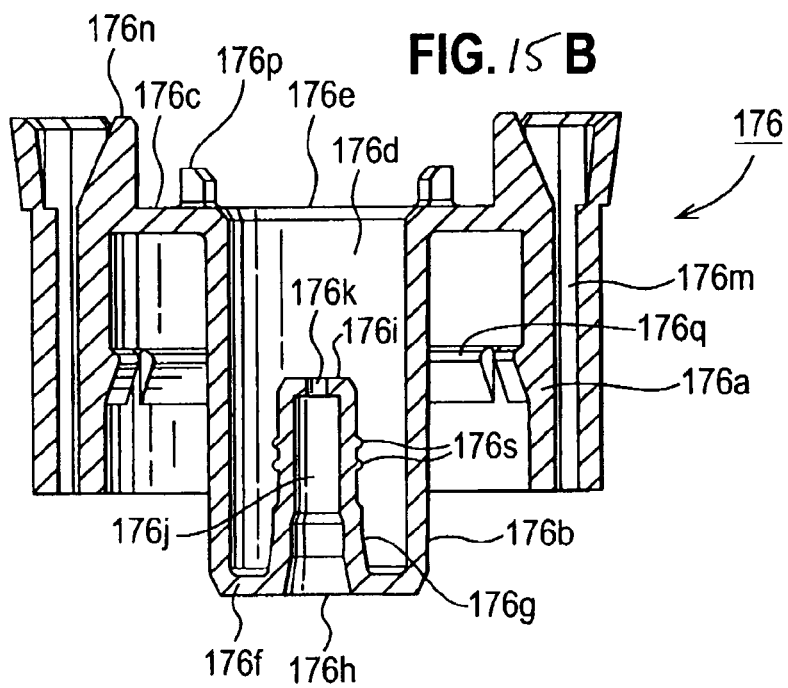

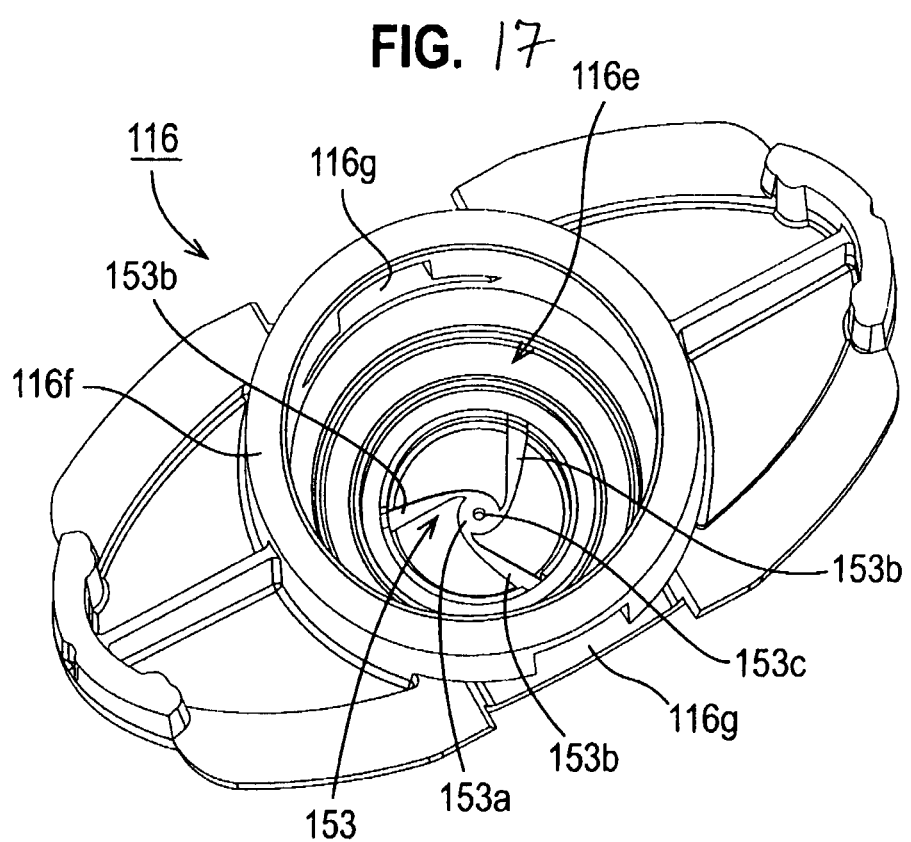

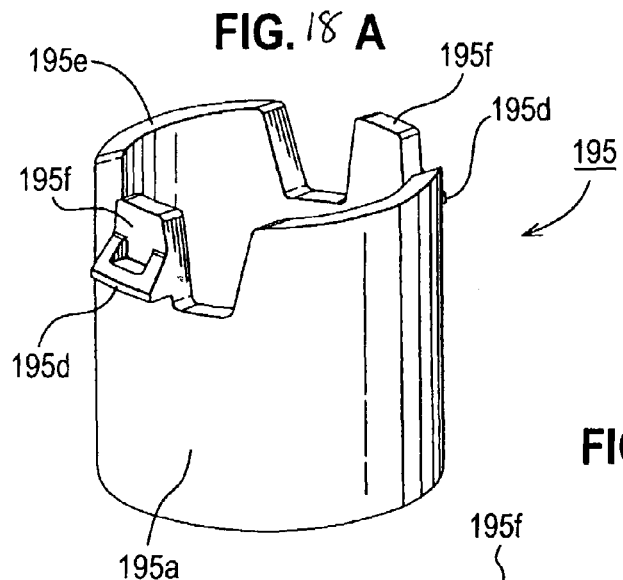
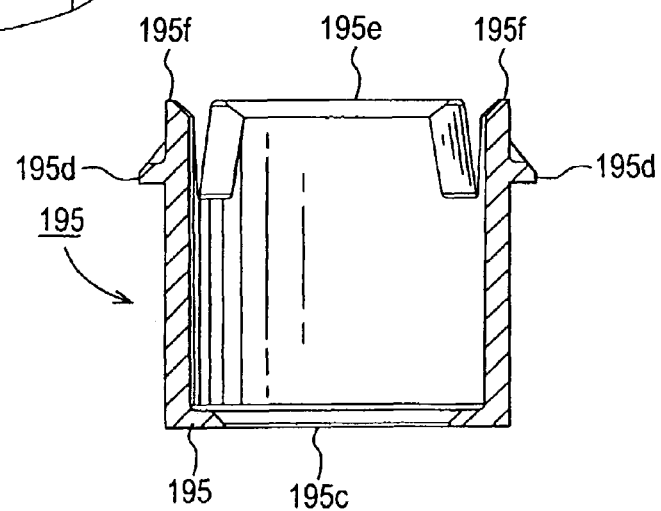
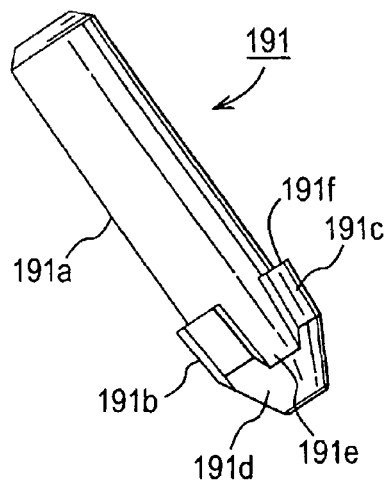
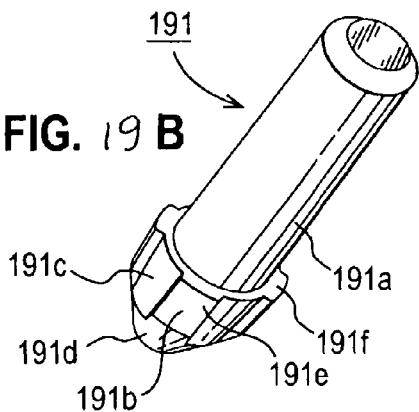

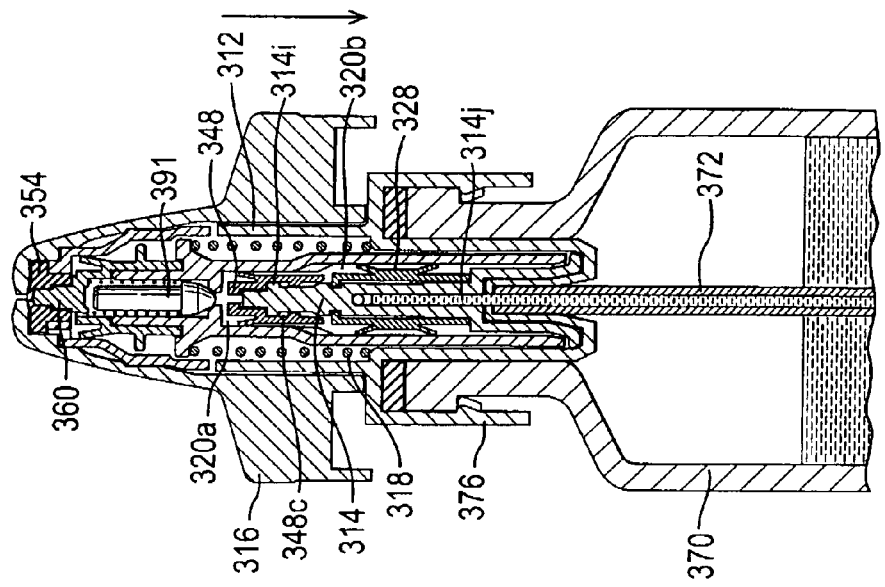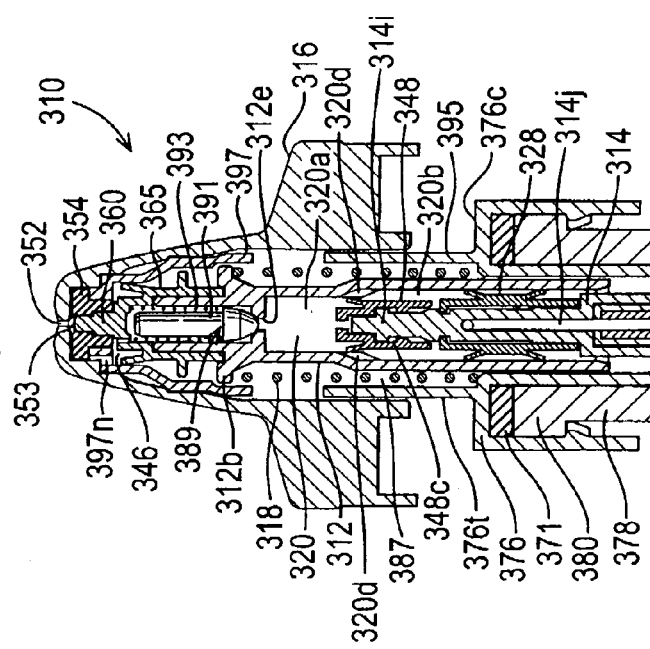

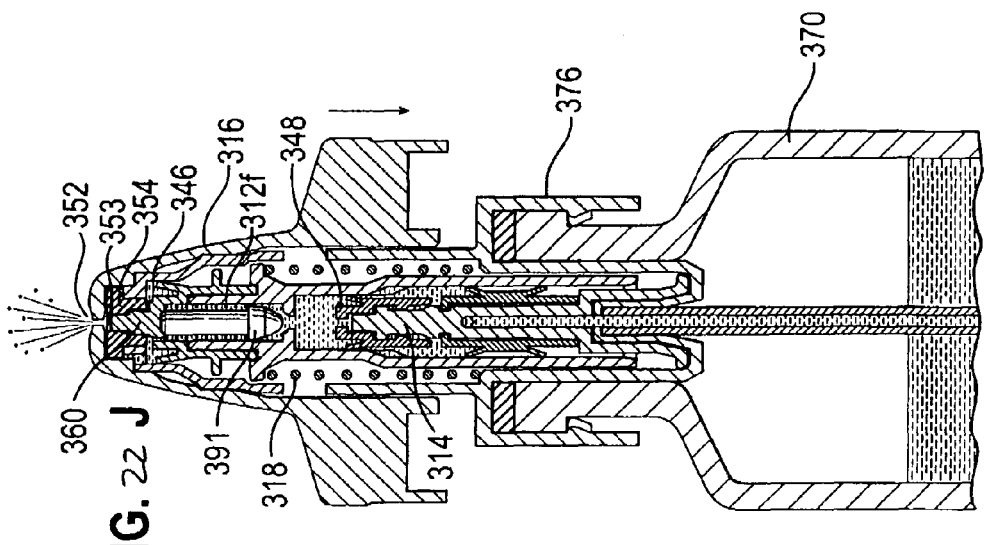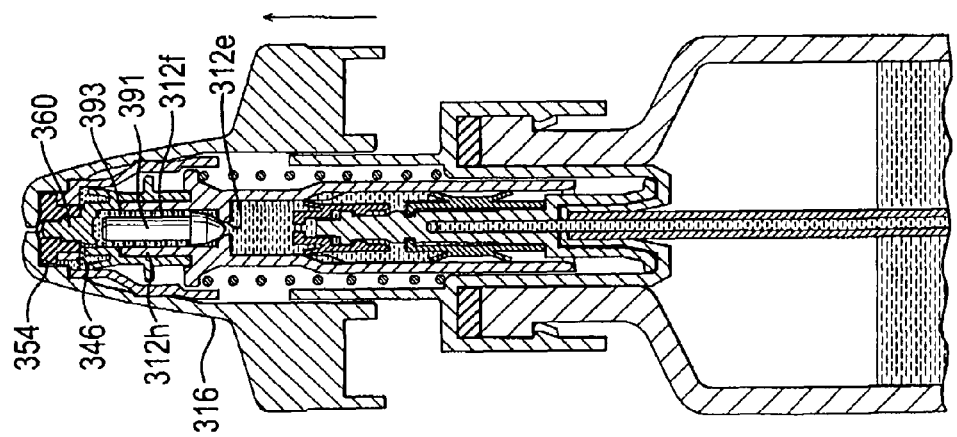

DISPENSING DEVICE

RELATED APPLICATIONS

This application is filed pursuant to 35 U.S.C. §371 as a United States National Phase Application of International Patent Application No. PCT/GB2008/003954 filed Nov. 27, 2008, which claims priority from UK Patent Application Nos. 0723418.0 and 0809770.1, respectively filed 29 Nov. 2007 and 29 May 2008, the contents of which are incorporated herein by reference.

FIELD OF THE INVENTION

The present invention relates to a dispensing device for dispensing a substance, for instance a fluid (e.g. liquid) substance, for instance an intra-nasal dispensing device, and is particularly, but not exclusively, concerned with a dispensing device for dispensing a pharmaceutical substance. The invention also relates to an actuator for a dispensing device, and an actuator mechanism.

BACKGROUND OF THE INVENTION

As background prior art there may be mentioned FR-A-2812826 (Valois S.A.). This describes with reference to FIGS. 6a and 6b a fluid product spray device comprising a housing, a fluid container mounted in the housing, and a lever and an angled rod which are independently pivoted at fixed pivot points on the housing. In use, the lever is pushed inwardly so as to contact a first arm of the angled rod and cause the angled rod to pivot on the housing such that a second arm of the angled rod lifts the fluid container to actuate a pump of the container and so dispense a quantity of fluid from the container.

The aim of the present invention in one aspect thereof is to provide a novel dispensing device. In another aspect, the invention aims to provide a novel actuator mechanism for a dispensing device.

SUMMARY OF THE INVENTION

In one aspect of the present invention there is provided a device for dispensing a substance according to claim 1 hereof.

In another aspect of the present invention there is provided an actuator mechanism according to claim 29 hereof.

In a further aspect of the present invention there is provided an actuator for a dispensing device comprising the actuator mechanism of the invention.

Other aspects and features of the present invention are set out in the other claims or in the detailed description of exemplary embodiments of the invention made with reference to the accompanying Figures of drawings. Each aspect of the invention can comprise one or more features of one or more of the other aspects and/or of one or more of the exemplary embodiments hereinafter to be described.

BRIEF DESCRIPTION OF THE DRAWINGS

FIG. 2 corresponds to FIG. 1, but with the protective end cap removed and the first device having been actuated;

FIG. 3 is a side elevation, partly in section, of a second fluid dispensing device in accordance with the present invention, the device being at rest with a protective end cap in place;

FIG. 4 corresponds to FIG. 3, but with the protective end cap removed and the second device having been actuated;

FIG. 5A shows a finger-operable actuator mechanism of the second device;

FIGS. 6A-D show steps in the assembly of a third fluid dispensing device in accordance with the present invention.

FIGS. 6J and 6K are perspective views of the lever of the fourth fluid dispensing device;

FIG. 6L is an open front view of a fifth fluid dispensing device in accordance with the invention comprising a pair of finger-operable actuator mechanisms;

FIG. 6M is a further front view of the fifth fluid dispensing device with a protective cap;

FIG. 7A shows the fluid dispenser in a fully extended (open) position and FIGS. 7B and 7C respectively show the fluid dispenser in its rest and fired positions;

FIGS. 8A to 8C illustrate the assembly of the fluid dispenser of FIGS. 7A-C;

FIGS. 9A to 9C are cross-sectional side views of the fluid dispenser of FIGS. 7A-C in its fully extended, rest and fired positions, respectively;

FIGS. 15A and 15B are respectively perspective and cross-sectional side views of a stopper portion of the fluid dispenser of FIGS. 7 to 10 which mounts on a fluid supply and to which mounts the piston member of FIGS. 11A-B;

FIG. 17 is a perspective rear view of the nozzle of FIGS. 16A and 16B showing a swirl chamber formed in the end face thereof;

FIGS. 18A and 18B are respectively perspective and cross-sectional side views of a carrier member of the fluid dispenser of FIGS. 7 to 10 which slidingly mounts on the nozzle of FIGS. 16A-B and 17;

FIGS. 19A and 19B are perspective views of a valve element of a valve mechanism of the fluid dispenser of FIGS. 7 to 10 which mounts in the main housing of FIGS. 14A-B;

FIG. 35 is an enlarged fragmentary view of an alternative tip seal arrangement for the fluid dispenser of FIG. 33;

DETAILED DESCRIPTION OF THE DRAWINGS

In the following description of non-limiting specific embodiments according to the present invention, any terms concerning the relative position, orientation, configuration, direction or movement of a given feature (e.g. "upper", "anti-clockwise" etc.) relate only to the arrangement of that feature from the view point shown in the specific Figure or Figures to which the description refers. Moreover, these terms are not meant to be limiting on the arrangement for the invention, unless stated otherwise.

Furthermore, each of the following specific embodiments is for dispensing a liquid and use of the word "fluid" in the description thereof is to be interpreted as referring to a liquid. The liquid may contain a medicament, for example suspended or dissolved in the liquid.

Figure 1:
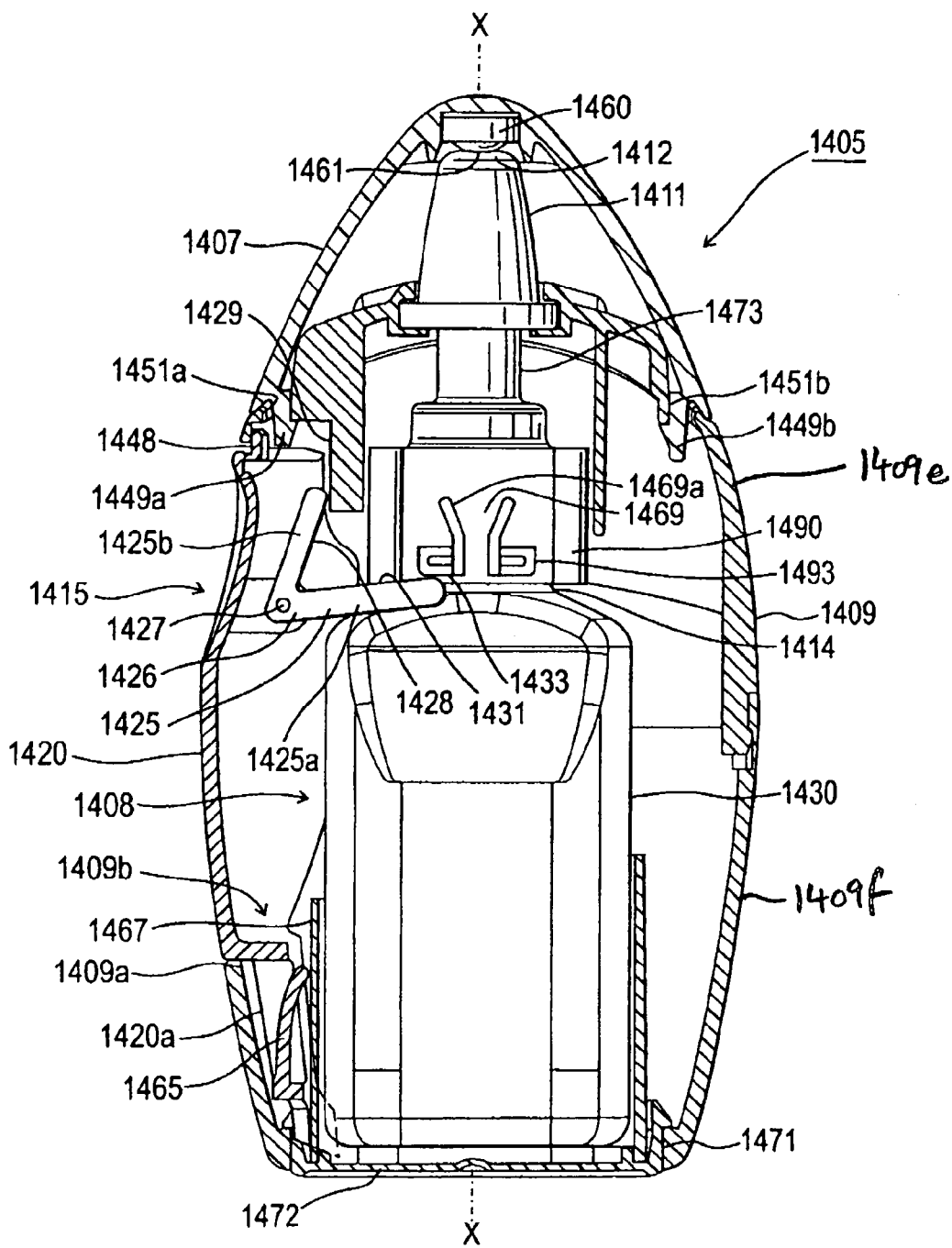
FIG. 1 is a side elevation, partly in section, of a first fluid dispensing device in accordance with the present invention, the device being at rest with a protective end cap in place.

FIGS. 1 and 2 show a first fluid dispensing device 1405 for dispensing or spraying a fluid in accordance with the present invention. The dispensing device has similarity with that disclosed in US-A-2007/0138207, derived from WO-A-2005/087615, the contents of which prior applications are hereby incorporated herein by reference.

In this particular, non-limiting, embodiment, the fluid dispensing device 1405 is hand-held and hand-operable and, moreover, is adapted for spraying a fluid into the nasal cavity of a human being, although the device 1405 may be adapted to spray a fluid into other body cavities. The fluid dispensing device 1405 is further adapted to allow a user to spray the fluid into their own nasal cavity for self-administration, but might also be used by a user to spray fluid into another person's nasal cavity.

Referring to FIGS. 1 and 2, the fluid dispensing device 1405 comprises a hollow, rigid plastics housing 1409 (e.g. made of ABS) and, at a first (upper) end of the housing 1409, a separately-formed, rigid plastics nozzle 1411 which is sized and shaped for insertion into the nasal cavity of a human being. The housing 1409 comprises upper and lower housing halves 1409e, 1409f, which snap fit together.

A fluid discharge device 1408 is received in the housing 1409 such that its longitudinal axis X-X is aligned with (i.e. in-line or co-axial with) the nozzle 1411 and, more particularly, the longitudinal axis of the housing 1409 (the "housing axis"). The fluid discharge device 1408 is mounted in the housing 1409 for reciprocal translation along its longitudinal axis X-X and the housing axis, as will be described in greater detail hereinafter.

For simplicity, the following description will mainly refer to the longitudinal axis X-X, but it is to be understood that each such reference applies equally to the housing axis.

In this embodiment, the nozzle 1411 has a frusto-conical shape with a circular or substantially circular cross-section. The nozzle 1411 has a discharge orifice (not shown) in its tip 1412 and an inner hollow post (not shown) in fluid communication with the discharge orifice (see US-A-2007/0138207 supra) such that, in use of the fluid dispensing device 1405, fluid pumped upwardly through the post is discharged through the discharge orifice of the nozzle 1411. More particularly, a swirl chamber (not shown) is provided to the underside of the discharge orifice such that fluid pumped through the post is provided with angular momentum so as to be discharged as an atomised spray from the discharge orifice of the nozzle 1411, as will be understood by those skilled in the art.

The discharge orifice and the inner hollow post of the nozzle 1411 lie on the housing axis, and thus align with the longitudinal axis X-X when the fluid discharge device 1408 is received in the housing 1409.

The outer surface, or a part of the outer surface, of the nozzle 1411 may be made from a soft-touch plastics material. However, in this embodiment the nozzle 1411 is made from polypropylene (PP), although other engineering plastics materials could be used.

The fluid discharge device 1408 comprises a rigid container 1430, for storing enough fluid for multiple metered doses thereof to be dispensed, a compression pump (not shown) crimped to the container 1430, as known in the art, and a rigid cylindrical collar 1490 (e.g. made of acetal) permanently fixed to the container 1430 over the pump.

In this particular embodiment of the invention, the container 1430 contains a fluid medicament. Consequently, the container 1430 is made from a pharmaceutically-acceptable material, in this case of a glass material, although other pharmaceutically-acceptable container materials could be used, for instance of a plastics material. In this embodiment, the container material is transparent or translucent, so that the content therein can be viewed, but opaque containers could be used within the scope of the present invention. When a transparent/translucent container material is used, one or more windows (not shown, but see window 3499, FIG. 6A) may be provided in the housing 1409 so that the amount of fluid in the container 1430 can be determined by the user.

The collar 1490 is permanently fixed to the container 1430 through use of a split collar (not shown) provided on the crimp about the neck 1414 of the container 1430 in the manner described in US-A-2003/0136800 and US-A-2006/0082039, also hereby incorporated herein by reference. More particularly, the collar 1490 is fixed by the split collar against axial movement on the container 1430, but is free to rotate thereon.

To guide the reciprocal displacement of the fluid discharge device 1408 in the housing 1409 along the longitudinal axis X-X, a pair of diametrically opposing embossments 1493 (only one shown) on the collar 1490 provide the collar 1490 with a pair of diametrically opposed, axially-oriented tracks 1469 (only one shown). When the fluid dispensing device 1408 is mounted in the housing 1409, the rotary position of the collar 1490 on the container 1430 is set such that the tracks 1469 align with complementary, axially-oriented runners (not shown, but see runner 3409r, FIG. 6A) formed on the inside surface of the housing 1409. Moreover, each track 1469 has a funnel shape 1469a at its upper end to help guide the tracks 1469 onto the runners when the fluid discharge device 1408 is inserted or loaded into the housing 1409 through a (lower) opening 1471 in a second (lower) end of the housing 1409, which lower opening 1471 is subsequently closed with an end cap 1472 (e.g. made of ABS).

In use, when the fluid discharge device 1408 is axially displaced in the housing 1409, the tracks 1469 ride over the runners. As will be appreciated, the co-operation of the tracks 1469 with the runners not only guides the longitudinal displacement of the fluid discharge device 1408 in the housing 1409, but also prevents the collar 1490, and in fact the fluid discharge device 1408 as a whole, from rotating in the housing 1409.

It will be appreciated that runners could be provided on the fluid discharge device 1408 and complementary tracks provided on the inside of the housing 1409 to like effect.

In addition to the collar tracks 1469, the collar 1490 also has a sheath 1473 for sheathing the pump stem (not shown) of the compression pump. The sheath 1473 is a sliding fit on the inner hollow post of the nozzle 1411. Although not shown, when the fluid discharge device 1408 is inserted into the housing 1409, the sheath 1473 slides over the nozzle inner post and locates the pump stem inside the nozzle inner post against a step formed therein. Thus, the pump stem cannot move farther upwardly (i.e. remains stationary) in the housing 1409 when the fluid discharge device 1408 is translated upwardly, resulting in relative movement between the pump stem and the rest of the fluid discharge device 1408. In this way, the pump is compressed and a metered dose of the fluid pumped from the pump stem, as will be understood by the skilled reader. As described above, this metered dose is pumped into the inner post of the nozzle 1411 and out of the nozzle discharge orifice as an atomised spray.

The fluid dispensing device 1405 comprises a finger-operable actuator mechanism 1415 to apply a lifting force to the fluid discharge device 1408 directed along the longitudinal axis X-X to result in the pump pumping a metered dose of the fluid from the nozzle 1411. More particularly, and as shown by comparison of FIGS. 1 and 2, the lifting force applied by the finger-operable actuator mechanism 1415 causes the fluid discharge device 1408 to translate upwardly along the longitudinal axis X-X relative to the stationary pump stem so that a metered dose of fluid is released.

As shown, the finger-operable actuator mechanism 1415 is mounted to the housing 1409 so as to be movable (i) inwardly, in an actuating direction which is transverse to the longitudinal axis X-X, from the rest position of FIG. 1 to the operational position of FIG. 2 to effect the upward dispensing movement of the fluid discharge device 1409 (arrow U, FIG. 2), and (ii) outwardly, in an opposite, return direction which is transverse to the longitudinal axis X-X, from the operational position back to the rest position to enable the fluid discharge device 1408 (and the pump in particular) to reset ready for the next actuation of the fluid dispensing device 1405 to release another metered dose of the fluid. This reversible inward transverse movement of the finger-operable actuator mechanism 1415 is able to continue until no more fluid is able to be pumped from the container 1430 (i.e. until the container 1430 is empty or nearly empty of the fluid). The finger-operable actuator mechanism 1415 is provided with a biasing force which biases the finger-operable actuator mechanism to its rest position.

The finger-operable actuator mechanism 1415 in this particular embodiment has two members, namely (i) a finger-operable, rigid first member 1420 mounted to the housing 1409 to move inwardly-outwardly transversely to the longitudinal axis X-X relative to the housing 1409, and (ii) a second rigid member 1425 carried on the first member 1420 so as to move therewith and to lift the fluid discharge device 1408 relative to the stationary pump stem upon inward movement on the first member 1420. The first and second members are made from a plastics material, and may be of ABS and acetal, respectively.

As will be understood from FIG. 1, the first member 1420 is formed separately from the housing 1409 and is mounted in a slot 1409a formed in the side of the housing 1409.

The first member 1420 is provided with a biasing or spring element 1465, here in the form of a leaf spring, to provide the biasing force to bias the actuator mechanism 1415, and more particularly the first member 1420, to its rest position.

As will also be seen from FIGS. 1 and 2, the first member 1420 is pivotally mounted to the housing 1409 so that the inward-outward movement of the first member 1420 transverse to the longitudinal axis X-X is an arcuate movement. The first member 1420 has a lower end 1420a which fits into an axial channel 1409b formed in the housing 1409 and about which the first member 1420 pivots. The lower end 1420a carries the leaf spring 1465 which acts against an inner wall 1467 of the housing channel 1409b to provide the return biasing force on the first member 1420. In this particular embodiment, the first member 1420 is a lever.

As will be seen from comparison of FIGS. 1 and 2, the second member 1425 is pivotally mounted on the first member 1420 such that upon application of an inward transversely-directed force (arrow F, FIG. 2) to the first member 1420 by a user's finger(s) and/or thumb, which can be of the same hand holding the fluid dispensing device 1405, the second part 1425 is able to pivot in an anti-clockwise sense (arrow A, FIG. 2) as it is carried inwardly by the inwardly moving first member 1420. In this particular embodiment, the second part 1425 is a crank, more particularly a bell crank.

In more detail, the bell crank 1425 has a mounting section 1426 for mounting to the lever 1420 and a first pair of arms 1425a, 1425b extending from the mounting section 1426. The mounting section 1426 of the bell crank 1425 is pivotally mounted to the lever 1420 at a fixed pivot point 1427. In this particular embodiment, the mounting section 1426 and the first pair of arms 1425a, 1425b form a generally V- or U-shape.

The bell crank 1425 further comprises an identical second pair of arms (not shown) extending from the mounting section 1426. The second pair of arms are located on the far side of the fluid discharge device 1408 as viewed in FIGS. 1 and 2, hence why not shown. The result of this bell crank configuration is that the fluid discharge device 1408 is straddled by the first (lower) arm 1425a of each pair of arms, the first arm 1425a of the first pair being on the near side (as viewed in FIGS. 1 and 2) and the corresponding first arm of the second pair being on the far side. This will be further understood by reference to the similar bell crank configuration shown in FIGS. 5A and 5B, where like reference numerals indicate like features, and with the pairs of first and second arms being labelled 2425a, 2425b, respectively.

The first arms 1425a of each pair extend in a direction generally transverse to the longitudinal axis X-X, whereas the second arms 1425b are angled more upwardly towards the nozzle 1411. As can be seen, there is an angle of no more than 90° between the first and second arms 1425a, 1425b, and in this particular embodiment an angle of less than 90°.

As will be appreciated from FIG. 2, the configuration of the second arm 1425b in each pair is such that when the bell crank 1425 travels inwardly with the lever 1420, an inner surface 1428 of the second arms 1425b contacts a pusher surface 1429 in the housing 1409 thereby causing the bell crank 1425 to pivot in the anti-clockwise sense A about the pivot point 1427. In fact, the second arms 1425b also slide up the pusher surface 1429 as the bell crank 1425 moves inwardly with the lever 1420. The engagement of the second arms 1425b on the pusher surface 1429 helps to guide the pivotal movement of the bell crank 1425 and also supports the bell crank 1425 when lifting the fluid discharge device 1408.

The pusher surface 1429 for the second arms 1425b may be presented by a single wall feature of the housing 1409 or by separate housing wall features.

As stated, the first arms 1425a extend from the pivot axis passing through the pivot point 1427 in a direction generally transverse to the longitudinal axis X-X. The afore-described pivotal movement of the bell crank 1425 in the anti-clockwise sense A causes a lifting surface 1431 of each first arm 1425a to contact a bearing surface 1433 of the fluid discharge device 1408 and lift the fluid discharge device 1408 towards the nozzle 1411 along the longitudinal axis X-X relative to the stationary pump stem to cause a metered dose of fluid to be dispensed. In this particular embodiment, the bearing surface 1433 is provided on the collar 1490, more particularly by the diametrically-opposed embossments 1493 on the collar 1490.

The fluid dispensing device 1405 further comprises a protective end cap 1407 for protection of the nozzle 1411. The end cap 1407 has first and second lugs 1449a, 1449b to project from the protective end cap 1407 for receipt within suitably arranged channels 1451a, 1451b provided to the upper end of the housing 1409 to securely attach the end cap 1407 to the housing 1409 to cover the nozzle 1411. When so-received, the first lug 1449a further interferes with movement of the finger-operable actuator mechanism 1415, and in this particular instance the lever 1420 thereof, such as to prevent actuation (i.e. to lock movement) of the actuator mechanism 1415 when the end cap 1407 and lugs 1449a, 1449b are in place (i.e. in the nozzle covered position). The end cap 1407 is suitably made from the same material as the housing, e.g. a plastics material, suitably ABS.

The end cap 1407 also has a protruding stopper 1460 which has a convex, resilient end form 1461 arranged for sealing engagement with the discharge orifice (not shown) in the nozzle 1411 when the end cap 1407 is in the nozzle covered position so as provide an essentially airtight seal to the nozzle discharge orifice to prevent fluid drain back between actuations of the fluid dispensing device 1405. The stopper 1460 may be made from a thermoplastic elastomer, for example SANTOPRENE®.

To use the fluid dispensing device 1405, a user first has to remove the protective end cap 1407 thereby unsealing the nozzle orifice. The user then grasps the fluid dispensing device 1405 in one hand and places a thumb and/or finger of that hand on the lever 1420. The user places the nozzle 1411 in their nostril (or a nostril of another person) and applies the transverse force F to the lever 1420 so that the lever moves from the rest position of FIG. 1 to the operational (or actuated) position of FIG. 2. In so doing, this causes the bell crank 1425 to pivot in the anti-clockwise sense A and the lifting arms 1425a to act on the embossments 1493 to lift the fluid dispensing device 1408 upwardly U relative to the stationary pump stem far enough to compress the pump for release of a metered dose of the fluid medicament into the nasal cavity. The user then releases the force F applied to the lever 1420 to allow the actuator mechanism 1415 and the fluid discharge device 1408 to reset to the positions shown in FIG. 1.

The user would then repeat the lever operation one or more times to release a corresponding number of further metered doses and/or replace the protective cap 1407 until another medicament dose is needed. The number of medicament doses to spray into the nasal cavity at any given time would be determined by the dosing regimen for the fluid medicament being administered. The dosing procedure can then be repeated until all, or nearly all, of the fluid in the container 1430 has been administered.

To assist in assembly of the fluid dispensing device 1405, the lever 1420 may initially be disposed in an outward position with respect to the housing 1409 to allow the fluid discharge device 1408 to be inserted into the housing 1409 through the lower opening 1471, which is then closed by the end cap 1472. This is achieved by first inserting the lower end 1420a of the lever 1420 through the housing slot 1409a to be received in the axial channel 1409b without pivoting the lever 1420 inwardly to its rest position of FIG. 1. This is the "outward position" of the lever 1420 and enables the fluid discharge device 1408 to be inserted into the housing 1409 through the lower housing opening 1471 to, or near to, its rest position shown in FIG. 1 because the lever 1420 and bell crank 1425 do not impede the loading of the fluid discharge device 1408.

After the fluid discharge device 1408 has been so loaded, the lever 1420 is moved inward to its rest position. This brings the inner surfaces 1428 of the second arms 1425b of the bell crank 1425 into engagement with the pusher surface(s) 1429 to cause anti-clockwise pivoting A of the bell crank 1425 so as to bring the lifting surfaces 1431 of the first arms 1425a into contact with the bearing surfaces 1433 of the collar 1490. However, if the fluid discharge device 1408 is not fully in its rest position after being loaded into the housing 1409, the anti-clockwise pivoting A of the bell crank 1425 on inward movement of the lever 1420 from its outward position to its rest position results in the lifting surfaces 1431 coming into contact with the bearing surfaces 1433 and applying a lifting force thereto to lift the fluid discharge device 1408 to its rest position. This provides for tolerances in the loading of the fluid discharge device 1408 into the housing 1409, which typically would be carried out on an automated (computer controlled) assembly line.

From the preceding paragraph it may also be appreciated that if the fluid dispensing device 1405 happened to be dropped, or otherwise impacted, such that the fluid discharge device 1408 is displaced from its rest position downwardly towards the end cap 1472, this would force the lever 1420 towards or to its outward position. The user then only has to push the lever 1420 back inwardly to its rest position for the bell crank 1425 to lift the fluid discharge device 1408 back to its rest position. This provides for easy user resetting of the device 1405 if such an event occurs.

As described in US-A-2007/0138207 supra, at the upper end of the lever 1420 there is provided a resilient tab 1448. In the outward loading position of the lever 1420 described above, the tab 1448 bears against the outer edge of the slot 1409a to prevent the lever 1420 being moved through the slot 1409a to its rest position of FIG. 1. To move the lever 1420 inwardly to its rest position, the tab 1448 is deflected downwardly to clear the outer edge of the slot 1409a and thus allow the lever to pass through the slot 1490a. The tab 1448 then returns to its extended position and bears against an inner edge of the slot 1409a to inhibit the lever 1420 moving back to its outward position. As shown in FIG. 1, when the lug 1449a of the protective cap 1407 is received in the channel 1451a, it is located in front of the tab 1448. It will therefore be gathered that the lever 1420 is prevented from moving inwardly when the cap 1407 is in place by the lug 1449a blocking inward movement of the lever tab 1448. Thus, actuation of the device 1405 is prevented.

The finger-operable actuator means 1415 may further include a biasing force to bias the second member 1425 about the pivot point 1427 in a clockwise sense so that the second arms 1425b are biased into engagement with the pusher surface(s) 1429. In the absence of the pusher surface(s) 1429, the second member 1425 would be biased to a downwardly-directed angular orientation on the lever 1420.

The biasing force for the second member 1425 may be provided by one or more biasing (e.g. spring) elements (not shown) located between the second member 1425 and the first member 1420, for instance located at the pivot connection therebetween. The biasing element(s) may be a torsion spring(s), although the skilled reader will be able to perceive of other appropriate springs. A suitable torsion spring arrangement is hereinafter described for a third fluid dispensing device 3405 with reference to FIG. 6E.

Alternatively, the biasing/spring element(s) may be integrally formed with the bell crank 1425, for instance as one or more spring legs projecting from the mounting portion 1426.

FIGS. 3 to 5 show a second fluid dispensing device 2405 in accordance with the present invention, which is again hand-held and hand-operable and with like reference numbers being used to denote features which correspond to those of the first fluid dispensing device 1405. In fact, the only effective difference between the second fluid dispensing device 2405 and the first dispensing device 1405 is the form of the second member 2425 of the finger-operable actuator mechanism 2415. For expediency, only this difference will be described in any detail, as recourse can be made to the description of the first fluid dispensing device 1405 for the other features and attributes.

Figure 5B:
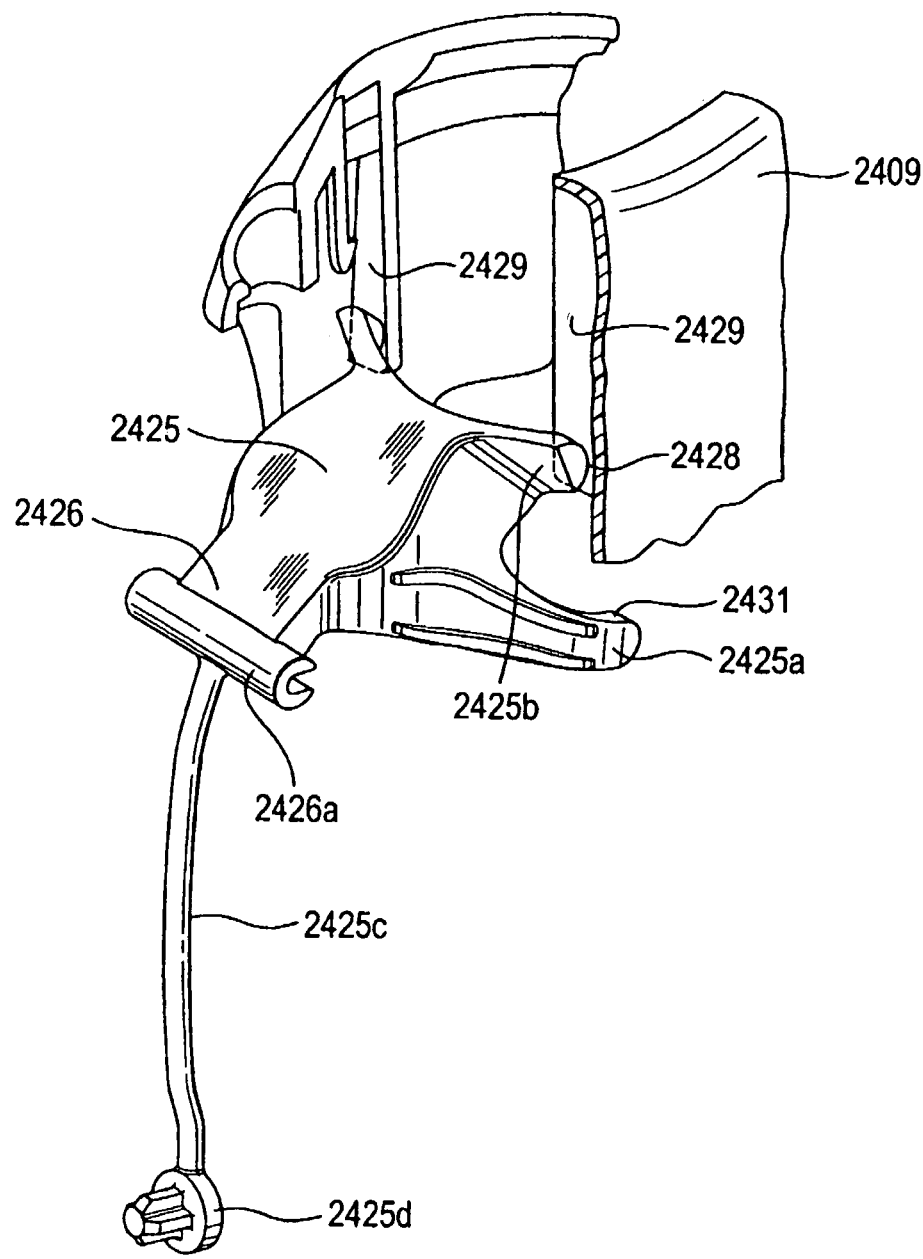
FIG. 5B shows the relationship of the finger-operable actuator mechanism with internal features of a housing of the second device.

The second member 2425 is again configured as a bell crank 2425 and functions in the same way as the bell crank 1425 of the first fluid dispensing device 1405. In other words, when the lever 2420 is moved inwardly from the rest position of FIG. 3 to the operational position of FIG. 4, the bell crank 2425 pivots in an anti-clockwise sense A about the pivot point 2427 as it travels inwardly on the lever 2420 due to the second arms 2425b reacting on, and sliding up, the pusher surface(s) 2429. The interaction of the second arms 2425b and the pusher surface(s) 2429 is schematically shown in FIG. 5B. As a result of the bell crank 2425 pivoting, the first arms 2425a thereof lift-up the fluid discharge device 2408 (arrow U, FIG. 4) by acting on the bearing surfaces 2433 of the embossments 2493 of the collar 2490. This results in compression of the pump (not shown) and release of a metered dose of the fluid, as an atomised spray, from the nozzle 2411.

It will be seen from FIG. 5B that each second arm 2425b in this embodiment has its own respective pusher surface 2429, and these act as guide rails for the contact surfaces 2428. However, it will be recognised that a single pusher surface 1429 could be provided for both contact surfaces 1428, if desired.

In this embodiment the bell crank 2425 has a generally inverted Y-shape with the first and second arms 2425a, 2425b forming the outer limbs and the mounting portion 2426 the inner limb. As shown, the mounting portion 2426 comprises a spindle 2426a for pivotal connection to the lever 2420

Moreover, in this embodiment a biasing force for the bell crank 2425 is provided by an elongate, flexible biasing element or spring 2425c which is in the form of a tail portion of the bell crank which extends away from the mid-point, or substantially the mid-point, of the spindle 2426a of the bell crank 2425. The biasing element 2425c has a plug 2425d at its distal (lower) end to plug into a complementary recess 2420b in the lever 2420. When the bell crank 2425 is mounted to the lever 2420, the biasing element 2425c biases the bell crank 2425 in the clockwise sense, as described above in relation to the first fluid dispensing device 1405. FIG. 5A includes an inset to show the connection of the bell crank 2425 to the lever 2420 through the spindle 2426a being clipped between a pair of resilient shelves 2420n, 2420p which project inwardly from the lever inner surface 2420d.

The biasing element 2425c may be an integrally or separately formed feature of the second member 2425.

The length of the biasing element 2425c may be made shorter than that shown. Alternatively, the biasing element 2525c may be omitted and replaced with a biasing element of the type described above for the first fluid dispensing device 1405 or hereinafter for a third fluid dispensing device 3405.

Although the finger-operable actuator mechanism 1415; 2415 of the first and second fluid dispensing devices 1405; 2405 is provided with a biasing force (leaf springs 1465; 2465) which biases the actuator mechanism 1415; 2415 to the rest position, this may be omitted and reliance placed on the return spring in the compression pump returning the actuator mechanism 1415; 2415 to its rest position on release of the actuating force F applied thereto.

The first and second fluid dispensing devices 1405; 2405 could, with minor modification, be used with different fluid discharge devices than described. For instance, a modified version of the second fluid dispensing device 2405 (herein the "third fluid dispensing device 3405") is shown in FIGS. 6A-E which incorporates a pump system, generally shown at 3408, as disclosed in International (PCT) patent application Nos. WO-A-2007/138084 and PCT/EP2008/056655, incorporated herein by reference, which pump system 3408 is described in Annex 1 of this description with reference to FIGS. 7 to 41 hereof. In the particular embodiment described with reference to FIGS. 6A-E, the pump system 3408 used is the "fluid dispenser 410" described in Annex 1 with reference to FIG. 32.

For expediency of describing the third device 3405, only the differences will be described in any detail, as recourse can be made to the description of the first and second fluid dispensing devices 1405; 2405 for the other features and attributes.

In the third fluid dispensing device 3405, the housing 3409 (e.g. made of ABS) corresponds closely to the housing 2409 of the second fluid dispensing device 2405, with a main exception being that most of the upper end is removed to provide a wide upper opening to receive the nozzle 416 of the pump system 3408.

Figure 6A:
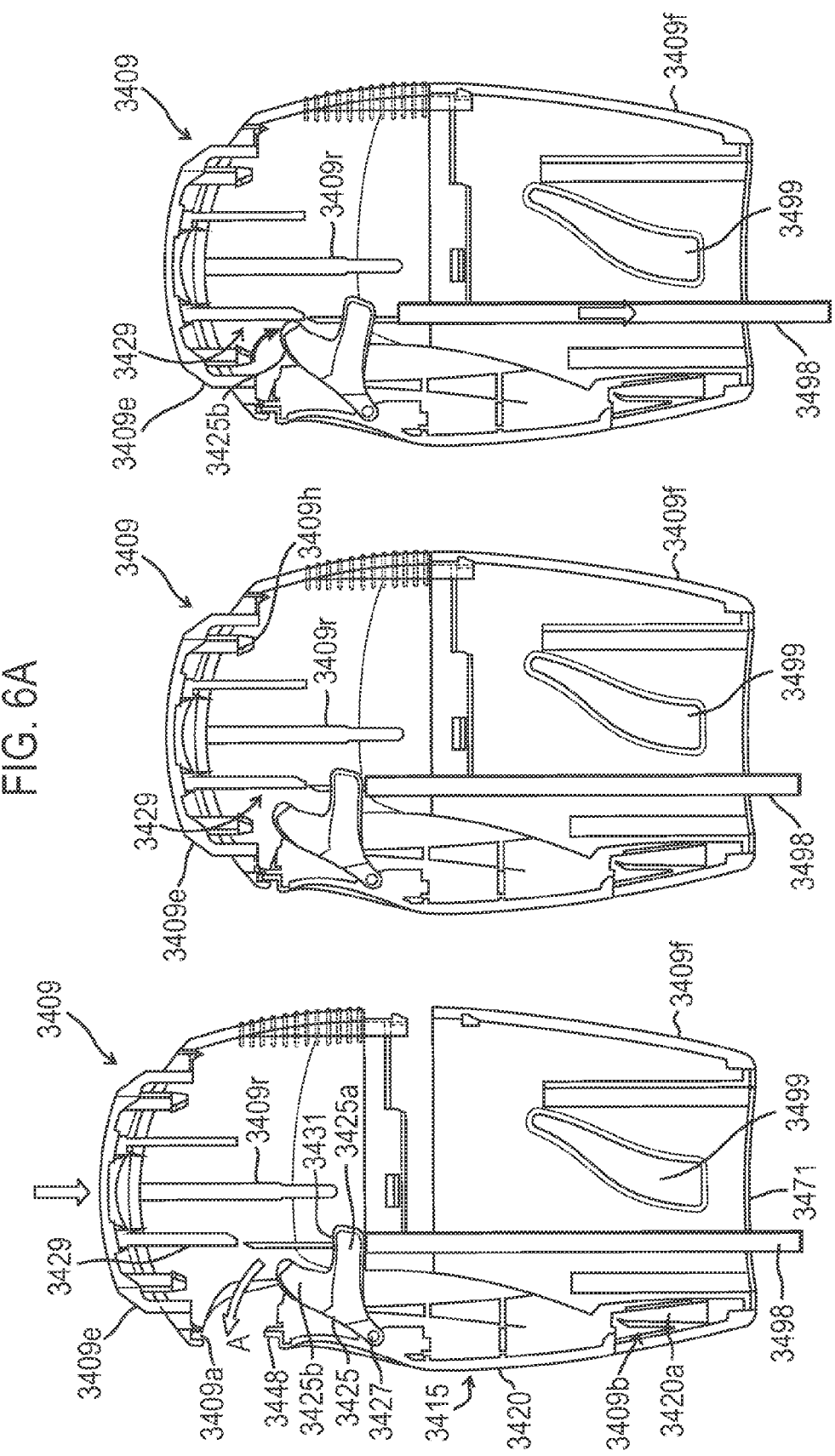

Referring to FIG. 6A, before the upper and lower housing halves 3409e, 3409f are snap-fitted together, the lower end 3420a of the lever 3420 (e.g. made of ABS) is inserted into the retaining channel 3409b formed in the lower housing half 3409f so that the finger-operable actuator mechanism 3415 is retained by the lower housing half 3409f. To ensure that the bell crank 3425 (e.g. made of acetal) is oriented correctly with reference to the pusher surfaces 3429 presented by the upper housing half 3409e after assembly of the housing 3409, a pusher 3498 in an assembly line apparatus pushes the bell crank 3425 to pivot anti-clockwise A against the clockwise biasing force while the housing halves 3409e, 3409f are snapped together. The pusher 3498 then releases the bell crank 3425 to enable the second arms 3425b to be biased by the biasing force into contact with the housing pusher surfaces 3429.

FIG. 6A also shows one of a pair of cut-out windows 3499 provided in opposing sides of the lower housing half 3409f through which the content of fluid in the fluid supply or container 470 of the pump system 3408 can be viewed, once the pump system 3408 is located in the housing 3409.

It will further be seen from FIG. 6A that the finger-operable actuator mechanism 3415 of the third fluid dispensing device 3405 does not have an elongate, flexible biasing element, such as that 2525c of the second fluid dispensing device 2405. Rather, the clockwise biasing force for the bell crank 3425 is provided by a torsion spring mounted at the pivot point 3427 of the bell crank 3425 on the lever 3420. In more detail, and referring to FIG. 6E, the mounting portion 3426 of the bell crank 3425 comprises a spindle 3426a for clipping to the lever 3420 (see FIG. 5A) and the clockwise biasing force is provided by a single torsion spring 3480 (e.g. of stainless steel, such as 304 or 316 grade) mounted on one end of the spindle 3426a. The torsion spring 3480 has a first spring leg 3480a, whose free end is formed into a hook 3480b to hook in a mounting hole 3425h in the bell crank 3425, and a second spring leg 3480c which bears against an inner surface 3420d of the lever 3420. This arrangement results in the first spring leg 3480a biasing the bell crank 3425 clockwise towards the downward position on the lever 3420 shown in ghost in FIG. 6E. Of course, when the actuator mechanism 3415 is mounted in the housing 3409, the pusher surfaces 3429 prevent the torsion spring 3480 biasing the bell crank 3425 to the ghost position.

Figure 7A:
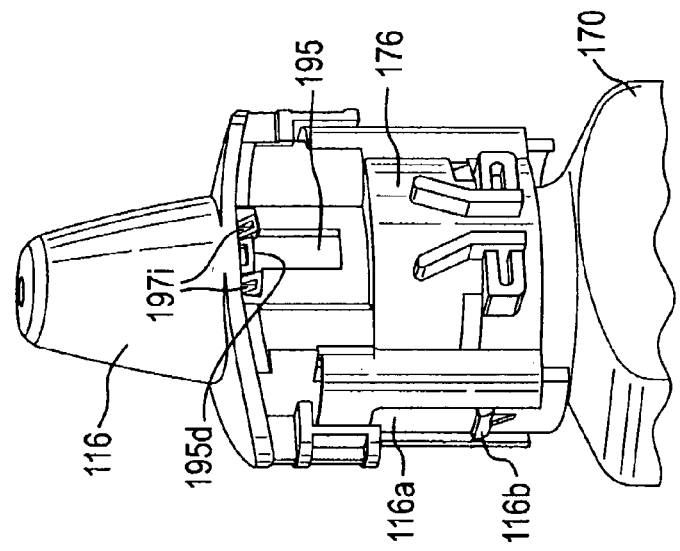
FIGS. 7A to 7C are perspective side views of a pump sub-assembly (hereinafter a "fluid dispenser") for use in the third to fifth fluid dispensing devices, where
Figure 7B:
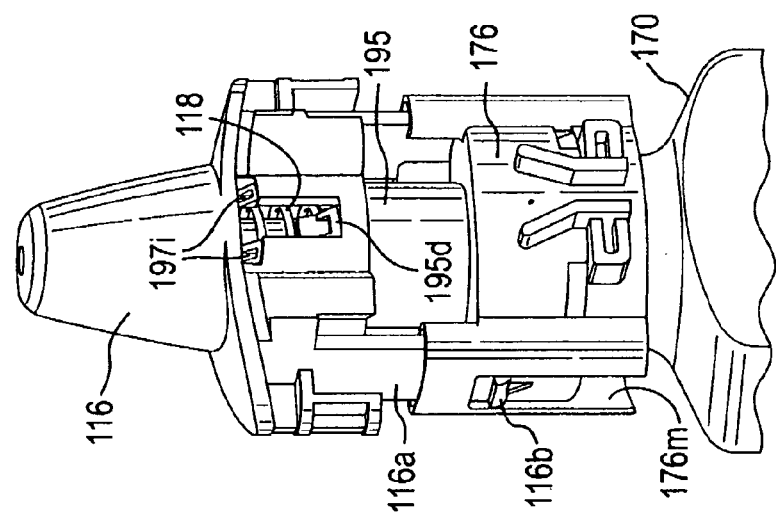
Figure 7C:
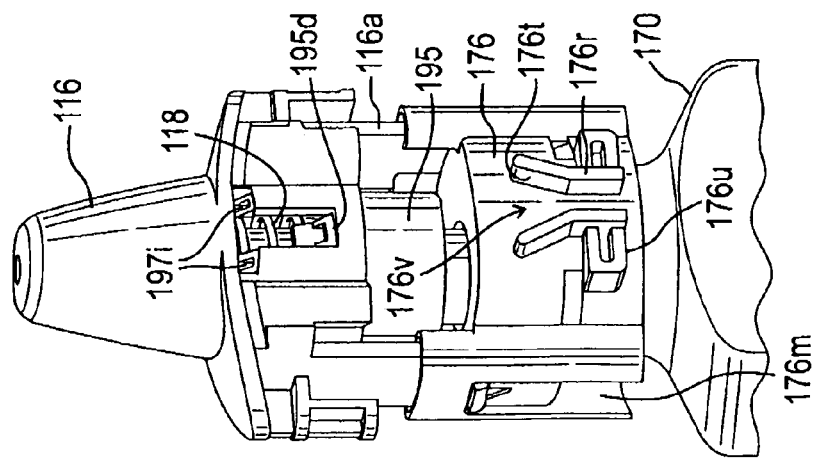

In the hand-held, hand-operable third fluid dispensing device 3405, the pump system 3408 forms a pump sub-assembly thereof, having a form as shown in FIGS. 7A-C, and the finger-operable actuator mechanism forms part of a hand-held, hand-operable actuator for actuating the pump system when received by the actuator (as is also the case for the other exemplary fluid dispensing devices described herein). As previously stated, the pump system/sub-assembly 3408 for the third fluid dispensing system is as shown in FIG. 32 (as described in Annex 1 in conjunction with FIGS. 7 to 31), but may be any one of the other specific pump systems described in Annex 1 with reference to FIGS. 7 to 41.

Figure 32:
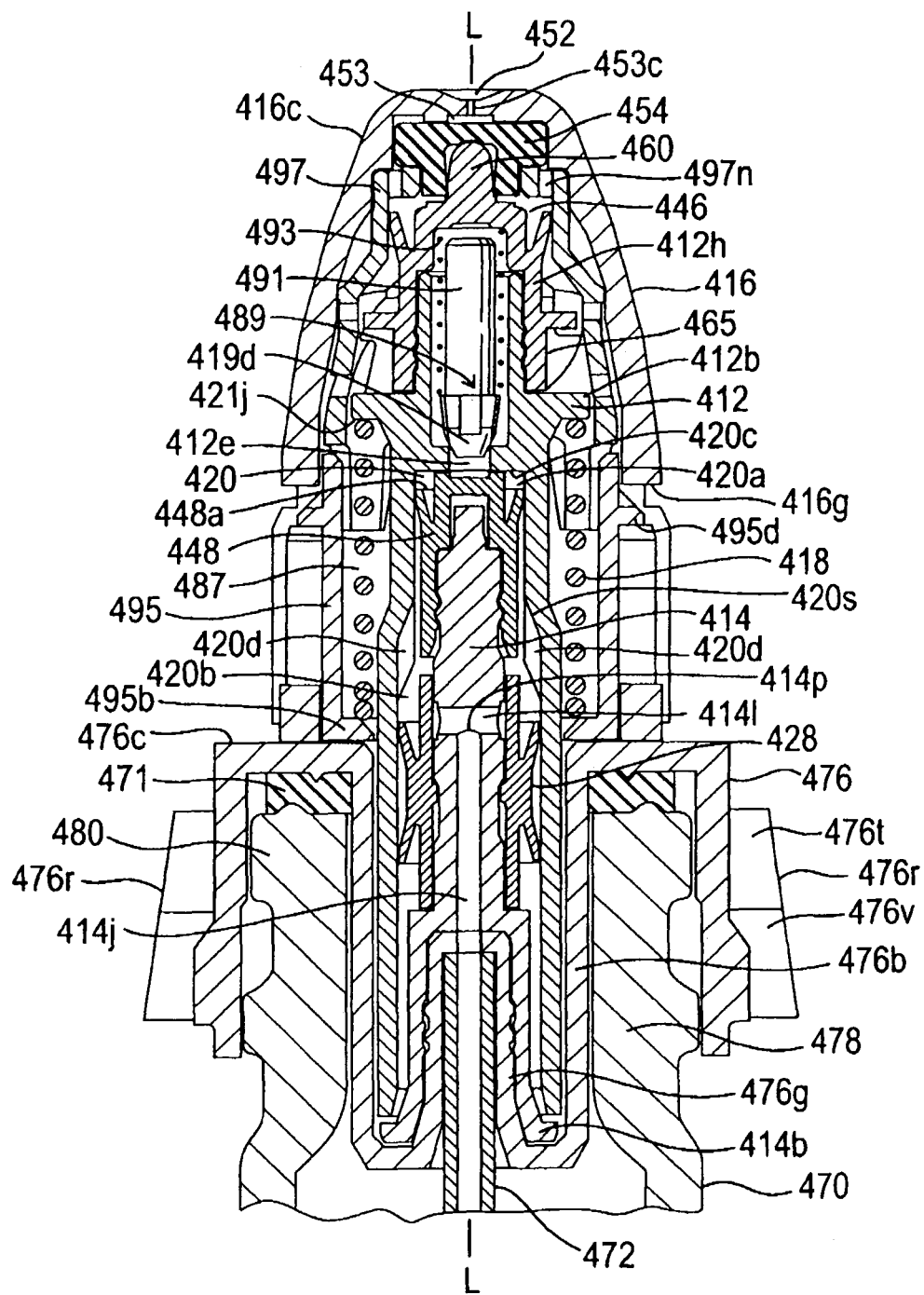
FIG. 32 is a cross-sectional side view of another modified version of the fluid dispenser of FIGS. 7 to 21 for use in the third to fifth fluid dispensing devices, the modified version being shown in its fired position, but as viewed in a section taken perpendicular to that in FIGS. 9A to 9C.

Notably, the stopper portion 476 of the pump sub-assembly 3408 provides the pair of diametrically-opposed embossments 476r, each having (i) the track 476v and lead-in surface 476t for the complementary runners 3409r in the housing 3409 (see FIG. 6A), and (ii) the bearing surface 476u for the lifting surface 3431 of each first arm 3425a of the bell crank 3425 to act on to move the pump sub-assembly 3408 from its rest position (FIG. 6D) to its fired position (FIG. 32).

Figure 6D:
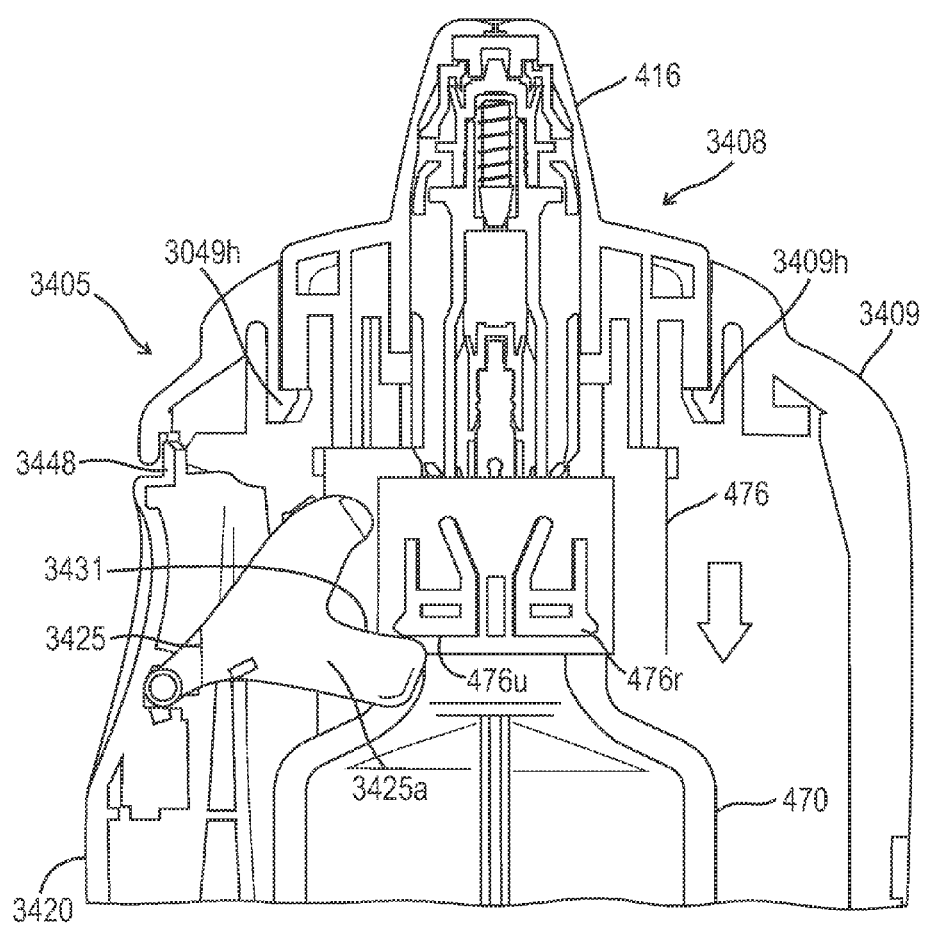
Figure 6E:
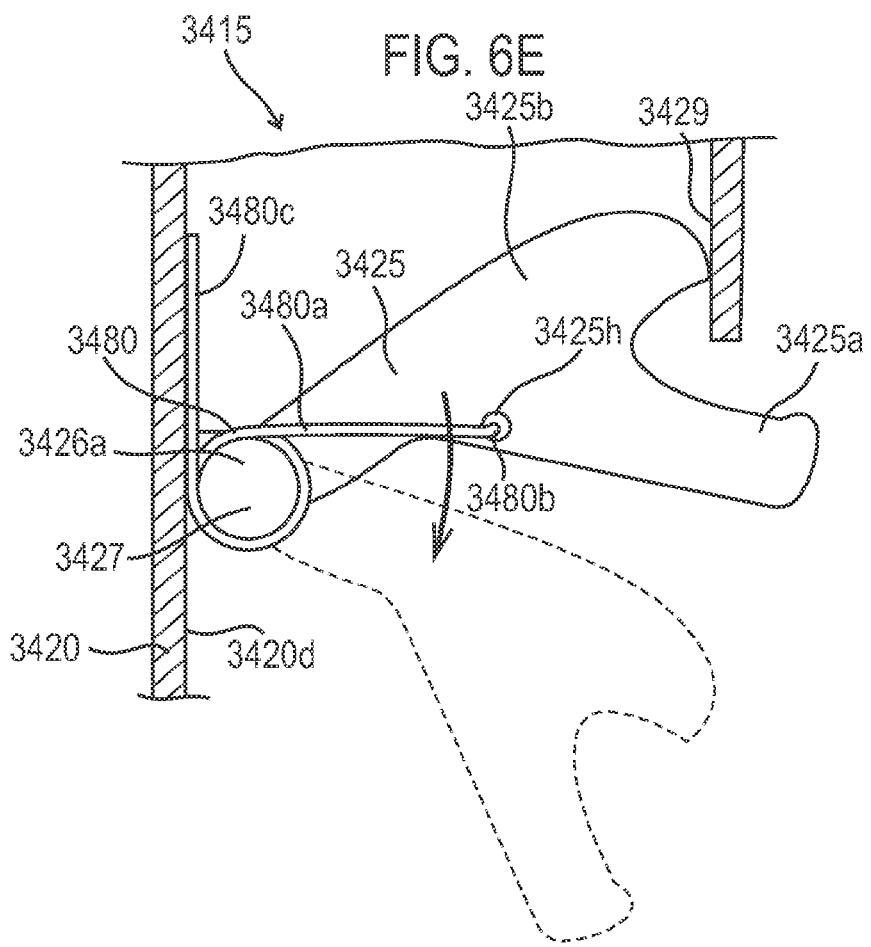
FIG. 6E is a schematic side view of the actuator mechanism of the third fluid dispensing device.

As will be understood from FIGS. 6B-D, after the housing halves 3409e, 3409f are assembled, the pump sub-assembly 3408 is inserted into the housing 3409 through the lower opening 3471 (FIG. 6A) until the nozzle 416 is received in the upper opening and snap-fits in the housing 3409 (see FIG. 6C). As will be seen from FIG. 6C, the housing 3409 has resilient clips 3409h to engage the nozzle 416 so as to hold to nozzle 416 against moving in the opposite axial direction to insertion. To limit the axial insertion of the nozzle 416 in the housing 3409, the nozzle 416 is provided with a series of protrusions (feature 116p on identical nozzle 116 in FIG. 16A) on opposing sides thereof which abut the underside of the upper end of the housing 3409 when the clips 3409h engage the nozzle 416. As a result, the nozzle 416 is fixed against movement relative to the housing 3409.

FIGS. 6B-D also show that as the pump sub-assembly 3408 moves towards the upper end of the housing 3409, a shoulder 416d and outer skirt 416s of the nozzle 416 successively push on the underside of the bell crank 3425 so that the bell crank 3425 pivots anti-clockwise A so as not to impede insertion of the pump sub-assembly 3408 to the position where it snap-fits in the housing 3409.

As will be understood from FIG. 6C, when the pump sub-assembly 3408 is snap-fitted to the housing 3409, the torsion spring 3480 returns the bell crank 3425 to its orientation where the second arms 3425b engage the pusher surfaces 3429 and the first arms 3425b are disposed below the embossments 476r of the stopper portion 476. The provision of the biasing force also means this would happen in the event the assembly of the pump sub-assembly 3408 into the housing 3409 was carried out upside-down.

Prior to assembling the pump sub-assembly 3408 into the housing 3409, the sub-assembly 3408 is either in its fully extended (see FIGS. 7A and 9A) or rest (see FIGS. 7B and 9B) position. Irrespectively, as shown in FIGS. 6B and 6C, the pump sub-assembly 3408 is moved to its fired position (see also FIG. 32) during insertion into the housing 3409 by an insertion force I applied thereto by the assembly line apparatus to insert the pump sub-assembly 3408. As shown in FIG. 6D, when the pump sub-assembly 3408 is snap-fitted into the housing 3409, the insertion force I is removed and the pump sub-assembly 3408 is restored to its rest position (as in FIGS. 7A and 9B) by the return spring 118, meaning that the stopper portion 476 moves away from the captive nozzle 416 (i.e. towards the housing lower open end 3471). Recalling from FIG. 6C that the bell crank 3425 has already pivoted back to its rest position against the pusher surfaces 3429, the subsequent return movement of the stopper portion 476 brings the bearing surfaces 476u of the embossments 476r of the stopper portion 476 into engagement with, or into close proximity to, the associated lifting surfaces 3431 of the first arms 3425a of the bell crank 3425, as shown in FIG. 6D. This is the "ready-to-use" state of the third fluid dispensing device 3405, notwithstanding that counterparts of the protective end cap (e.g. 1407, FIG. 1) and lower end cap (e.g. 1472, FIG. 1) of the previous embodiments would still ordinarily be mounted to the device 3405 prior to distribution of the device 3405 to a user.

To operate the third fluid dispensing device 3405, the user removes the protective end cap and actuates the pump sub-assembly 3408 by moving the finger-operable actuator mechanism 3415 inwardly, so that the bell crank 3425 pivots anti-clockwise A to lift up the stopper portion 476 along the longitudinal axis L-L (see FIG. 32; equivalent of axis X-X in FIGS. 1 to 4 and, hence, again corresponds to the housing axis) and so move the pump sub-assembly 3408 from its rest position (FIG. 6D) to its fired position (FIG. 32). The user then releases the inward force F on the actuator mechanism 3415 so that the pump return spring 418 (FIG. 32) resets the pump sub-assembly 3408 and actuator mechanism 3415 to their respective rests positions shown in FIG. 6D.

For first usage of the third fluid dispensing device 3405, this device operation is repeated until the pump sub-assembly 3408 is primed, as described in Annex 1 with reference to FIGS. 22A-J. Thereafter, the next device operation results in a metered dose of the fluid (liquid) medicament in the container 470 of the pump sub-assembly 3408 being discharged from the fluid outlet 452 as an atomised spray, as also described in Annex 1. The atomised spray in this particular embodiment is delivered to the nasal cavity of the user (self-administration) or someone else incapable of self-administration. The device operations continue in accordance with the prescribed dosing regime for the liquid medicament until no more liquid medicament is able to be dispensed. At the end of each dosing event, where the required number of doses in the dosing regime are delivered to the nasal cavity, the protective end cap is replaced on the housing 3409 until the next scheduled dosing event. The protective end cap prevents inadvertent device operation by blocking inward movement of the tab 3448 on the lever 3420, as in the other devices 1405; 2405 described before.

Figure 6F:
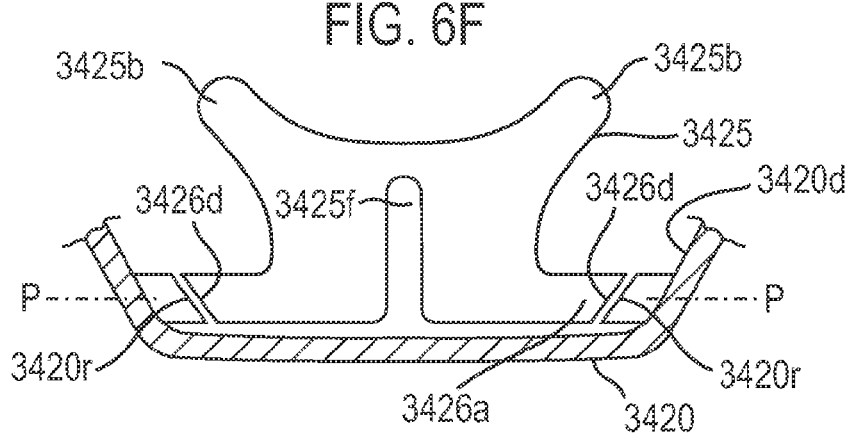
FIG. 6F is a schematic plan view of an alternative actuator mechanism in accordance with the present invention.

In the third fluid dispensing device 3405, the torsion spring 3480 could be replaced with another biasing mechanism to provide the biasing force on the bell crank 3425, such as described for the first and second devices 1405; 2405. Another alternative biasing mechanism is shown in FIG. 6F, which is a schematic, part-sectional plan view of the bell crank 3425 mounted to the lever 3420. The free ends of the crank spindle 3426a are formed into cam faces 3426d defining an oblique angle with respect to the pivot axis P-P through the spindle 3426a. Complementary cam faces 3420r are provided by the lever 3420 against, or in close proximity to, the cam faces 3426d. As will be understood, when the bell crank 3425 pivots upon inward movement of the lever 3420, one or other of the cam faces 3426d, 3420r will need to be deflected away from the cam interface to allow the complementary cam faces 3246d, 3420r to move over one another. If the bell crank 3425 and/or the lever 3420 are adapted to provide resiliency to the associated cam faces 3426d, 3420r (e.g. by material and/or design), then this provides a biasing force to bias the bell crank 3425 towards the ghost position on the lever 3420 shown in FIG. 6E. In this particular embodiment, the bell crank 3425 is provided with a cut-out 3425f which intersects the spindle 3426a so as to allow the spindle 3426a to compress when it pivots about pivot axis P-P and load-up therein a biasing force which pivots the bell crank backwards on release of the pivoting force. This biasing mechanism could also be used in the first and/or second fluid dispensing device 1405; 2405.

In the third fluid dispensing device 3405 no biasing force is provided in the finger-operable actuator mechanism 3415 to bias the actuator mechanism 3415 to the rest position, unlike in the versions of the first and second devices 1415; 2415, which have the leaf spring 1465; 2465. Rather, the return spring 418 in the pump sub-assembly 3408 biases or returns the actuator mechanism 3415 to its rest position, e.g. on release of the actuating force F applied to the actuator mechanism 3415.

If the third fluid dispensing device 3405 is dropped, or subject to other impacts, so as to cause the pump sub-assembly 3408 to move to its fully extended (open) position (e.g., as described in Annex 1 in conjunction with FIGS. 7A and 9A), when the stopper portion 476 moves farther away from the nozzle 416 the embossments 493r force the bell crank 3425 to pivot clockwise and thereby force the actuator mechanism 3415 to 'pop-out' of the housing 3409 to the outward position discussed in relation to the first and second devices 1405; 2405. The relatively high outwardly-directed force exerted on the actuator mechanism 3415 in such an event causes the resilient tab 3448 at the upper end of the lever 3420 to deflect inwardly to allow the lever to 'pop-out' to its outward position. However, the user can simply deflect the tab 3448 inwardly and push the lever 3420 back into the housing 3409 to its rest position so that the tab 3448 reengages the inner surface of the slot 3409a and, more especially, the bell crank 3425 resumes its rest position and in so doing lifts up the stopper portion 476 to reset the pump sub-assembly' 3408 to its rest position. This is because the bell crank 3425 is biased to its ghost position of FIG. 6E when in its outward position, so the first arms 3425a are able to re-enter the housing 3409 under the embossments 476r and lift them up when the pusher surfaces 3429 cause the bell crank 3425 to pivot when they push on the second arms 325b.

In the third fluid dispensing device 3405, the lever tab 3448 is not used to hold the actuator mechanism 3415 in its outboard position for assembly of the pump sub-assembly 3408 into the housing 3409, since this is not necessary (although it could be so used, if desired). Rather, the lever tab 3448 simply acts as a latch to latch the actuator mechanism 3415 in the housing 3409.

Figure 6G:
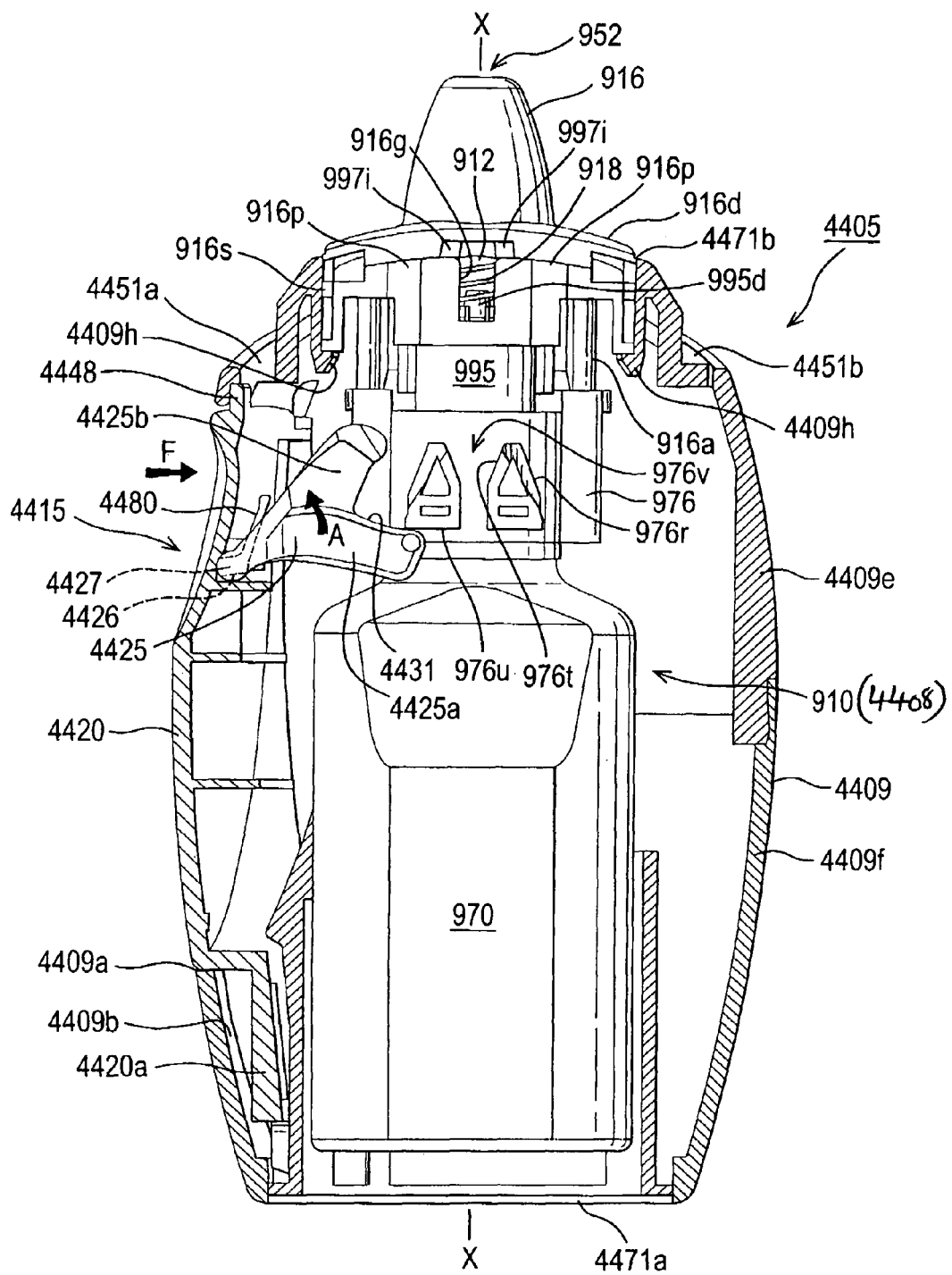
FIG. 6G is side view, partly in cross section, of a fourth fluid dispensing device in accordance with the present invention.
Figure 6H:
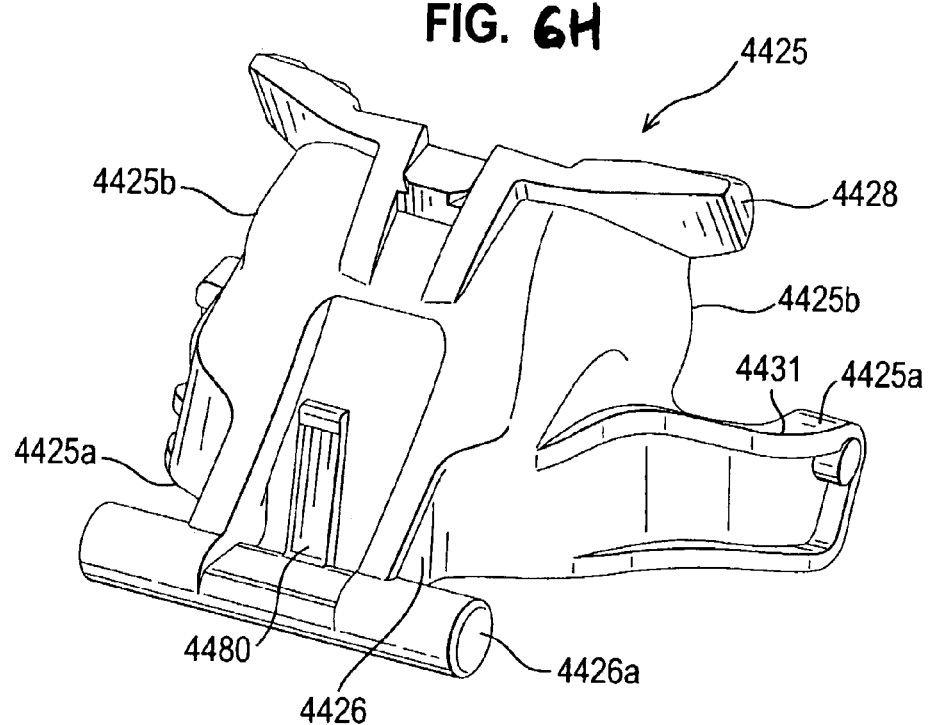
FIGS. 6H and 6I are perspective views of the bell crank of the fourth fluid dispensing device.
Figure 6I:
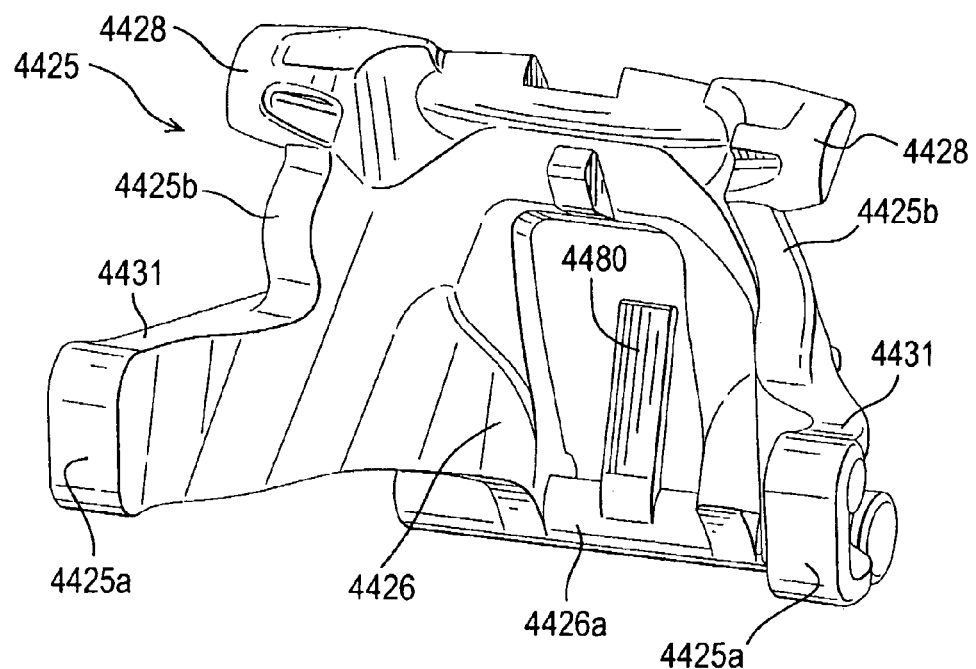

In FIG. 6G, there is shown a hand-held, hand-operable fourth fluid dispensing device 4405 which is a modified form of the third fluid dispensing device 3405, with like reference numerals denoting like features. In particular, the fourth fluid dispensing device 4405 comprises a subtly different finger-operable actuator mechanism 4415, of which component parts are shown in FIGS. 6H to 6K The pump sub-assembly 4408 may be as in the third fluid dispensing device 3405, and for ease of reference the features thereof are identified in FIG. 6H with reference numerals like those used in Annex 1 to describe the assemblies ("fluid dispensers") in FIGS. 7 to 41. Thus, the pump sub-assembly 4408 is also denoted by reference number 910 in FIG. 6H for consistency with the numbering for the pump sub-assemblies in FIGS. 7 to 41. The pump sub-assembly 4408 will hereinafter be referred to as "fluid dispenser 910".

The actuator mechanism 4415 in the fourth device 4405 actuates the fluid dispenser 910 in the same manner as the actuator mechanism 3415 of the third device 3405, so will not be described again.

In this embodiment, the bell crank 4425 is integrally formed with a spring 4480, here a spring leg, in place of the torsion spring 3480. The spring leg 4480 projects from the spindle 4426a. As regards the lever 4420, which may be made from Teluran® ABS, this does not have a spring element (cf. spring element 1465, FIG. 1). Moreover, the tab 4448 is solid, so does not permit the lever 4420 to have an "outward position", as described, for instance, for the first fluid dispensing device 1405. The lever tab 4448 simply stops the lever 4420 moving out of the slot 4409a and cooperates with the protective end cap lug (not shown) to prevent inadvertent operation of the device 4405 when the cap is attached to the housing 4409. As will be appreciated from FIG. 6J, the spindle 4426a of the bell crank 4425 is clipped to a bracket 4220q presented on the inner surface 4220d of the lever 4220 for pivotal movement thereon.

The assembly of the fourth device 4405 is essentially as previously described for the third device 3405. However, when the bell crank 4425 is pivoted anti-clockwise A towards the nozzle 916 on insertion of the fluid dispenser 910 into the housing 4409, the spring leg 4480 is brought into engagement with the inner surface 4420d of the lever 4420 so as to be loaded. Once the embossments 976r on the stopper portion 976 pass the first arms 4425a of the bell crank 4425, the loading in the spring leg 4480 is released to pivot the bell crank 4425 back so that the first bell crank arms 4425a are disposed underneath the embossment bearing surfaces 976u and the second bell crank arms 4425b bear on the housing pusher surfaces 4429. Recalling that the fluid dispenser 910 is moved to its fired position during its insertion into the housing 4409, once the insertion force is removed when the fluid dispenser 910 is snap-fitted into the housing 4409, whereby the return spring 918 moves the fluid dispenser 910 back to its rest position, the bearing surfaces 976u of the embossments 976r of the stopper portion 976 are brought into engagement with, or into close proximity to, the associated lifting surfaces 4431 of the first arms 4425a of the bell crank 4425, as shown in FIG. 6G. Inward movement of the lever 4420 would now cause the bell crank 4425 to lift the fluid dispenser 910 to its fired position.

If the actuator 4405 is dropped, or subject to other impacts, so as to cause the fluid dispenser 910 to move to its fully extended (open) position, when the stopper portion 976 moves farther away from the nozzle 916 the embossments 976r force the bell crank 4425 to distort, since the lever 4420 cannot move outwardly due to the lever tab 4448. In more detail, the first or lifting arms 4425a of the bell crank 4425 are forced to flex rearwardly due to the rearward force applied thereto by the embossments 976r. This keeps the bell crank lifting arms 4425a in engagement with the respective embossment bearing surfaces 976u, whereby simply pushing the lever 4420 inwardly will lift the fluid dispenser 910 back to its rest position.

The fluid dispensing devices 1405;2405;3405;4405 may be modified to have another corresponding actuator mechanism (not shown) on the other side of the housing, as is the case for the fifth fluid dispensing device 5405 in accordance with the present invention shown in FIGS. 6L and 6M, where again like reference numerals denote like features. The user squeezes the levers 5420 together and in so doing causes the associated bell cranks 5425 to act on respective pusher surfaces (not shown) and the embossments 576r on the stopper portion 576 to lift the pump sub-assembly 510 (see FIG. 33) forwardly from each side thereof to its fired position. Where twin actuator mechanisms are used, a revised housing shape is needed compared to that used for the single actuator mechanism, such as shown in FIG. 6M.

The finger-operable actuator mechanisms, and actuators comprising the finger-operable actuator mechanisms, described herein provide for ease of assembly of the fluid dispensing device, and also enable the fluid dispensing device to have a compact size. Moreover, the first and second members of the finger-operable actuator mechanism could be integrally moulded, if desired.

Those parts of the fluid dispensing devices herein described which are made from a plastics material are typically formed by a moulding process, and more typically by injection moulding.

It will be appreciated that the present invention is not restricted to pump-based container systems, but could equally work with valved container systems, e.g. aerosol containers with metering valves, such as used in pressurised metered dose inhalers (oral and nasal pMDIs), since both container systems need to be compressed to effect dispensement therefrom (e.g. depression of the pump/valve into the associated container). Of course, for oral administration, the nozzle would be formed as a mouthpiece.

The fluid dispensing device of the invention may be used to dispense a fluid (typically a liquid) medicament formulation for the treatment of mild, moderate or severe acute or chronic symptoms or for prophylactic or palliative treatment. The precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

Appropriate medicaments for the formulation may be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α,9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino]propanoic acid (e.g. as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α,9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α,9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

Other medicaments which may be comprised in the formulation are 6-({3-[(Dimethylamino)carbonyl]phenyl}sulfonyl)-8-methyl-4-{[3-(methyloxy) phenyl]amino}-3-quinolinecarboxamide; 6a,9a-Difluoro-11b-hydroxy-16a-methyl-17a-(1-methycyclopropylcarbonyl)oxy-3-oxo-androsta-1,4-diene-17b-carbothioic acid S-fluoromethyl ester; 6a,9a-Difluoro-11i-hydroxy-16a-methyl-3-oxo-17α-(2,2,3,3-tetramethycyclopropylcarbonyl)oxy-androsta-1,4-diene-17i-carbothioic acid S-cyanomethyl ester; 1-{[3-(4-{[4-[5-fluoro-2-(methyloxy)phenyl]-2-hydroxy-4-methyl-2-(trifluoromethyl)pentyl]amino-6-methyl-1H-indazol-1-yl)phenyl]carbonyl}-D-prolinamide; and the compound disclosed in International patent application No. PCT/EP2007/053773, filed 18 Apr. 2007, in Example 24, and in particular the form which is 24C therein.

The fluid dispensing device of the invention may be used for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 μg, 50 μg, 100 μg, 200 μg or 250 μg of active medicament. The precise dosage is either known or readily ascertainable by those skilled in the art.

The embodiments of the invention hereinbefore described with reference to the accompanying Figures of drawings may be varied or modified in numerous ways within the scope of the invention and/or as expressly foreshadowed by the statements in the 'Summary of the Invention' supra and/or the claims infra. For instance, the pump system may be offset to give more space and allow greater travel of the first member or lever in the actuation direction, thereby reducing the user force needed to be applied to the first member or lever to actuate the device by giving greater mechanical advantage.

Annex 1

FIGS. 7 to 21 show a pump system (hereinafter the "fluid dispenser 110") whose underlying principle of operation is as described in US-A-2005/0236434 and WO-A-2005/075103, hereby incorporated herein by reference, in this instance for dispensing a metered dose of a liquid containing a medicament, for example suspended or dissolved in the liquid.

Figure 9A:
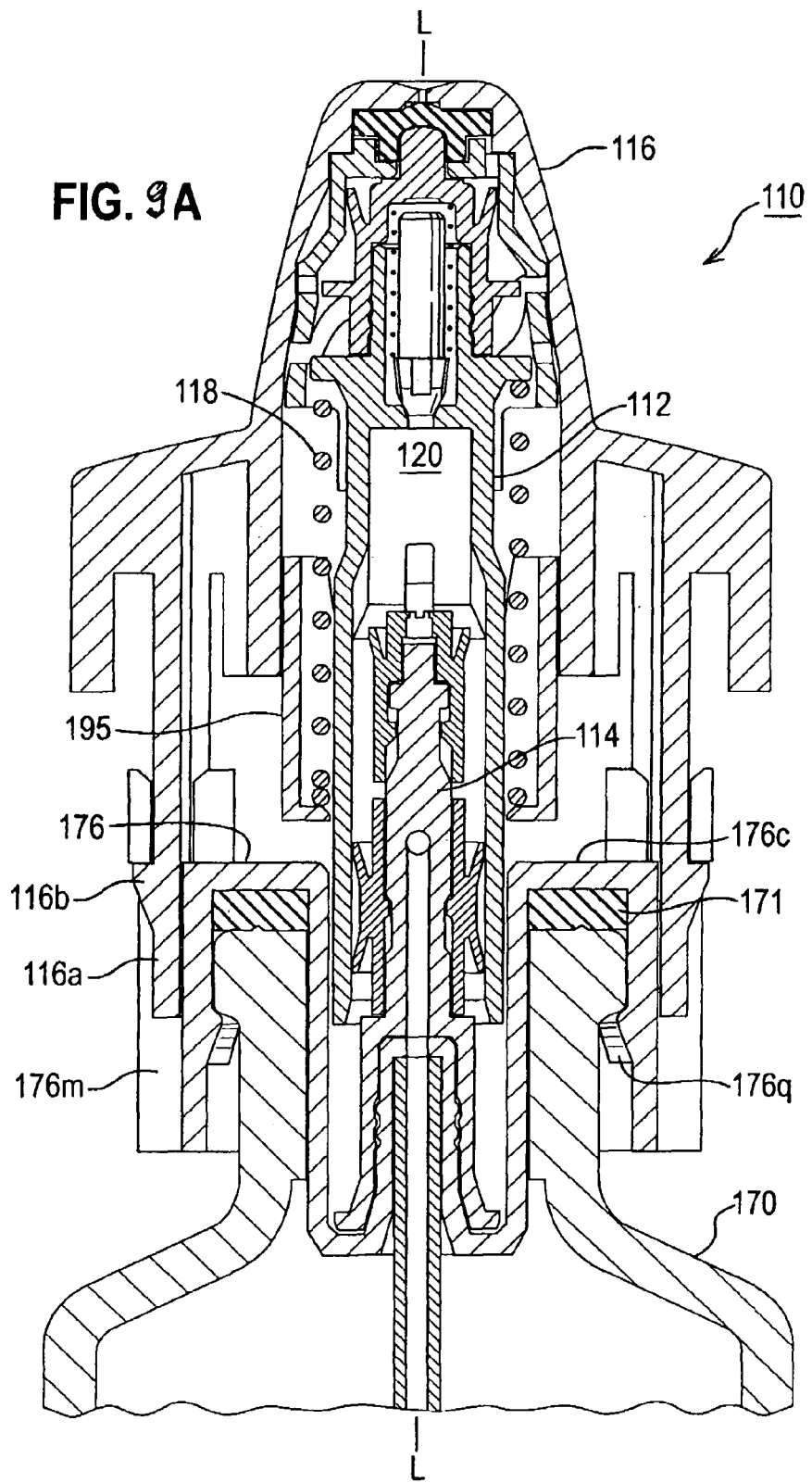
Figure 9B:
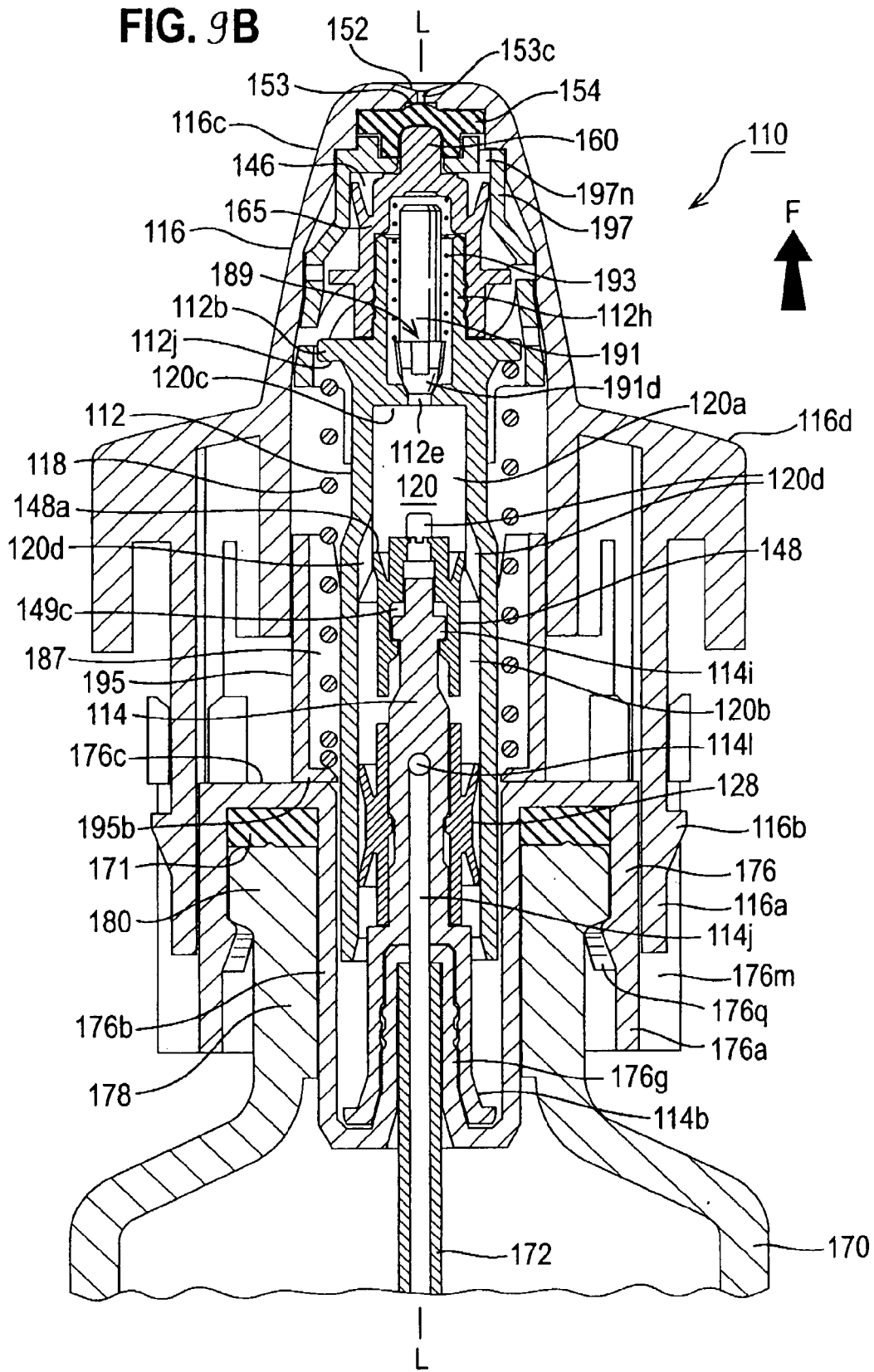
Figure 11A:
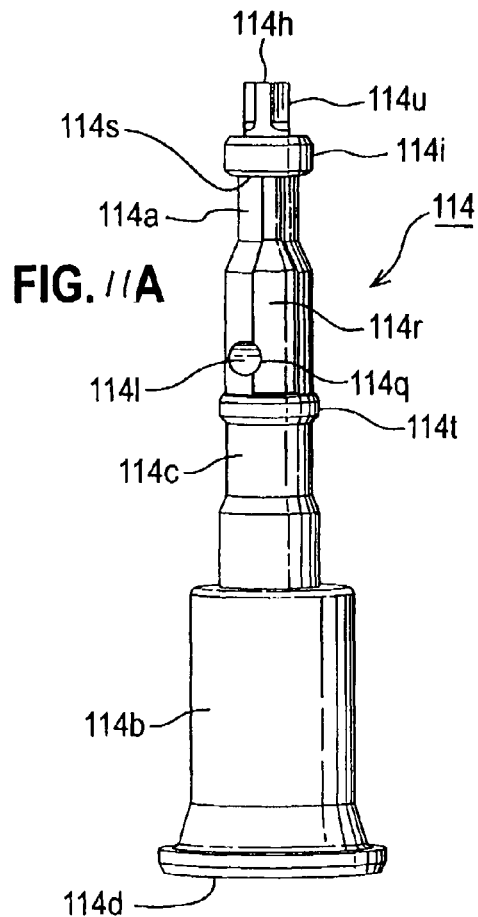
FIGS. 11A and 11B are respectively side views and cross-sectional side views of a piston member of the fluid dispenser of FIGS. 7 to 10.
Figure 11B:
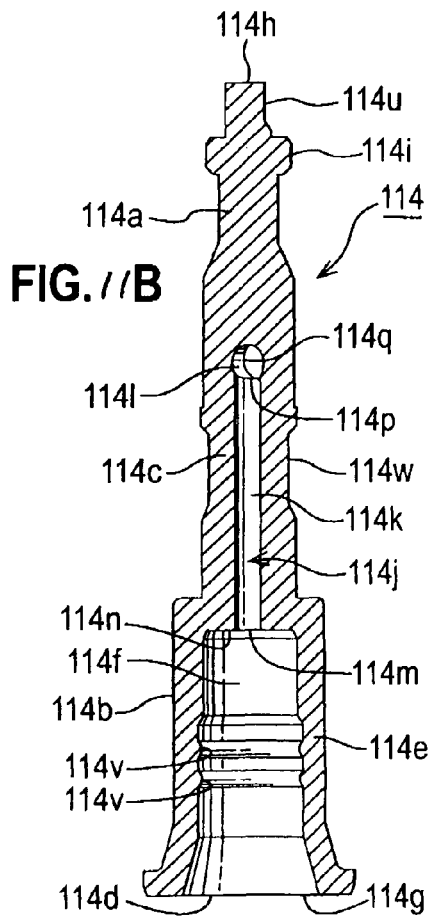
Figure 12:
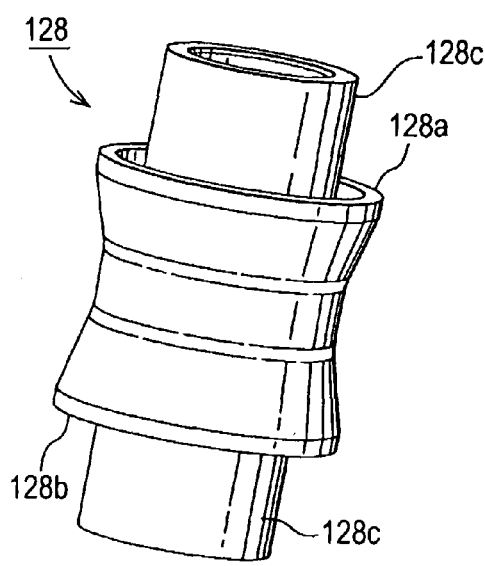
FIGS. 12A and 12B are respectively perspective and cross-sectional side views of a rear sealing element of the fluid dispenser of FIGS. 7 to 10 which mounts on the piston member of FIGS. 11A-B.
Figure 12:
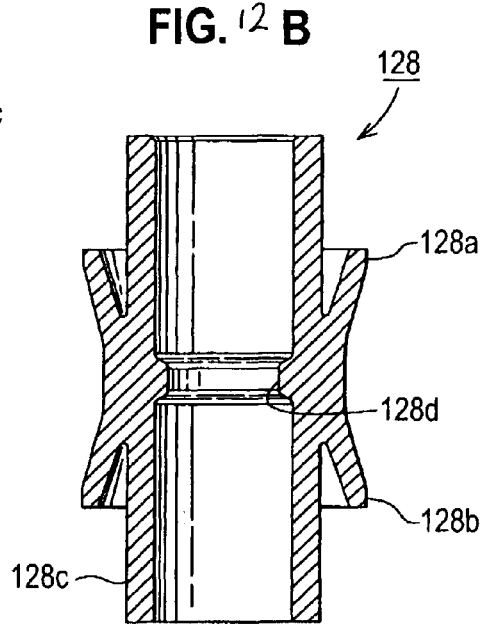

Referring to FIGS. 9B, 11A and 11B, the piston member 114 of the fluid dispenser has a generally cylindrical form and is mounted to stroke in reciprocal fashion along a longitudinal axis L-L of the fluid dispenser 110 inside the dosing chamber 120 defined by the main housing 112. The piston member 114 is mounted to stroke between forward and rear positions relative to the dosing chamber 120. As a piston, it will impose a pumping force onto fluid within the dosing chamber 120 as the piston member 114 moves within the dosing chamber 120.

The piston member 114 is injection moulded from polypropylene (PP), but other functionally equivalent plastics materials could be used.

Figure 14A:
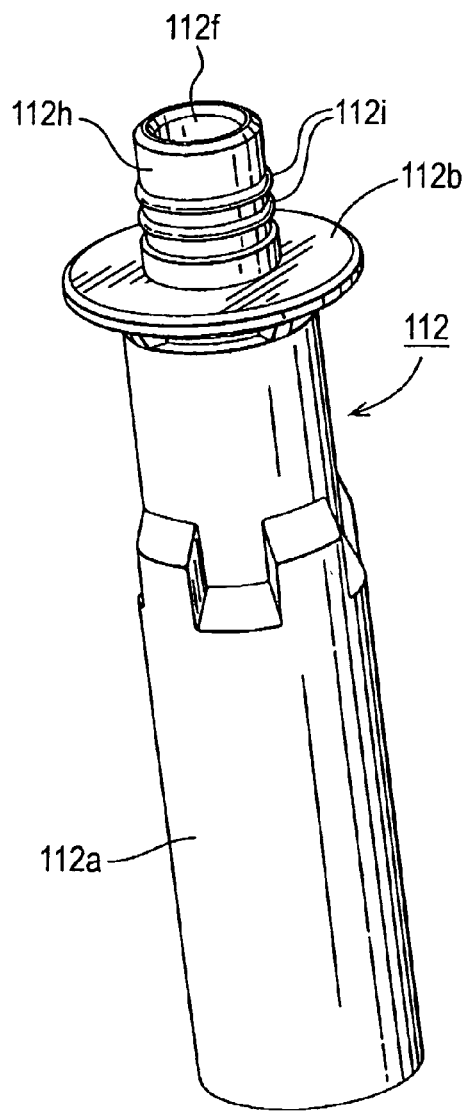
FIGS. 14A and 14B are respectively perspective and cross-sectional side views of a main housing of the fluid dispenser of FIGS. 7 to 10 which slidingly receives the piston member of FIGS. 11A-B.
Figure 14B:
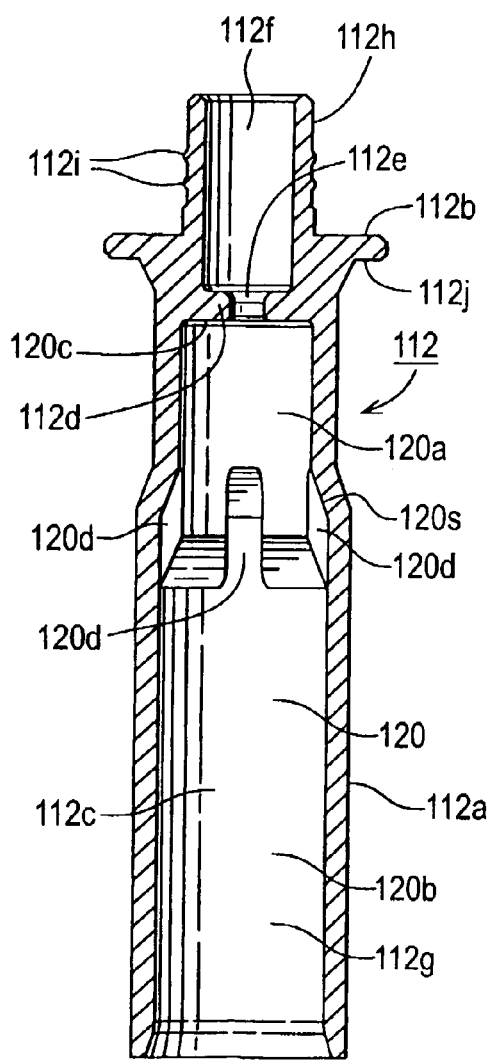

As shown in FIGS. 14A and 14B, the main housing 112 is formed by a tubular body 112a from which an annular flange 112b projects. The tubular body 112a has an open-ended axial bore 112c into which an annular shoulder 112d projects to create a restricted bore section 112e relative to forward and rear bore sections 112f, 112g disposed on either side of the annular shoulder 112d. The rear bore section 112g defines the dosing chamber 120. The forward section 112h of the tubular body 112a is provided with a pair of outer circumferential beads 112i, the purpose of which will be explained shortly hereinafter.

The main housing 112 in this embodiment is injection moulded from polypropylene (PP), but other plastics materials could be used.

Referring to FIGS. 9B, 9C, 14A and 14B, the dosing chamber 120 is cylindrical and co-axially arranged with the longitudinal axis L-L. The dosing chamber 120 has forward and rear sections 120a, 120b. As can be seen, the forward section 120a is narrower than the rear section 120b. A step 120s tapers inwardly in the forward direction F (see FIG. 14B) to connect the rear section 120b to the forward section 120a. As shown in FIGS. 9B and 14B, at least one axial groove or flute 120d is formed in the step 120s. In this particular embodiment, four such flutes 120d are provided, although another number may be selected. Where plural flutes 120d are provided, they are ideally equi-angularly spaced apart, as in this particular embodiment.

The forward section 120a forms a metering chamber which meters a volume of the fluid for dispensement from the dispenser 110. The metered volume may be 50 microlitres, but this is only illustrative as the fluid dispenser 110 can be arranged to dispense the desired metered volume.

Turning back to FIGS. 11A and 11B, the piston member 114 has a forward section 114a, a rear section 114b and a central section 114c. These are arranged co-axially.

The rear section 114b presents the open rear end 114d of the piston member 114. The rear section 114b is cup-shaped having an annular outer peripheral wall 114e which defines an internal cavity 114f having a mouth 114g which opens in the rear end 114d.

The forward section 114a is solid and presents the forward end 114h of the piston member 114. The forward section 114a comprises an annular flange 114i rearwardly of the forward end 114h.

The central section 114c connects to the forward and rear ends 114a, 114b and comprises an internal bore network 114j to place the rear section 120b of the dosing chamber 120 in fluid communication with the fluid supply 170 (a bottle, e.g. of glass, such as 1430; 2430—respectively, FIGS. 1 and 3), as will be described in more detail hereinafter. The bore network 114j consists of an axial section 114k and plural transverse sections 114l. The axial bore section 114k extends forwardly from a rear opening 114m in a forward face 114n of the internal cavity 114f to a junction 114p. The transverse bore sections 114l extend transversely, inwardly from respective forward openings 114q in the outer circumferential surface of the central section 114c to the junction 114p to connect with the axial bore section 114k. The forward openings 114q are arranged equi-angularly about the central section 114c. In this particular embodiment, there are two transverse bore sections 114l, but one or greater than two transverse bore sections could be used. The forward openings 114q are also recessed in the central section 114c.

The piston member 114 is provided with a plurality of axially-oriented grooves 114r about the outer periphery. The grooves 114r extend rearwardly from a rear surface 114s of the annular flange 114i in the forward section 114a to an annular rib 114t on the central section 114c rearward of the forward openings 114q of the internal bore network 114j. The grooves 114r are arranged so that at least a portion of the forward openings 114q are within the grooves 114r.

The tip part 114u of the forward section 114a of the piston member 114, which extends forwardly from the flange 114i to the forward end 114h, has a triangular cross-sectional shape, with the apexes being rounded.

Referring to FIGS. 9B, 9C, 12A and 12B, the piston member 114 carries on its central section 114c a tubular rear sealing element 128 which provides a permanent dynamic (sliding) seal between the piston member 114 and the rear section 120b of the dosing chamber 120. The rear sealing element 128 is fixed to the piston member 114 to move in unison therewith so that there is no, or substantially no, relative axial movement therebetween as the piston member 114 strokes in the dosing chamber 120.

The rear sealing element 128 is of the lip-seal type, being provided with resilient, annular sealing lips 128a, 128b at its forward and rear ends, respectively. The material of the rear sealing element 128 provides the sealing lips 128a, 128b with an inherent outwardly-directed bias. The sealing lips 128a, 128b have an outer diameter which is greater than the inner diameter of the rear dosing chamber section 120b, whereby the sealing lips 128a, 128b are compressed inwardly by the inner surface of the rear dosing chamber section 120b. As a result, the bias in the sealing lips 128a, 128b means they sealingly engage the inner surface of the rear dosing chamber section 120b.

The rear sealing element 128 further comprises a tubular body 128c from which the sealing lips 128a, 128b depend and which fits on the outer surface of the piston member central section 114c by engagement of an inner circumferential bead 128d of the rear sealing element 128 in a recessed portion 114w of the central section 114c of the piston member 114. The tubular body 128c has a length such that, when fitted on the piston member 114, it covers substantially the entire axial extent of the central section 114c of the piston member 114. It will further be seen from FIG. 9B that the rear end of the rear sealing element 128 bears against the forward end of the rear section 114b of the piston member 114, as a result of which the circumferential bead 128 is disposed at the forward end of the recessed portion 114w. This arrangement prevents, or substantially prevents, relative axial movement of the rear sealing element 128 on the piston member 114.

Figure 13A:
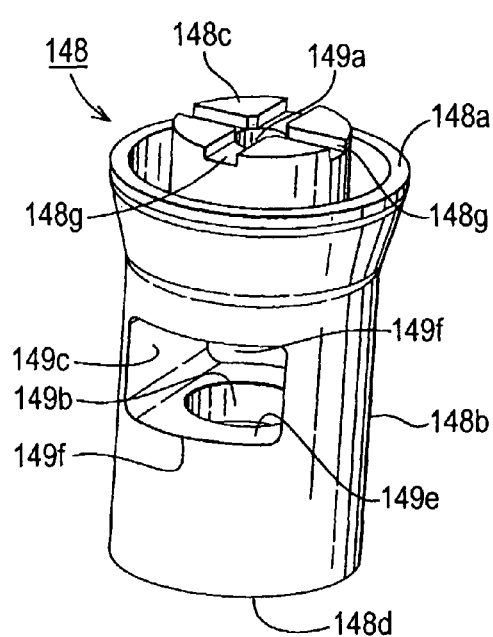
FIGS. 13A and 13B are respectively perspective and cross-sectional side views of a forward sealing element of the fluid dispenser of FIGS. 7 to 10 which slidably mounts on the piston member of FIGS. 11A-B to form a one-way valve.
Figure 13:
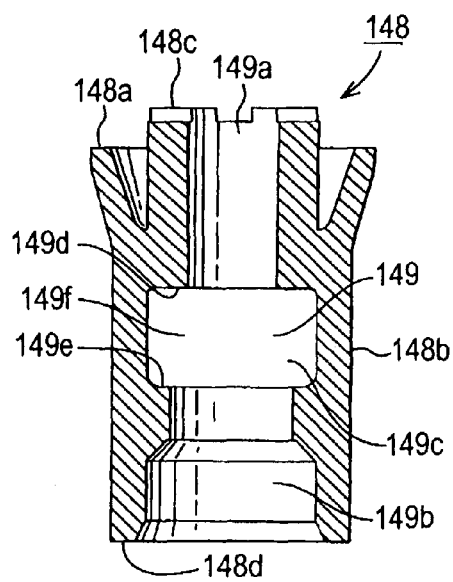

Now referring additionally to FIGS. 13A and 13B, the piston member 114 further carries on its forward section 114a a tubular forward sealing element 148 to form a dynamic (sliding) seal between the piston member 114 and the forward section 120a of the dosing chamber 120, but only during a particular phase of the piston member stroke, as will be described in more detail hereinafter.

The forward sealing element 148 is also of the lip-seal type, but this time only being provided with a resilient, annular sealing lip 148a at its forward end. The outer diameter of the forward lip seal 148a is less than the inner diameter of the rear dosing chamber section 120b, but greater than the inner diameter of the forward dosing chamber section 120a. Consequently, the forward sealing lip 148a is able to be biased into sealing engagement with the inner surface of the forward dosing chamber section 120a.

As will be observed, the forward sealing element 148 is slidably mounted on the forward section 114a of the piston member 114. In more detail, the forward sealing element 148 comprises a tubular body 148b, from which the sealing lip 148a depends, and provides an axial, open-ended bore 149 through the forward sealing element 148 in which the forward section 114a of the piston member 114 is slidably mounted. The bore 149 comprises forward and rear bore sections 149a, 149b and an enlarged, central chamber 149c. The forward and rear bore sections 149a, 149b respectively extend from the central chamber 149 to openings in the forward and rear ends 148c, 148d of the forward sealing element 148. The forward end 148c is provided with grooves 148g which intersect the forward bore opening therein. The central bore chamber 149c is provided with a pair of diametrically opposed windows 149f through the tubular body 148b.

The annular flange 114i of the piston member 114 is located inside of the central bore chamber 149c. The central bore chamber 149c has transversely-oriented forward and rear end walls 149d, 149e which selectively engage the annular flange 114i of the piston member 114 to delimit the sliding movement of the forward sealing element 148 on the piston member 114. Specifically, the forwardmost position of the forward sealing element 148 relative to the piston member 114 is delimited by the rear end wall 149e abutting the annular flange 114i (see e.g. FIG. 9B), and conversely the rearmost position of the forward sealing element 148 relative to the piston member 114 is delimited by abutment of the forward end wall 149d with the annular flange 114i (see e.g. FIG. 9C).

The sliding movement of the forward piston member section 114a in the forward sealing element bore 149 forms a one-way valve. The one-way valve is closed when the forward sealing element 148 is in its rearmost position relative to the piston member 114 and open as the forward sealing element 149 moves towards its forwardmost position relative to the piston member 114, as will be discussed in more detail hereinafter.

To this end, it will be understood that the annular flange 114i forms a fluid-tight seal against the forward end 149d of the central bore chamber 149c when the forward sealing element 148 is in its rearmost position.

In operation, as the piston member 114 strokes forwardly relative to the dosing chamber 120 (see e.g. FIG. 9C), the forward sealing element 148 moves forwardly with the piston member 114 through engagement of the annular flange 114i with the forward end wall 149d of the central bore chamber 149c. Thus, the one-way valve is closed in the forward stroke of the piston member 114. The forward stroke also brings the forward sealing element 148 into sliding sealing engagement with the forward section 120a of the dosing chamber 120.

Once the piston member 114 reaches its forward position at the end of its forward stroke, as delimited by abutment of the forward end 148c of the forward sealing element 148 with a forward end wall 120c of the dosing chamber 120 (see e.g. FIG. 9C), the piston member 114 starts its return, rearward stroke towards its rearward position. In an initial phase of the rearward stroke, the piston member 114 moves rearwardly relative to the forward sealing element 148 so that the one-way valve is moved to its open position for the rearward stroke. The rearward stroke of the piston member 114 ends with the piston member 114 being disposed in its rearward position, where the forward sealing element 148 is disposed rearwardly of the forward dosing chamber section 120a, i.e. in the rear dosing chamber section 120b or, as shown in FIG. 9B, in the step 120s, so that the forward and rear dosing chamber sections 120a, 120b are in flow communication about the forward sealing element 148 (e.g. via the flutes 120d where the rest position is in the step 120s).

It will thus be appreciated that in an initial phase of the forward stroke of the piston member 114 in the dosing chamber 120, from its rest position towards its forward position, the piston member 114 moves forwardly relative to the forward sealing element 148 to (re)close the one-way valve.

The rear and forward sealing elements 128, 148 in this embodiment are injection moulded from low density polyethylene (LDPE), but other functionally equivalent plastics materials could be used.

The return, compression spring 118 in the fluid dispenser 110 is provided to bias the piston member 114 to its rearward (resting) position relative to the dosing chamber 120, which is shown in FIGS. 7B and 9B. The spring 118 may be made from a metal (e.g. stainless steel, for instance 316 or 304 grade) or a plastics material. The return or biasing force of the return spring 118 may be 5N at rest, increasing to 8.5N as it is compressed. The biasing force of the return spring 118 acts to reset the piston member 114 in its rear position relative to the dosing chamber 120 defined in the main housing 112 by acting on the main housing annular flange 112b to bias the main housing 112 forwardly to its relative position shown in FIGS. 7B and 9B.

As shown in FIGS. 21A and 21B, the nipple 160 is comprised in a separate cylindrical cap 165. The cap 165 is of cup-form, having an annular side skirt 165a and a forward end wall 165b which form the boundary walls of an internal cylindrical chamber 165c which is open at the rear end 165d of the cap 165. Moreover, the nipple 160 is in the form of a central sealing tip which projects forwardly from the forward end wall 165b.

A plurality of apertures 165e are also formed in the forward end wall 165b, about the base of the sealing tip 160, to communicate with the internal chamber 165c. In this embodiment, there are three equi-angularly spaced apart apertures 165e, but alternatively there may be less or more in number than three apertures.

The inner circumferential side surface 165f of the internal chamber 165 is provided with a pair of circumferential beads 165g. The outer circumferential edge of the forward end wall 165b presents a resilient, annular sealing lip 165h.

In this embodiment, the cap 165 is formed from LDPE, but again other plastics materials could be used.

As shown in FIGS. 9B and 9C, for instance, the cap 165 is mounted over the forward section 112h of the main housing 112 to enclose the forward bore section 112f of the main housing 112. The cap 165 is secured to the main housing 112 by the respective internal and external beads 165g, 112i clipping or interlocking together such that they move in unison.

As further shown in FIGS. 9B and 9C, a valve mechanism 189 is located in the forward bore section 112f of the main housing 112. The valve mechanism 189 comprises a cylindrical, elongate valve element 191 mounted for axial movement in the forward bore section 112f.

As shown in FIGS. 19A and 19B, the valve element 191 has a cylindrical forward section 191a and a coaxial, enlarged rear section 191b. The rear section 191b has a forward portion 191c and a frusto-conical rear portion 191d sized to sealingly fit in the restricted bore section 112e of the main housing 112 for closure thereof. A plurality of axial grooves 191e are formed in the outer peripheral surface of the rear section 191b to extend through the forward portion 191c and partially into the rear portion 191d.

Turning back to FIGS. 9B and 9C, the valve mechanism 189 further comprises a return, compression spring 193 which extends rearwardly from the inner surface of the forward end wall 165b of the cap 165 onto an annular flange 191f at the forward end of the rear section 191b of the valve element 191. The return spring 193 acts to bias the valve element 191 rearwardly to dispose the frusto-conical rear portion 191d in the restricted bore section 112e for sealing closure thereof.

The valve element 191 in this embodiment is injection moulded from low density polyethylene (LDPE) or polypropylene (PP), but other functionally equivalent plastics materials could be used. The return spring 193 may be of metal (e.g. of stainless steel, such as of 304 or 316 grade) or a plastics material. The return spring 193 may have a return force of approximately 0.4N.

FIGS. 9B and 9C also show that the cylindrical stopper portion 176 has a cap form for fitting on the bottle neck 178. In this embodiment, the stopper portion 176 is injection moulded from polypropylene (PP). However, other plastics materials could be used.

Referring also to FIGS. 15A and 15B, the stopper portion 176 has an outer annular skirt 176a, which surrounds the outer peripheral surface of the flange 180 of the bottle neck 178, and a concentrically arranged inner annular skirt 176b, which plugs the bottle neck 178. The inner peripheral surface of the outer annular skirt 176a is provided with circumferentially-oriented bead 176q to engage underneath the flange 180 of the bottle neck 178 to give a snap-fit connection of the stopper portion 176 to the bottle 170. The bead 176q may be continuous, or segmented (as here) to simplify the moulding of the stopper portion 176.

The stopper portion 176 has a roof 176c at its forward end extending radially inwardly from the outer skirt 176a to the inner skirt 176b. The inner skirt 176b encloses an internal cavity 176d which extends rearwardly from a opening 176e in the roof 176c. The cavity 176d has a floor 176f at its rear end from which upstands an elongate tubular projection 176g.

The tubular projection 176g has an open rear end 176h, a forward end wall 176i, an internal cavity 176j which extends forwardly from the open rear end 176h to the forward end wall 176i, and a forward opening 176k in the forward end wall 176i to place the internal cavities 176d, 176j in flow communication.

As shown in FIG. 9B, for example, the supply (dip) tube 172 (e.g. of polypropylene (PP)) inserts into the internal cavity 176j of the tubular projection 176g as an interference fit, with the supply tube 176 abutting the forward end wall 176i of the tubular projection 176g. Likewise, the tubular projection 176g inserts into the internal cavity 114f of the rear section 114b of the piston member 114 so that the forward end wall 176i of the tubular projection 176g abuts the forward face 114n of the internal cavity 114f. In this way, the bore network 114j in the piston member 114 is placed in flow communication with the fluid supply 170 through the supply tube 172. The supply tube 172 extends to adjacent the bottom of the fluid supply 170 so fluid can still be delivered from the fluid supply 170 in normal use (i.e. upright or substantially upright) when nearly empty.

The tubular projection 176g is secured against relative movement in the internal cavity 114f of the piston member 114 by the internal cavity 114f of the piston member 114 presenting a plurality of circumferential beads 114v on its inner circumferential surface to which clip or interlock circumferential beads 176s provided on the outer circumferential surface of the tubular projection 176g.

As further shown in FIG. 9B, for example, the tubular body 112a of the main housing 112 is also mounted in the internal cavity 176d of the stopper portion 176 for relative sliding motion therebetween. The relative sliding motion between the stopper portion 176 and the main housing 112 effects the relative sliding motion between the piston member 114 and the dosing chamber 120 because the piston member 114 is carried on the tubular projection 176g of the stopper portion 176. The relative sliding motion is achievable by having the main housing 112 move and maintaining the fluid supply 170 stationary, or vice-versa, or by having the main housing 112 and fluid supply 170 move towards one another at the same time.

It will be seen from FIG. 9B, for example, that a sealing ring 171 is interposed between the stopper portion 176 and the fluid supply 170 to prevent leaks therebetween. The sealing ring 171 may be made from a thermoplastic elastomer (e.g. SANTOPRENE®), an ethylene-vinyl acetate rubber (EVA), a polyethene or from a low density polyethylene (LDPE) laminate comprising a LDPE foam core sandwiched between LDPE outer layers (sold under the brand name "TriSeal").

The fluid dispenser 110 further comprises a cylindrical carrier member 195 which surrounds the tubular body 112a of the main housing 112. As shown in FIGS. 18A and 18B, the carrier member 195 has an annular body 195a which is spaced radially outwardly of the tubular body 112a of the main housing 112 to define an annular space 187 therebetween (see FIG. 9B). The annular body 195a has an inwardly projecting, annular flange 195b at its rear end 195c, and a plurality of outwardly projecting clips 195d disposed on tongues 195f defined by the castellated profile at its forward end 195e.

As shown in FIG. 9B, the return spring 118 extends rearwardly from the rear face 112j of the main housing annular flange 112b into the annular space 187 between the carrier member 195 and the main housing 112 and onto the carrier member annular flange 195b for carriage thereon.

In normal use of the fluid dispenser 110, the carrier member 195 seats on the roof 176c of the stopper portion 176, both in the rest and fired positions of the fluid dispenser 110 to be discussed hereinafter. This normal position for the carrier member 195 is shown in FIGS. 9B (rest) and 9C (fired).

The carrier member 195 in this embodiment is also injection moulded from polypropylene (PP), but other plastics materials may be used.

Figure 36:
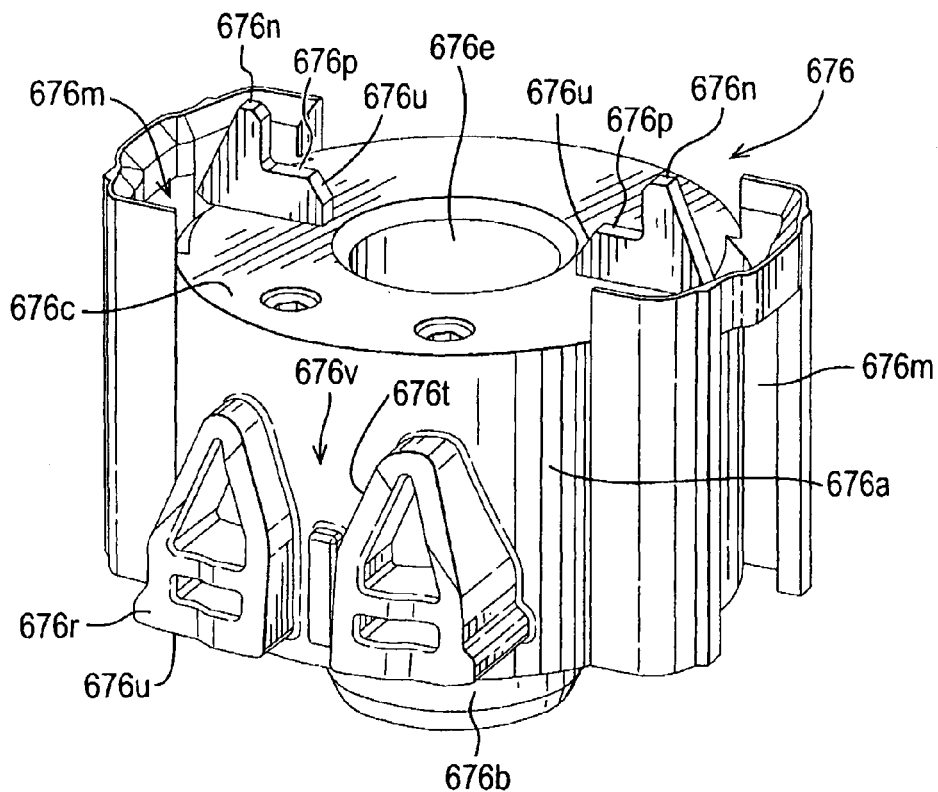
FIGS. 36A and 36B are respectively perspective and underneath plan views of a first alternative stopper portion.
Figure 36:
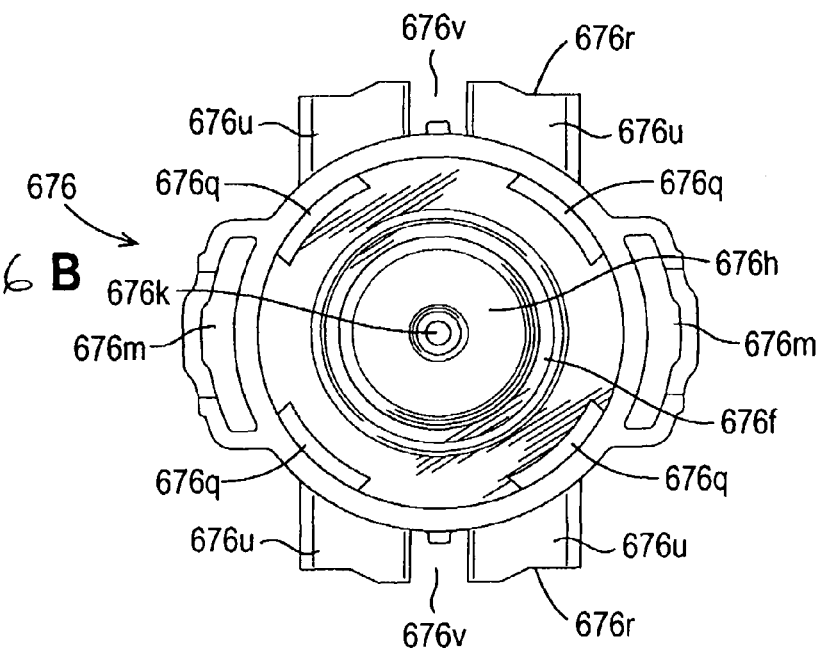

Referring back to FIGS. 15A and 15B which show the stopper portion 176, it will be seen that the roof 176c carries a pair of diametrically opposed main protrusions 176n and a series of minor protrusions 176p arranged equi-angularly about the roof opening 176e. The main protrusions 176n are adapted in use to act on the outer circumference of the carrier member 195 to centralise it with respect to the stopper portion 176 as the carrier member 195 is seated on the roof 176c. The minor protrusions 176p fit into complementary grooves (not shown) in the annular flange 195b of the carrier member 195 to correctly orient the carrier member 195 on the roof 176c so that the clips 195d will clip into T-shaped cut-outs 116g in the nozzle 116 to be described hereinafter. In a modification, such as shown in FIG. 36, there may be provided just two minor protrusions, each forming a radial extension from one of the main protrusions.

The fluid dispenser 110 also comprises a tubular nozzle insert 197 surrounding the cap 165 mounted on the forward section 112h of the main housing 112. FIGS. 20A and 20B show the nozzle insert 197 has a hollow body 197a which at its forward end 197b has an end wall 197c through which is provided a central aperture 197d. The body 197a comprises a first annular section 197e which extends rearwardly from the forward end wall 197c and has, about its rear end, an outer circumferential bead 197p for forming a seal with the inner surface of the nozzle 116. The rear end 197f of the nozzle insert body 197a is presented by a plurality of spaced-apart, rearwardly extending legs 197g. There are four legs 197g in this embodiment. The legs 197g are arranged circumferentially on the body 197a about a rear opening 197h to the body 197a. Each leg 197g comprises an outwardly extending foot 197i.

The nozzle insert body 197a further comprises a second annular section 197j spaced rearwardly of the first annular section 197e and from which the legs 197g depend. The first and second annular sections 197e, 197j are joined together by a plurality of spaced-apart, resilient ribs 197k which are disposed on the outer circumference of the body 197a and extend on a diagonal path between the first and second annular sections 197e, 197j.

The second annular section 197j presents a pair of diametrically opposed, forwardly oriented, resilient tongues 197l. The tongues 197l are disposed between the ribs 197.

On the forward face of the forward end wall 197c there is provided an annular lip 197m about the central aperture 197d. The forward end wall 197c is further provided with apertures 197n therethrough.

The nozzle insert 197 in this embodiment is injection moulded from polypropylene (PP), but could be made from other plastics materials, as will be appreciated by those skilled in the art.

FIGS. 9B and 9C show the nozzle insert 197 is arranged in the fluid dispenser 110 about the cap 165 so that the sealing tip 160 of the cap 165 projects through the central aperture 197d in the forward end wall 197c of the nozzle insert 197. Moreover, the sealing lip 165h of the cap 165 is slidingly sealingly engaged with the inner circumferential surface of the first annular section 197e of the nozzle insert 197.

The annular space between the nozzle insert 197 and the cap 165 defines the fluid dispensement chamber 146.

It will be seen from FIGS. 21A-B that the cap 165 is provided with an outwardly projecting, annular flange 165i. As will be appreciated by additional reference to FIGS. 21A-B and FIG. 9B, as the cap 165 is inserted into the nozzle insert 197 during assembly, the flange 165i pushes past the resilient tongues 197l of the nozzle insert 197 to be retained in the space between the first and second annular sections 197e, 197j of the nozzle insert 197.

Mounted on the sealing tip 160 of the cap 165 is the sealing member 154. The sealing member 154 is sealingly mounted on the sealing tip 160 and seated on the forward end wall 197c of the nozzle insert 197. The seal formed between the longitudinal surfaces of the sealing member 154 and the sealing tip 160 is such that fluid cannot pass therebetween.

The sealing member 154 is made from natural rubber or a thermoplastic elastomer (TPE), but other elastic materials may be used which have a 'memory' to return the sealing member 154 to its original state. The sealing member 154 may be made from EPDM, for instance as an injection moulded EPDM component.

Figure 10:
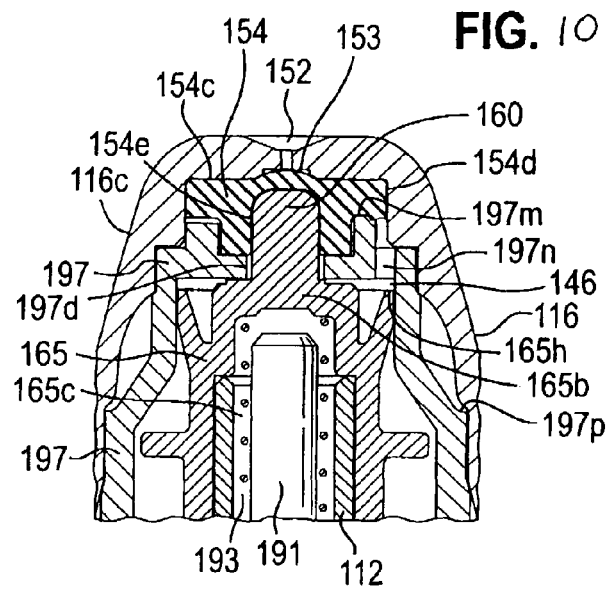
FIG. 10 is an enlarged cross-sectional view of the nozzle area of the fluid dispenser of FIGS. 7 to 9 showing the tip seal arrangement therefor.

As shown in FIGS. 9B and 10, in this tip seal arrangement the return spring 118 biases the cap 165 into abutment with the nozzle insert 197 to control the position of the sealing tip 160 relative to the sealing member 154. More particularly, the forward end wall 165b of the cap 165 is biased into direct engagement with the rear side of the forward end wall 197c of the nozzle insert 197. This has the advantage of protecting the sealing member 154 from excessive force being applied to it by the sealing tip 160 in the rest state of the fluid dispenser 110, which of course is the predominant state of the fluid dispenser 110.

As illustrated by FIGS. 7 and 8, the nozzle 116 is slidably connected to the stopper portion 176 through engagement of a pair of rearwardly directed runners 116a of the nozzle 116 in complementary tracks 176m on the outer circumference of the stopper portion 176. The runners 116a are provided with outwardly extending clips 116b to secure the runners 116a in the tracks 176m and to delimit the maximum sliding separation between the nozzle 116 and the stopper portion 176.

Figure 16A:
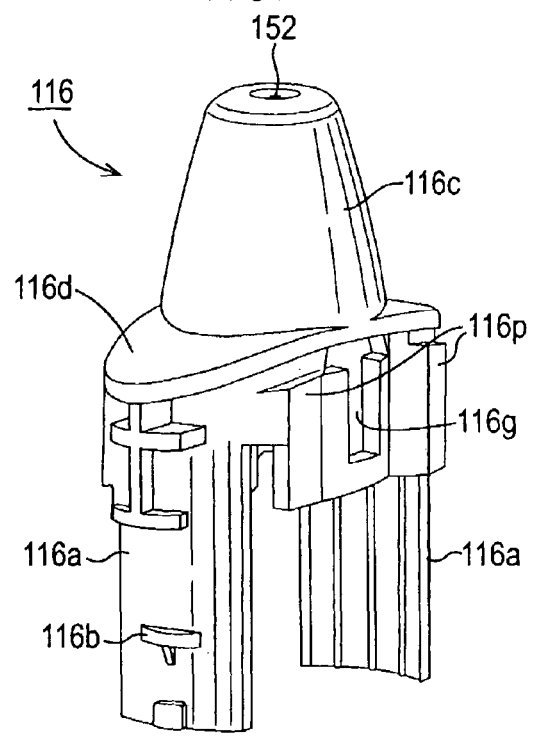
FIGS. 16A and 16B are respectively perspective and cross-sectional side views of a nozzle of the fluid dispenser of FIGS. 7 to 10 which slidingly mounts on the stopper portion of FIGS. 15A-B.
Figure 16B:
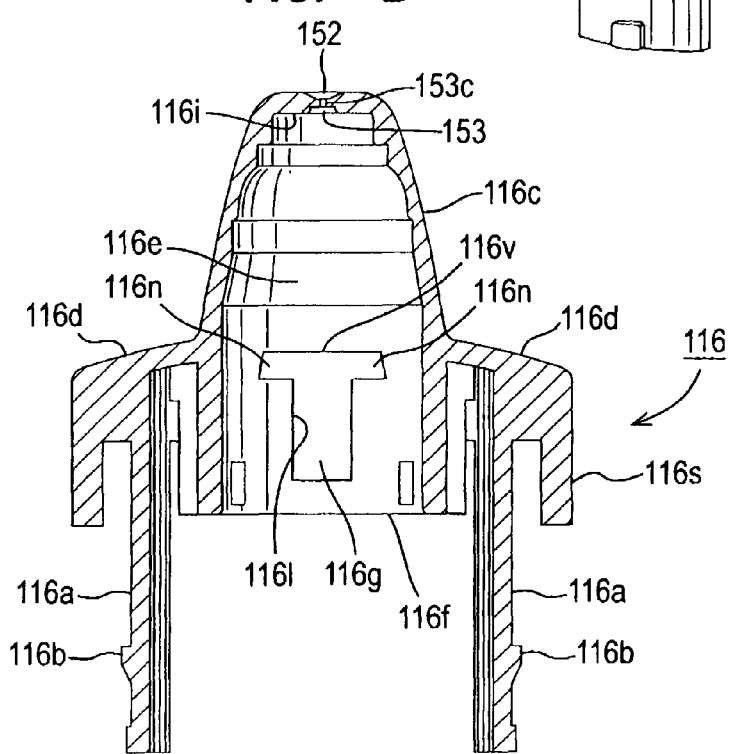
Figure 20:
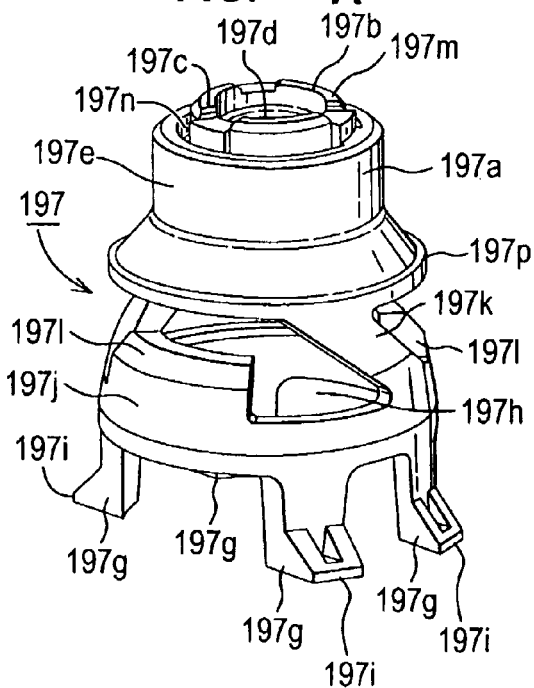
FIGS. 20A and 20B are respectively perspective and cross-sectional side views of a nozzle insert of the fluid dispenser of FIGS. 7 to 10 which inserts in the nozzle of FIGS. 16A-B and 17.
Figure 20:
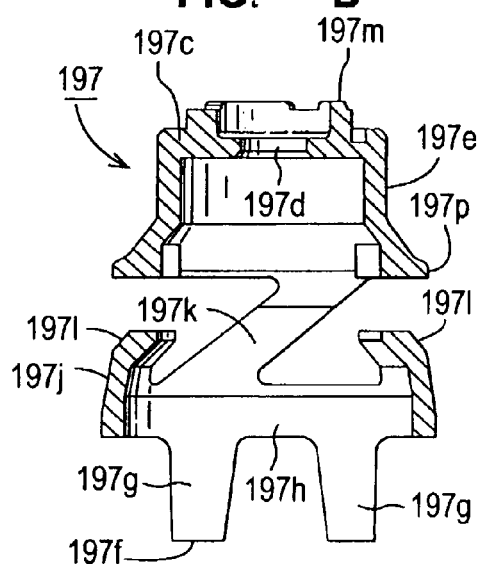
Figure 21:
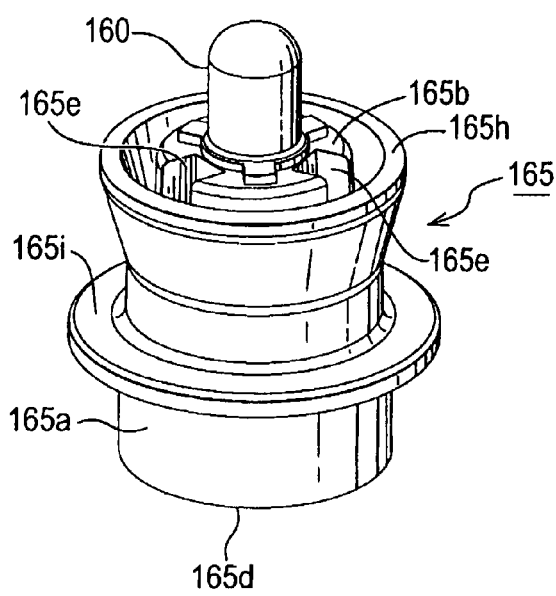
FIGS. 21A and 21B are respectively perspective and cross-sectional side views of a cap of the fluid dispenser of FIGS. 7 to 10 which mounts on the main housing of FIGS. 14A-B.
Figure 21:
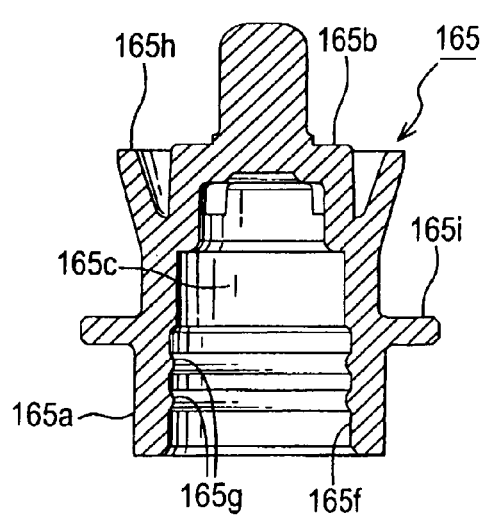

As further illustrated in FIGS. 16A and 16B, the nozzle 116 has a nozzle section 116c, sized and shaped for insertion into a nostril of a human being, in which is formed the fluid outlet 152, and shoulders 116d at the rear end of the nozzle section 116c from which depend the runners 116a.

The nozzle section 116c encloses an internal cavity 116e having a rear open end 116f. A pair of T-shaped cut-outs 116g are provided on opposite sides of the internal cavity 116e. The longitudinal section 116l defines a track in which the clips 195d of the carrier member 195 are clipped to secure the carrier member 195 to the nozzle 116 and to provide for sliding movement therebetween.

Moreover, in each corner of the crossbar section 116v of the T-shaped cut-outs 116g is clipped one of the feet 197i of the nozzle insert 197 to fix the nozzle insert 197 in the internal cavity of the nozzle 116. These connections are best seen in FIGS. 7A-C. The resilient ribs 197k of the nozzle insert 197 act as springs to enable the nozzle insert 197 to be inserted into the nozzle 116 and then the second annular section 197j compressed so that the feet 197i fix in the T-shaped cut-outs 116g. The nozzle insert 197 is then held captive in the nozzle 116. Moreover, the first annular section 197a forms a fluid-tight seal against the adjacent inner surface of the nozzle internal cavity 116e to prevent liquid leaking therebetween.

As shown in FIG. 17, a swirl chamber 153 is formed in the forward end wall 116i of the nozzle internal cavity 116e. The swirl chamber 153 comprises a central cylindrical chamber 153a and a plurality of feed channels 153b which are equi-spaced about the central chamber 153a in tangential relationship thereto. At the centre of the central chamber 153a is a passageway 153c (exit) connecting the swirl chamber 153 to the fluid outlet 152. The feed channels 153b may be square cut and may have a depth in the range of 100 to 500 microns (inclusive), such as 100 to 250 microns (inclusive), for instance in the range of 150 to 225 microns (inclusive). The width may be the same as the depth, for instance 400 microns.

To accelerate the fluid as it flows towards the central chamber 153a, the feed channels 153b are provided with a decreasing cross-sectional area in the fluid flow direction.

As shown in FIG. 17, in this instance the feed channels 153b decrease in width as they approach the central chamber 153a. The decreasing cross-sectional area may then be provided by maintaining a constant channel depth along the length of the feed channels 153b.

In an alternative case, the width of the channels 153b may remain uniform throughout, and the channel depth decrease as the feed channels 153b approach the central chamber 153a. In this regard, the depth of the feed channels 153b may vary uniformly from 400 microns to 225 microns, for example.

The width and depth of the feed channels 153b may also both vary along their length whilst providing the decreasing cross-sectional area in the fluid flow direction. In this regard, the aspect (width:depth) ratio along the length of the feed channels 153b may be maintained constant.

Preferably, the feed channels 153b are of narrow width to inhibit their obstruction by the sealing member 154, e.g. as from creep of the sealing member material. Preferably, the feed channels 153b have a low aspect (width:depth) ratio; i.e. are narrow and deep, preferably with the width being less than the depth (e.g. of rectangular cross-section).

As will be understood from FIG. 10, a gap exists between the side face 154d of the sealing member 154 and the adjacent inner side faces of the internal cavity 116e of the nozzle 116 to enable fluid to flow towards the swirl chamber 153. This fluid flow path could instead be formed by forming longitudinal grooves in the outer side face of the sealing member 154 and/or the inner side faces of the nozzle 116. More particularly, the gap/fluid flow path between the sealing member 154 and the nozzle 116 places the feed channels 153b of the swirl chamber 153 in flow communication with the fluid dispensement chamber 146 via the apertures 197n and, optionally, gaps between the sealing member 154 and the forward opening 197d of the nozzle insert 197.

However, as shown most clearly in FIG. 10, the forward face 154c of the flexible sealing member 154 is held by the nozzle insert 197 in sealing engagement with the forward end wall 116i of the nozzle 116. This means that the sealing member 154 seals over the swirl chamber feed channels 153b and that any liquid travelling up the gap between the side face 154d of the sealing member 154 and the nozzle 116 has to pass into the swirl chamber feed channels 153b and thence into the central chamber 153a of the swirl chamber 153.

Moreover, the return spring 118 acts to bias the main housing 112 forwardly in the nozzle 116 whereby the sealing tip 160, on the cap 165 fixed on the forward section 112h of the main housing 112, pushes a central part of the forward face 154c of the sealing member 154 into the central chamber 153a of the swirl chamber 153 to sealingly close the passageway 153c to the fluid outlet 152. In this way, no fluid can enter or exit the fluid outlet 152, or more particularly the swirl chamber 153, until the sealing tip 160 releases the central part of the elastic sealing member 154, to be described in more detail hereinafter.

Figure 23:
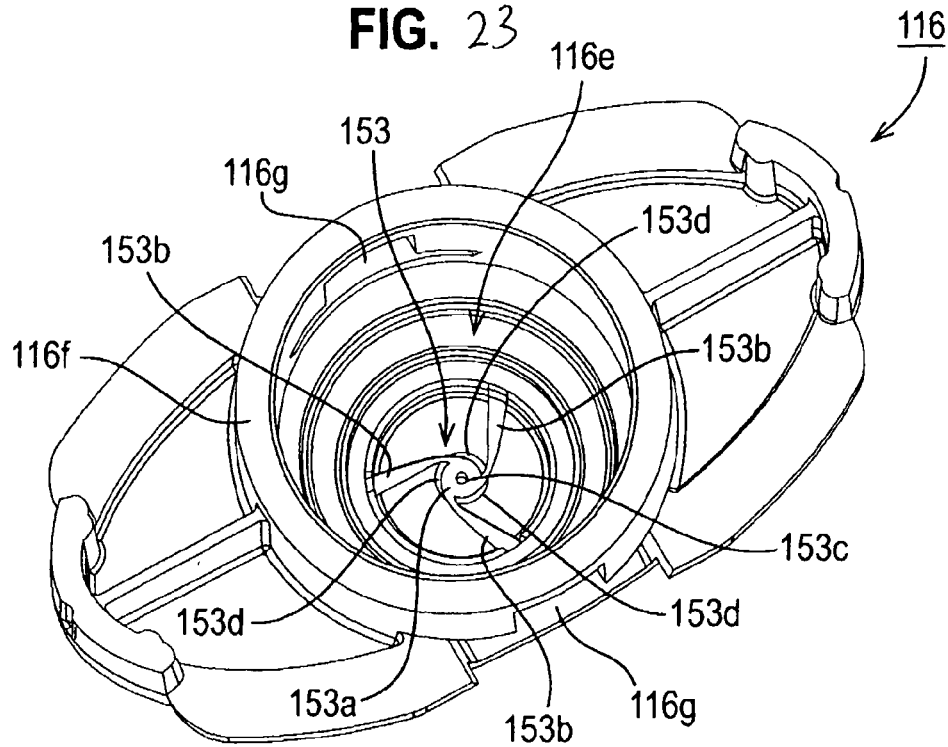
FIG. 23 corresponds to FIG. 17 showing an modification to the swirl chamber.

In a modification, the straight walls of the central chamber 153a of the swirl chamber 153 may be chamfered to facilitate pushing the central part of the sealing member 154 thereinto. This is shown in FIG. 23, with the chamfered surface denoted by reference number 153d.

The nozzle 116 in this embodiment is injection moulded from polypropylene (PP), but other plastics materials could be used.

To operate the fluid dispenser 110, it is first necessary to prime the device to fill all the fluid pathways between the fluid outlet 152 and the fluid supply 170. To prime, the fluid dispenser 110 is operated in exactly the same manner as for later dispensing operations. As shown in FIGS. 7B-C and 9B-C, this is done by (i) sliding the nozzle 116 relatively towards the fluid supply 170, by acting on the nozzle 116, or the fluid supply 170, while keeping the other stationary, or acting on both, to move the fluid dispenser from its rest position (FIGS. 7B and 9B) to its fired position (FIGS. 7C and 9C); and (ii) allowing the return spring 118 to return the nozzle 116 to its separated position relative to the fluid supply 170 to return the fluid dispenser 110 to its rest position. The relative sliding movement of the nozzle 116 and the fluid supply 170 is effected by the runners 116a of the nozzle 116 sliding in the tracks 176m of the stopper portion 176 fixed in the neck 178 of the fluid supply 170.

It will be appreciated that the relative movement of the nozzle 116 and the fluid supply 170 to effect priming and then dispensing from the dispenser 110 is actually relative movement between the nozzle 116 and the components assembled thereto (the "nozzle assembly", including the nozzle insert 197, the cap 165 and the main housing 112) and the fluid supply 170 and the components assembled thereto (the "bottle assembly", including the stopper portion 176 and piston member 114). The return spring 118 biases the nozzle assembly away from the bottle assembly and thus the piston member 114 to its rearward, rest position in the dosing chamber 120 in the main housing 112.

FIGS. 22A to 22J show the priming process, and the liquid flow during priming, albeit for a fluid dispenser 310 which is a subtle modification (but functional equivalent) of the fluid dispenser 110 of FIGS. 7 to 21, with like features being assigned like reference numbers. While the fluid dispenser 310 of FIGS. 22A to 22J will be discussed in more detail after the description of the fluid dispenser 110, FIGS. 22A to 22J are a useful reference to the detailed description of priming of the fluid dispenser 110 which now follows.

Each complete (reciprocal) cycle of the afore-mentioned sliding movement (a "pumping cycle") between the nozzle 116 and the fluid supply 170 includes a phase which creates a negative pressure in the dosing chamber 120 which draws liquid from the fluid supply 170 up the supply tube 172 and this cycling continues until liquid fills up all the fluid pathways from the fluid supply 170 to the fluid outlet 152.

Figure 22C:
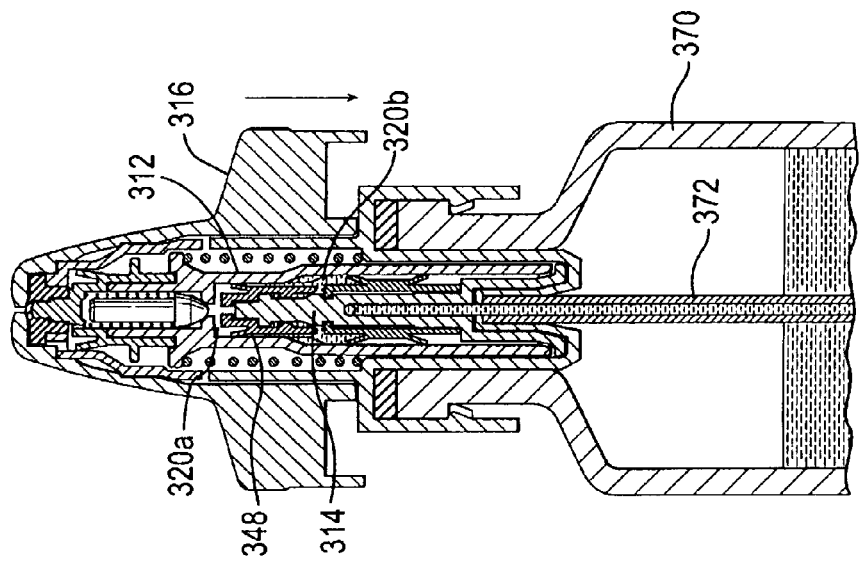
FIGS. 22A to 22J are cross-sectional side views of a modified version of the fluid dispenser of FIGS. 7 to 21 for use in the third to fifth dispensing devices showing the sequential advancement of liquid therewithin during priming of the dispenser.
Figure 22D:
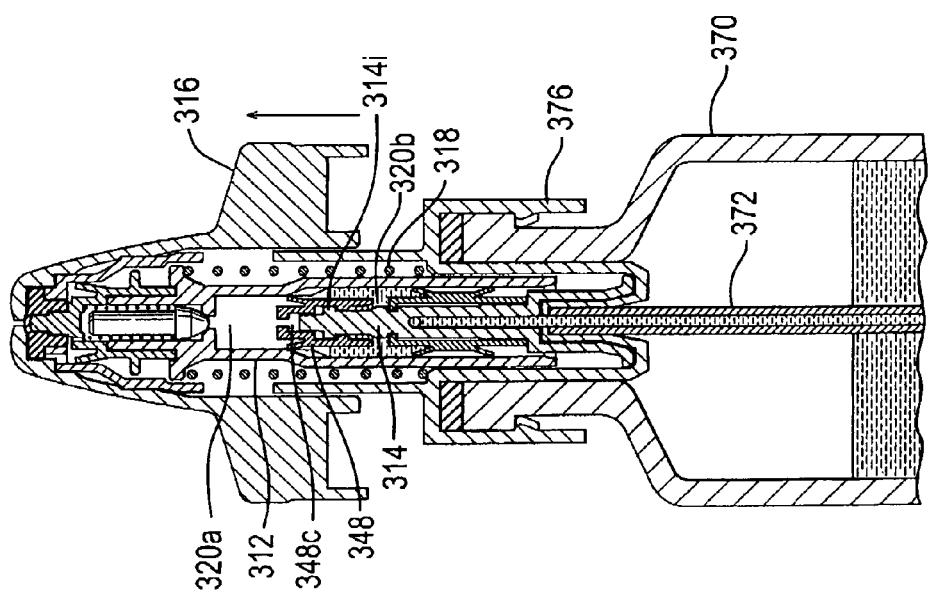
Figure 22:
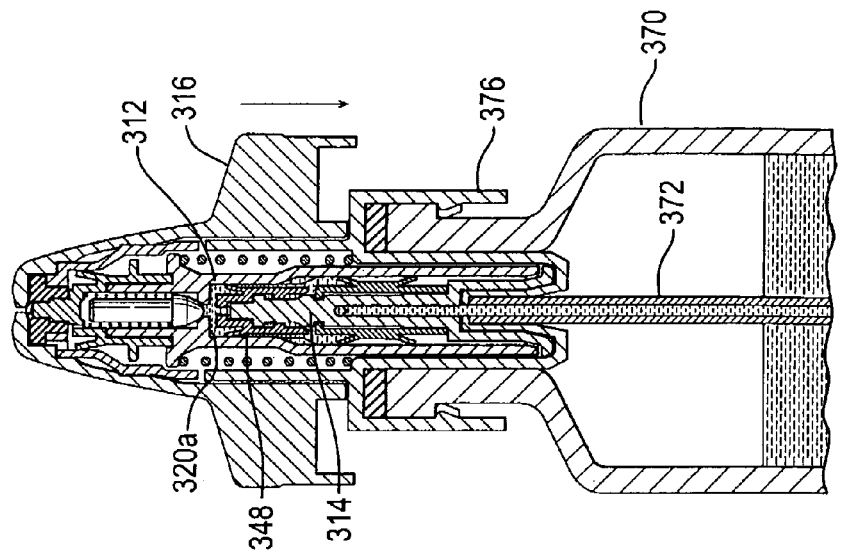
Figure 22:
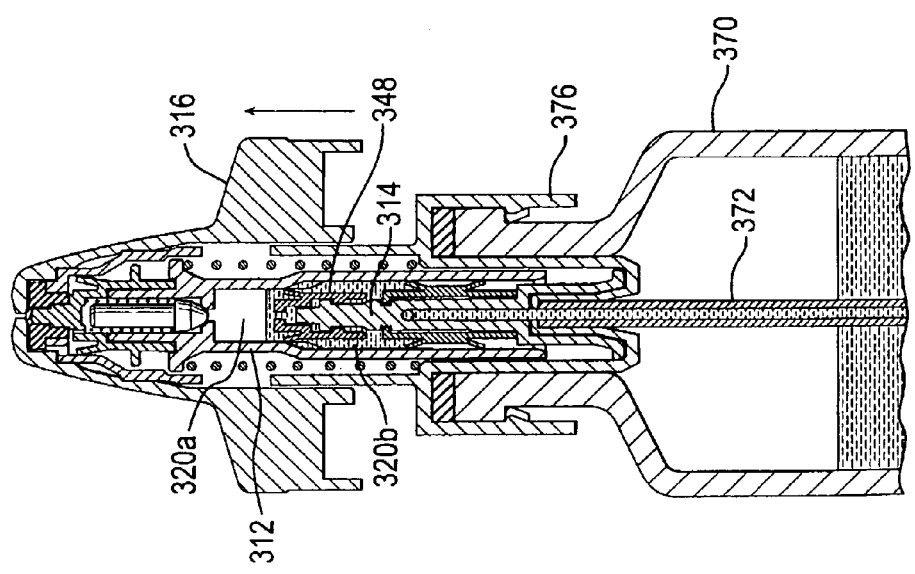

In more detail, the liquid flows forwardly through the supply tube 172, into the bore network 114j of the piston member 114 via the rear opening 114m thereof, and out of the forward openings 114q of the bore network 114j into the rear section 120b of the dosing chamber 120 via the axial grooves 114r in the outer periphery of the piston member 114 (see FIGS. 22A to 22C).

As a result of the nozzle 116 and the fluid supply 170 respectively carrying the main housing 112 and the piston member 114, as described above, each reciprocal cycle of relative movement of the nozzle 116 and the fluid supply 170 causes the piston member 114 to stroke in corresponding reciprocating fashion inside the dosing chamber 120 defined by the main housing 112 from the rear (rest) position.

As the piston member 114 returns from its forward position to its resting, rear position, in the second half of each cycle, a negative pressure is created in the dosing chamber 120 to draw the liquid further forwardly. Moreover, the piston member 114 moves rearwardly relative to the forward sealing element 148 to open the one-way valve, as described hereinabove, and therefore allows the liquid to flow forwardly into the forward dosing chamber section 120a through the one-way valve (see FIGS. 22D to 22G). Friction forces between the lip seal 148a and the dosing chamber wall assist in the telescoping of the forward sealing element 148 on the piston member 114.

Specifically, as the annular flange 114i of the piston member 114 disengages from the forward end wall 149d of the central bore section 149c of the bore 149 in the forward sealing element 148, the liquid to the rear of the one-way valve is able to flow around the flange 114i of the piston member 114 via the windows 149f in the forward sealing element 148, over the tip part 114u of the piston member 114 and through the forward bore section 149a of the forward sealing element 148 into the forward section 120a of the dosing chamber 120.

Figure 22H:
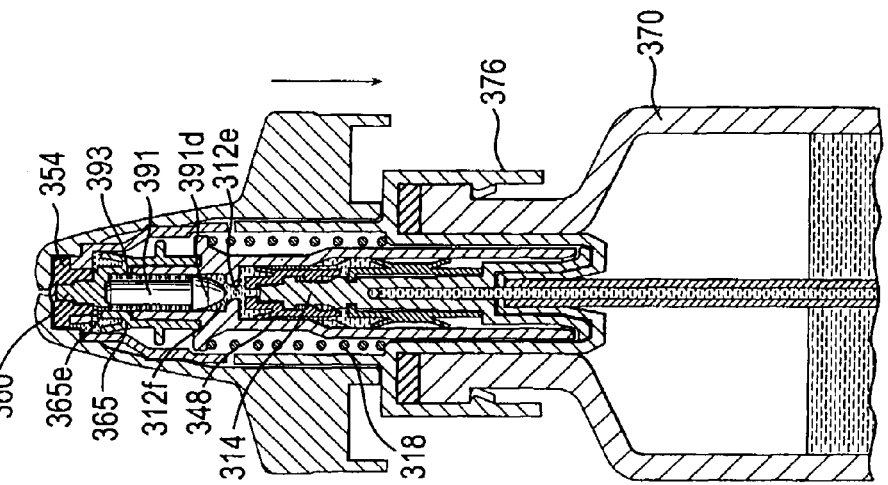
Figure 22G:
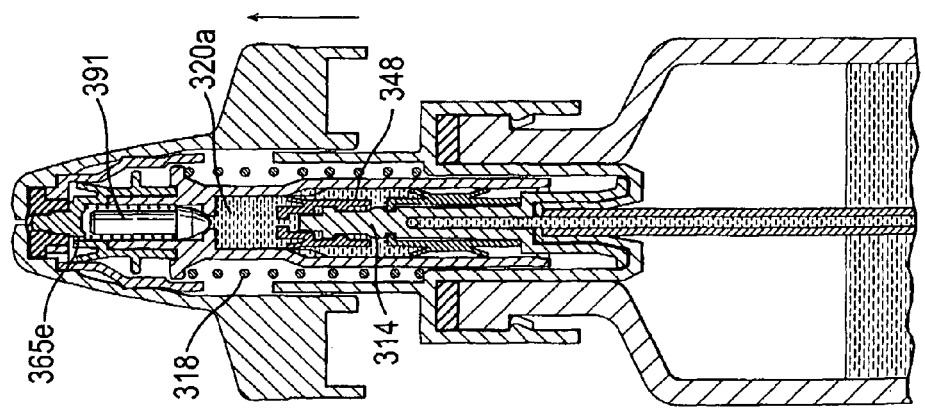

After the dosing chamber 120 (including the forward section 120a) is filled with liquid by priming the fluid dispenser with enough pumping cycles (see FIG. 22G), each cycle thereafter results in the same amount (a metered volume) of the liquid being pumped forward from the dosing chamber 120 through the restricted bore section 112e in the main housing 112 (compare FIGS. 22G and 22H).

In more detail, in the forward stroke of the piston member 114 to its forward position in the dosing chamber 120, the valve mechanism 189 in the forward bore section 112f keeps the restricted bore section 112e shut until after the forward sealing element 148 comes into sealing engagement with the inner surface of the forward dosing chamber section 120a. This is because the biasing force of the valve return spring 193 is not overcome by the hydraulic pressure of the liquid produced on the initial (first) phase of the forward stroke of the piston member 114 prior to the forward sealing element 148 sliding into sealing engagement in the forward dosing chamber section 120a to sealingly separate the forward and rear dosing chamber sections 120a, 120b.

This first phase may be referred to as the "bleed phase" because it results in liquid being pumped rearwardly from the dosing chamber 120 back into the fluid supply 170 (i.e. bled) until the piston member 114 locates the forward sealing element 148 in the forward dosing chamber 120a (i.e. so there is no longer any flow therebetween, recalling that the one-way valve defined by the forward sealing element 148 on the piston member 114 is reclosed in the forward stroke of the piston 114). The bleed flow is aided by the provision of the at least one axial flute 120d in the step 120s of the dosing chamber 120.

Once the forward sealing element 148 is located in the forward dosing chamber 120a, the forward dosing chamber 120a, and the metered volume of liquid which fills it, is sealed. The flutes 120d no longer provide a fluid flow path into the forward dosing chamber section 120a, since the forward sealing element 148 is at, or forward of, the forward end of the flutes 120d and in sealing engagement with the inner wall of that chamber section 120a.

In the next (second) phase of the continuous forward stroke of the piston member 114, the piston member 114 increases the hydraulic pressure of the liquid in the forward dosing chamber section 120a as it moves relatively towards the forward end wall 120c of the forward dosing chamber section 120a presented by the annular shoulder 112d of the main housing 112.

At a certain point in the second phase of the forward stoke of the piston member 114, which may be nearly instantaneous, the hydraulic pressure of the liquid in the forward dosing chamber section 120a is at a level which is greater than the biasing force in the return spring 193 of the valve mechanism 189, whereby the valve element 191 is forced out of sealing engagement with the restricted bore section 112e (which functions as a "valve seat"), as shown in FIG. 22H. This is the start of the final (third) phase of the continuous forward stroke of the piston member 114 which ends when the piston member 114 reaches its forward position, as delimited by abutment of the forward end 148c of the forward sealing element 148 with the forward end wall 120c of the dosing chamber 120. In this final phase, the metered volume of the liquid in the forward dosing chamber section 120a is dispensed through the restricted bore section 112e, being conveyed along the grooves 191e in the valve member 191 into the forward bore section 112f of the main housing 112, before the valve mechanism 189 is re-closed by the return spring 193 returning the valve member 191 into sealing engagement in the restricted bore section 112e.

The valve mechanism 189 only opens in this final (third) phase, remaining closed at all other times.

The second and third phases can collectively be considered as a "dispensing phase".

In an initial (first) phase of the return, rearward stroke of the piston member 114 in the dosing chamber 120, driven by the return spring 118, the piston member 114 not only moves rearwardly with respect to the dosing chamber 120, but also to the forward sealing element 148 so as to open the one-way valve, as discussed hereinabove. Moreover, a negative pressure (or vacuum) is generated in the headspace being formed in the forward dosing chamber section 120a in front of the rearwardly moving piston member 114. This negative pressure draws more liquid out of the fluid supply 170 and through the open one-way valve into the forward dosing chamber section 120a until the forward sealing element 148 disengages from the forward dosing chamber 120a to enter the step 120s (see FIG. 22I). The provision of the one-way valve on the piston 114 which opens in the initial phase of the return stroke avoids the creation of any hydraulic lock in front of the piston member 114 which could otherwise prevent or inhibit the return stroke.

In a final (second) phase of the rearward stroke of the piston member 114, the piston member 114 moves from an intermediate position, at which the forward sealing element 148 has just been disposed in the step 120s to its rearward position. In this final phase, the liquid is able to be drawn from the rear dosing chamber section 120b directly into the forward dosing chamber section 120a around the outside of the forward sealing element 148, in addition to via the open one-way valve. When the forward sealing element 148 is moving rearwardly in the step 120s, the liquid flows around it via the flutes 120d. Concomitantly, bleeding of the liquid from the forward dosing chamber section 120a to the rear dosing chamber section 120b is via the flutes 120d when the forward sealing element 148 is moving forwardly in the step 120s towards the forward section 120a.

At the end of the return, rearward stroke, the dosing chamber 120 is refilled with liquid. In other words, the volume between the forward lip seal 128a of the rear sealing element 128 and the forward end wall 120c of the dosing chamber 120 is filled. The return stroke may thus be referred to as the "filling phase".

Thus, each cycle of movement of the piston member 114 in the dosing chamber 120, as effected by reciprocal movement between the nozzle assembly and the bottle assembly, comprises the bleeding, dispensing and filling phases.

In each subsequent cycle of movement of the piston member 114, the forward stroke results in another metered volume of the liquid being captured in the forward dosing chamber section 120a and then discharged through the restricted bore section 112e, while the rearward stroke results in liquid being drawn from the fluid supply 170 to refill the dosing chamber 120.

During priming, such subsequent pumping cycles continue until the liquid fills the fluid flow path from the dosing chamber 120 to the fluid outlet 152 (see FIG. 22I). In this regard, the liquid passing through the restricted bore section 112e flows through the forward bore section 112f of the main housing 112, into the fluid dispensement chamber 146 via the apertures 165e in the forward end wall 165b of the cap 165 mounted over the forward end of the main housing 112, into the space around the sealing member 154 by passing through the apertures 197n in the nozzle insert 197 fitted inside the nozzle 116 to enclose the cap 165 and thence into the swirl chamber 153 via the feed channels 153b thereof.

When liquid fills the fluid pathway from the fluid supply 170 to the fluid outlet 152, the forward stroke of the piston member 114 relative to the dosing chamber 120 in the next pumping cycle results in another metered volume of liquid being pumped through the restricted bore section 112e thereby pressurising the liquid pending downstream of the restricted bore section 112e. This pressure in the fluid dispensement chamber 146 results in rearward sliding movement of the cap 165 (and the main housing 112) in the nozzle insert 197 against the return force of the return spring 118 whereby the sealing tip 160 sealingly slides rearwardly in the sealing member 154. This is because the surface area of the sealing cap 165 bounding the fluid dispensement chamber 146 (and hence being acted upon by the pressurised fluid) is greater than that of the nozzle insert 197.

As a result, the elasticity of the sealing member 154 flattens the central part of the forward face 154c of the sealing member 154 back to its original state to open the central chamber 153a and passageway 153c of the swirl chamber 153 (see FIG. 9C). Consequently, a metered volume of the liquid is pumped through the fluid outlet 152 via the swirl chamber 153 for atomisation thereof to make space for the metered volume pumped through the restricted bore section 112e in that forward stroke (see FIG. 22J).

The dynamic seal between the opposing longitudinal sides of the sealing tip 160 and the sealing member 154 prevents liquid under the hydraulic pressure entering the sealing member cavity 154e (FIG. 10) in which the sealing tip 160 is disposed and acting to oppose the central part of the forward face 154c of the sealing member 154 moving back to its original state when released by the sealing tip 160.

The return force of the return spring 118 moves the main housing 112 and sealing cap 165 back (forwardly) to its normal, rest position in the nozzle insert 197 once the return force is greater than the hydraulic pressure in the fluid dispensement chamber 146 so that the sealing tip 160 deflects the sealing member 154 to (re)close the fluid outlet 152.

The sealing member 154 thus protects the liquid inside the fluid dispenser 110 from contamination by contaminants outside of the device 110 entering through the fluid outlet 152 as it only opens during dispensing (i.e. when the fluid dispenser 110 is fired).

The rearward stroke of the same pumping cycle draws liquid from the liquid supply 170 to refill the dosing chamber 120, ready for the next pump cycle.

The device is now fully primed, and each pump cycle thereafter results in a constant metered volume of the liquid being pumped from the fluid outlet 152 until the fluid supply 170 is exhausted.

It will be appreciated that the fluid dispenser 110 configuration is such that there will be no, or substantially no drainback of the liquid pending in the path between the dosing chamber 120 and the fluid outlet 152 as the restricted bore section 112e is sealed shut by the valve mechanism 189 except in the dispensing phase of the forward stroke. Thus, the need to re-prime the device is avoided or substantially alleviated. Moreover, the tip seal arrangement, formed by the sealing member 154 and the sealing tip 160, and the valve mechanism 189 prevent or substantially prevent ambient air being drawn into the fluid dispenser 110 through the fluid outlet 152 by the negative pressure (e.g. vacuum) created in the dosing chamber 120 in the filling phase.

It is also notable that during priming of the fluid dispenser 110, air (and any other gas) in the headspace above the liquid is pumped out of the fluid outlet 152 by the same mechanism as described above for the liquid.

As described previously, the engagement of the forward end wall 165b of the cap 165 with the rear side of the end wall 197c of the nozzle insert 197 limits the length of the sealing tip 160 that is able to project through the nozzle insert 197 onto the rear face of the sealing member 154. In this way, the stress applied by the sealing tip 160 to the sealing member 154 is controlled and so too, therefore, is creep of the sealing member 154 over the lifetime of the dispenser 110. Consequently, in this arrangement the sealing member 154 will be less prone to creep into the swirl chamber feed channels 153b to create a permanent obstruction therein and to lose the elastic/shape memory properties upon which the sealing member 154 relies to open the fluid outlet 152 when the sealing tip 160 is moved rearwardly in use of the fluid dispenser 110, as described hereinabove.

Moreover, the above-described engagement of the sealing cap 165 and the nozzle insert 197 demarcates the forwardmost position of the main housing 112 in the nozzle 116, noting that the nozzle insert 197 is fixed in position in the nozzle 116 through engagement of the nozzle insert feet 197i in the T-shaped cut-outs 116g. This forwardmost position of the main housing 112 in the nozzle 116 is its normal, rest position as a result of the action of the return spring 118. The main housing 112 only moves rearwardly from this rest position when the fluid in the fluid dispensement chamber 146 is pressurised in the dispensing phase of the operational cycle of the fluid dispenser 110. This fixing of the rest position of the main housing 112 in the nozzle 116 ensures that the piston member 114 is able to abut the forward end wall 120c of the dosing chamber 120 in the dispensing phase for reliable metering from the dosing chamber 120, noting that if the main housing 112 was 'floating' in the nozzle 116 so as to be able to be moved further forwardly therein, the piston member 114 would be spaced rearwardly of the dosing chamber forward end wall 120c at the end of the forward stroke of the piston member 114, as demarked by engagement of the roof 176c of the stopper portion 176 with the rear end 116f of the nozzle 116.

It will also be appreciated that the inter-engagement of the sealing cap 165 with the nozzle insert 197 also prevents the piston member 114 being able to push the sealing tip 160 any farther into the sealing member 154 when the piston member 114 contacts the forward end wall 120c of the dosing chamber 120.

FIGS. 7A and 9A show the fluid dispenser 110 in an open (fully extended) position, where the nozzle 116 (and its attached components) is spaced farther from the bottle 170 (and its attached components) than in the rest position shown in FIGS. 7B and 9B. More particularly, in the rest position, the carrier member 195 rests on, or in close proximity to, the roof 176c of the stopper portion 176, whereas in the open position the carrier member 195 is spaced from the stopper portion roof 176c. In the open position, the clips 116b on the runners 116a of the nozzle 116 are at the forwardmost position with respect to the tracks 176m on the stopper portion 176, as shown in FIG. 9A. In the rest position, by contrast, the clips 116b are spaced rearwardly of the forwardmost position, as also shown in FIG. 9B. The ability for the nozzle 116 and bottle 170 to be further separated from the normal rest position provides protection of the fluid dispenser against breakage in the event it is dropped or suffers an impact.

It will be appreciated that the fluid dispenser 110 is able to adopt the open position through, the carrier member 195 being separate from the stopper portion 176. FIG. 7B reveals that in the rest position, the clips 195d of the carrier member 195 are positioned at the rear end of the T-shaped tracks 116g. Forward movement of the nozzle 116 relative to the bottle 170 is only permitted since the carrier member 195 is able to be carried forwardly relative to the bottle 170 with the nozzle 116.

There now follows descriptions of alternative sealing arrangements that could be used in the fluid dispenser 110, with like reference numerals being used to indicate like parts and features with the sealing arrangement in FIGS. 7 to 21.

Figure 24:
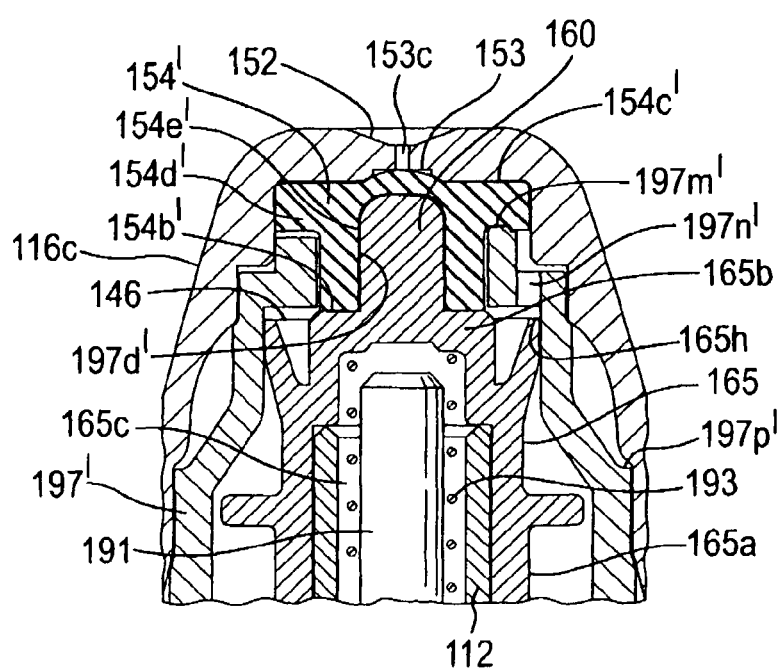
FIG. 24 corresponds to FIG. 10, but shows an alternative tip seal arrangement for the fluid, dispenser of FIGS. 7 to 21.
Figure 25A:
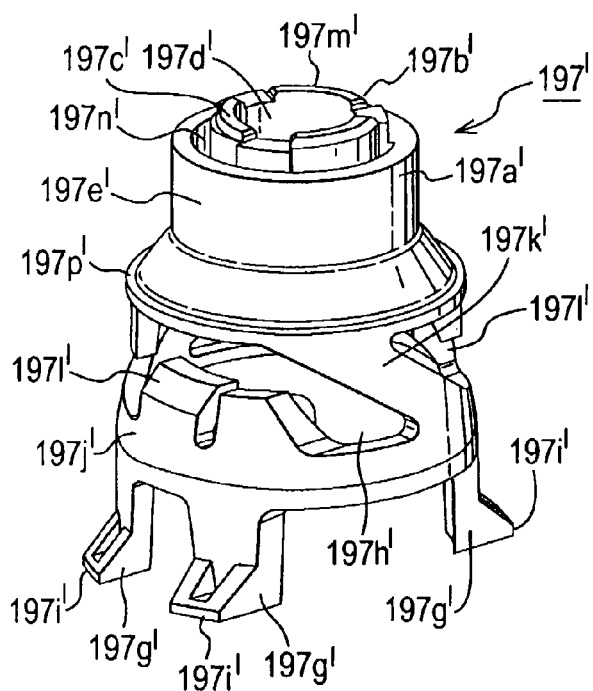
FIGS. 25A and 25B are respectively perspective and cross-sectional side views of the nozzle insert in FIG. 24.
Figure 25B:
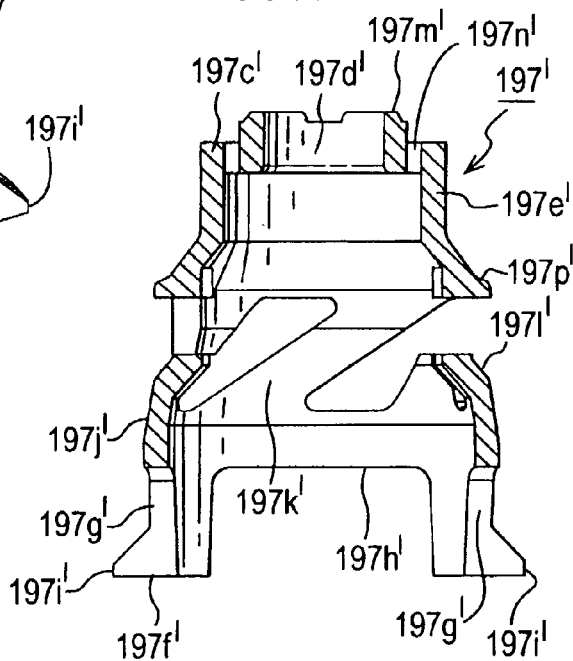

In FIGS. 24 and 25A-B there is shown a first alternative tip seal arrangement that could be used in the fluid dispenser 110. In FIG. 24, the sealing member 154' and nozzle insert 197' are of different shape compared to their counterparts in the fluid dispenser 110 of FIGS. 7 to 21, but function in the same way as their counterparts. However, the forward end wall 165b of the cap 165 is now biased by the return spring 118 into direct contact with the rear face 154b' of the sealing member 154'. This is due to removal of the step or shoulder in the central aperture 197d' of the nozzle insert 197' which supported the sealing member 154 of FIGS. 7 to 21 to allow a lengthened sealing member 154' to pass through into contact with the sealing cap 165. The nozzle insert 197' and sealing member 154' are of the same materials as described for the fluid dispenser 110 of FIGS. 7 to 21.

Figure 26:
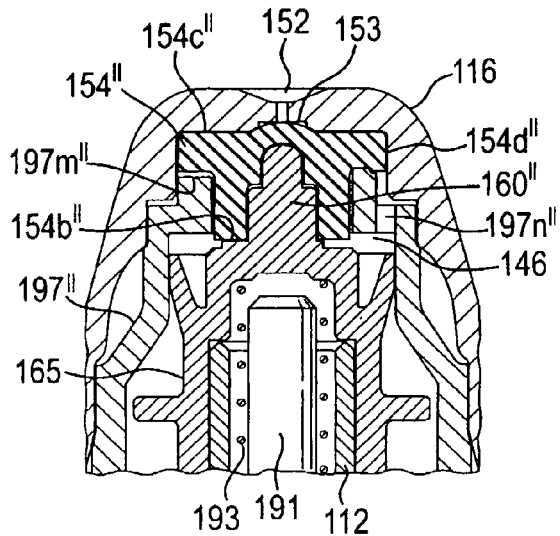
FIG. 26 corresponds to FIG. 10, but shows a further alternative tip seal arrangement.

In FIG. 26 there is shown a second alternative tip seal arrangement that could be used in the fluid dispenser 110 having similarity with the first alternative tip seal arrangement. In this second alternative, the sealing member 154" and nozzle insert 197" are of different shape' to their counterparts in the first alternative of FIGS. 24 and 25A-B, but function in the same way, and are made from the same materials, as those counterparts.

Figure 27:
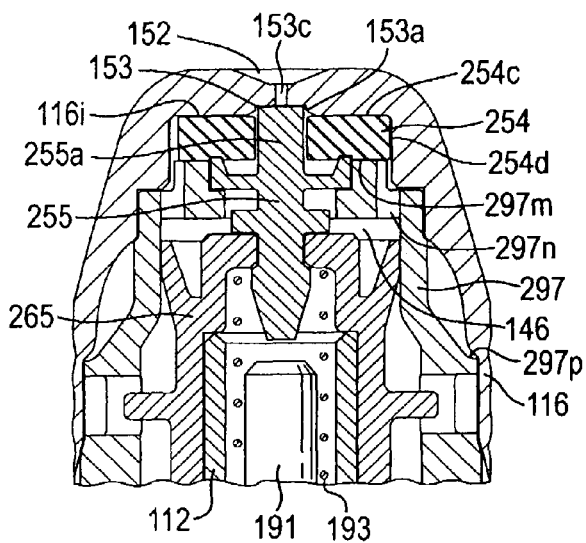
FIG. 27 corresponds to FIG. 10, but shows an alternative sealing arrangement for the fluid dispenser of FIGS. 7 to 21.
Figure 28A:
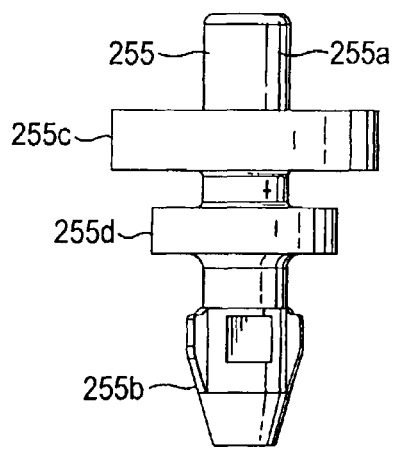
FIGS. 28A and 28B are respectively perspective and cross-sectional side views of the sealing pin in FIG. 27.
Figure 28B:
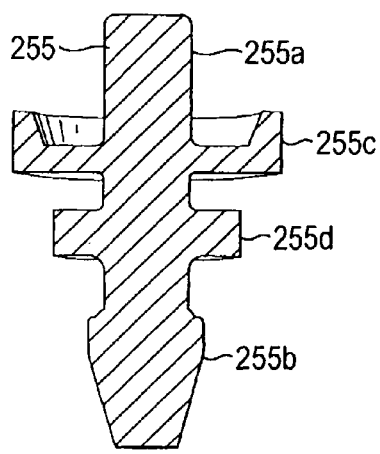
Figure 29A:
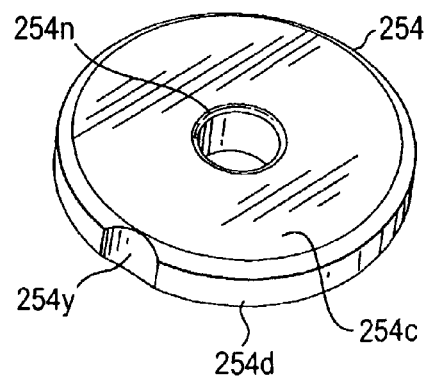
FIGS. 29A and 29B are respectively perspective and cross-sectional side views of the backing plate in FIG. 27.
Figure 29B:
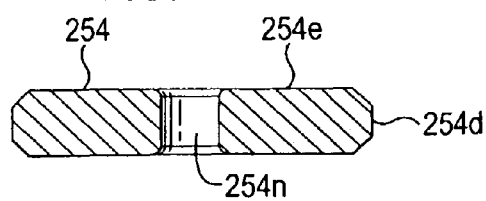
Figure 30:
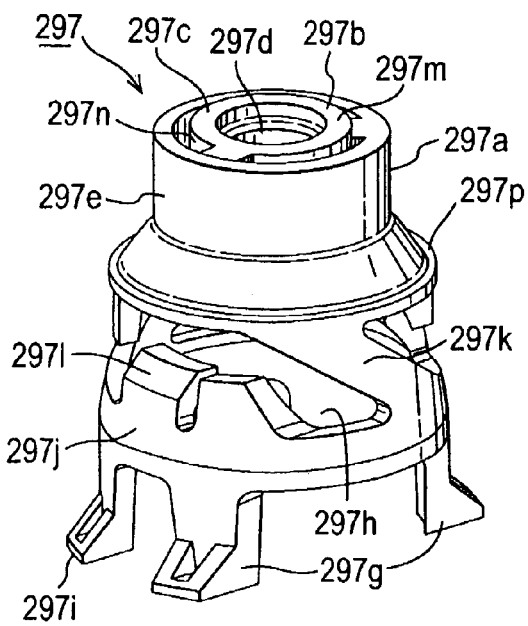
FIGS. 30A and 30B are respectively perspective and cross-sectional side views of the nozzle insert in FIG. 27.
Figure 30:
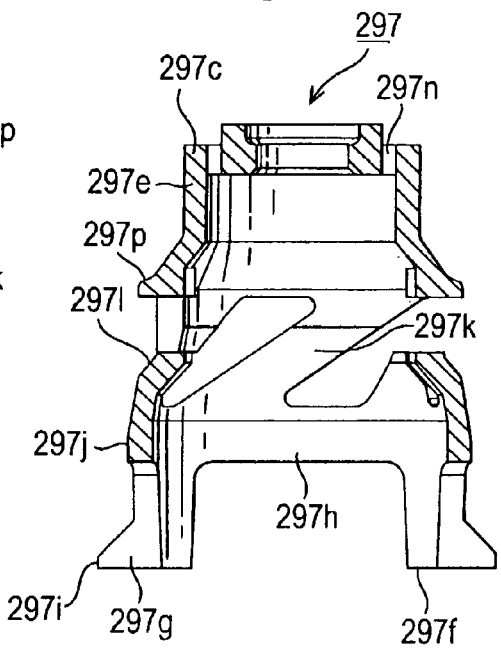
Figure 31:
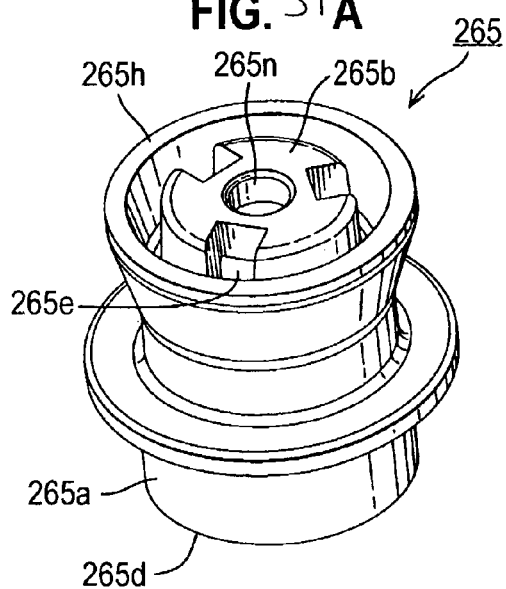
FIGS. 31A and 31B are respectively perspective and cross-sectional side views of the forward sealing element in FIG. 27.
Figure 31:
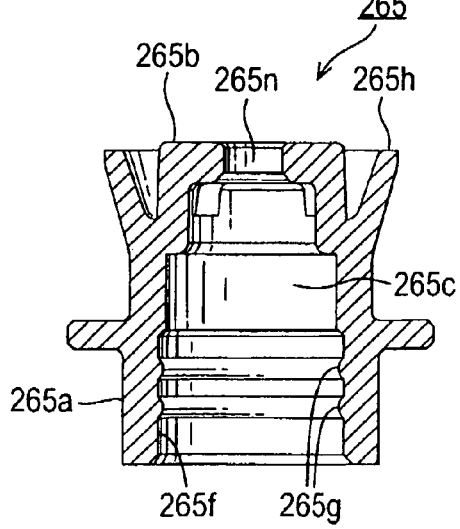

In FIG. 27 there is shown a different type of sealing arrangement for the fluid dispenser 110, with FIGS. 28 to 31 showing the components for this sealing arrangement.

In place of the elastic sealing member 154 there is provided an annular backing plate 254 (FIGS. 29A-B), made from a plastics material. In this embodiment, the backing plate is injection moulded from polypropylene (PP). The forward face 254c of the backing plate 254 is held by a modified nozzle insert 297 (FIGS. 30A-B) in sealing engagement with the forward end wall 116i of the nozzle 116 so as to seal over the swirl chamber feed channels 153b whereby any liquid travelling up the gap between the side face 254d of the backing plate 254 and the nozzle 116 has to pass into the swirl chamber feed channels 153b. It will be seen that a longitudinal groove or flute 254y is provided in the plate side face 254d as a fluid flow path between the plate 254 and the nozzle 116.

A sealing pin 255 (FIGS. 28A-B) is seated on the nozzle insert 297 so that a forward sealing section 255a of the sealing pin 255 protrudes through the through-hole 254n in the backing plate 254 and into the central chamber 153a of the swirl chamber 153 to sealingly close the passageway 153c. Thus, the sealing pin 255 functions similarly to the elastic sealing member 154.

As shown in FIG. 27, the sealing pin 255 has an enlarged, rear end 255b of tapering profile which is held captive in a through-hole 265n in the forward end wall 265b of a modified cap 265 (FIGS. 31A-B) so that the sealing pin 255 moves in unison with the main housing 112 to which the cap 265 is fixed.

It will therefore be appreciated that the return spring 118 acts on the main housing 112 to bias the sealing pin 255 into sealing engagement over the swirl chamber passageway 153c. Moreover, during the dispensing phase of the forward stroke of the piston member 114 in the dosing chamber 120, the hydraulic pressure produced in the fluid dispensement chamber 146 results in the cap 265 moving rearwardly against the return spring force, and in so doing moves the sealing pin 255 rearwardly so as to open the swirl chamber passageway 153c for release of the metered volume of liquid.

It will be observed that the sealing pin 255 is provided with forward and rear annular flanges 255c, 255d. The rear flange 255d delimits the insertion of the sealing pin 255 into the cap through-hole 265n. The forward flange 255c seals against the rear side of the backing plate 254.

It will further be observed that the valve element 191 of the valve mechanism 189 in the main housing 112 is provided with an abbreviated length to accommodate the sealing pin 255.

The sealing pin 255 in this embodiment is injection moulded from low density polyethylene (LDPE) or high density polyethylene (HDPE), but other functionally equivalent plastics materials could be used.

The modified cap 265 and modified nozzle insert 297 are made from the same materials are described for the corresponding parts in the fluid dispenser 110 of FIGS. 7 to 21. The modified nozzle insert 297 may also have a castellated forward end wall 297c, as in the other illustrated nozzle inserts 197; 197'; 197".

The arrangement of FIGS. 27-31 could in turn be modified so that the sealing pin 255 is integrally formed (e.g. moulded) as part of the cap 265. The rear annular flange 255d and/or the rear end 255b may then be omitted. Additionally, or alternatively, the forward annular flange 255c may be omitted and the pin 255 or the inner circumferential surface of the sealing member 254 may 136 provided with a lip seal to seal therebetween. This latter option could be used as another independent variant of the tip seal arrangement of FIG. 27, i.e. when the pin 255 is a separate component from the cap 265 as otherwise shown in FIG. 27.

Referring now to the fluid dispenser 310 shown in FIGS. 22A-J, this functions in the same way as the fluid dispenser 110 of FIGS. 7 to 21. The sealing tip 360, sealing member 354, forward sealing element 328 and stopper portion 376 are of a slightly different structure to the corresponding components in the fluid dispenser 110. More particularly, the tip seal arrangement is of the alternative type described with reference to FIG. 26. Most notably, however, is the absence of a carrier member for the return spring 318 in the fluid dispenser 310. It will be seen from FIG. 22A that an annular retaining wall 376t projects forwardly from the roof 376c of the stopper portion 376 (see also FIG. 37). As further shown in FIG. 22A, the return spring 318 is carried on the stopper portion roof 376c and extends forwardly to the annular flange 312b of the main housing 312 through the annular gap formed between the annular retaining wall 376t and the main housing 312. It will also be appreciated that the fluid dispenser 310 does not have an open position, like the fluid dispenser 110, for improving protection against damage if dropped or otherwise impacted.

FIG. 32 shows a further fluid dispenser 410 which corresponds to the fluid dispenser 110 of FIGS. 7 to 21, other than in two notable respects. Firstly, the tip seal arrangement is of the alternative type described with reference to FIGS. 24 and 25A-B. Secondly, a modified forward sealing element 448 is fixed on the piston 414. The forward sealing element 448 in this embodiment is fixed against movement on the piston 414 and provides no through channel for fluid to flow therethrough from the rear side to the forward side, as in the fluid dispenser 110. The modified forward sealing element 448 functions like the forward sealing element 148 in the fluid dispenser 110 in the forward stroke of the piston 414 to its forward position; i.e. the forward lip seal 448a slidingly seals against the forward dosing chamber section 420a so that a metered dose of the fluid is pumped through the valve 489. However, on the return rearward stroke of the piston 414 to its rear position, the pressure difference created across the resilient forward lip seal 448a of the forward sealing element 448 causes the forward lip seal 448a to flex or deform inwardly to create an annular space thereabout for the fluid in the dosing chamber 420 to flow forwardly past the forward lip seal 448a into the forward dosing chamber section 420a in front of the retreating piston 414. Thus, the resiliency of the forward lip seal 448a allows the forward sealing element 448 to function as a one-way valve which opens in the initial phase of the return stroke thereby avoiding the creation of any hydraulic lock in front of the piston member 414 which could otherwise prevent or inhibit the return stroke.

If air happens to be trapped in the forward section 420a of the dosing chamber 420, for instance in the annular space in the forward sealing element 448 behind the lip seal 448a, the lip seal 448a may stay in sliding sealing contact with the wall of the forward dosing chamber section 420a during the rearward, return stroke of the piston member 414 and no hydraulic lock results due to the presence of the afore-mentioned air. In other words, there is no deflection of the lip seal 448a. When the lip seal 448a passes into the step 420s, the fluid is then drawn by the pressure difference into the forward dosing section 420a, e.g. through the at least one axial flute 420d.

However, preferably no air, or substantially no air, is trapped in the dosing chamber forward section 420a so that the forward lip seal 448a acts as a one-way valve.

In the rest position of the dispenser 410, the forward lip seal 448a is in contact with that section of the dosing chamber wall in which the axial flute(s) 420d is defined (cf. FIG. 9B). However, the dispenser 410 may be adapted so that at rest the forward lip seal 448a is spaced rearward of the flute(s) 420d so as to be spaced away from the dosing chamber wall.

Figure 33:
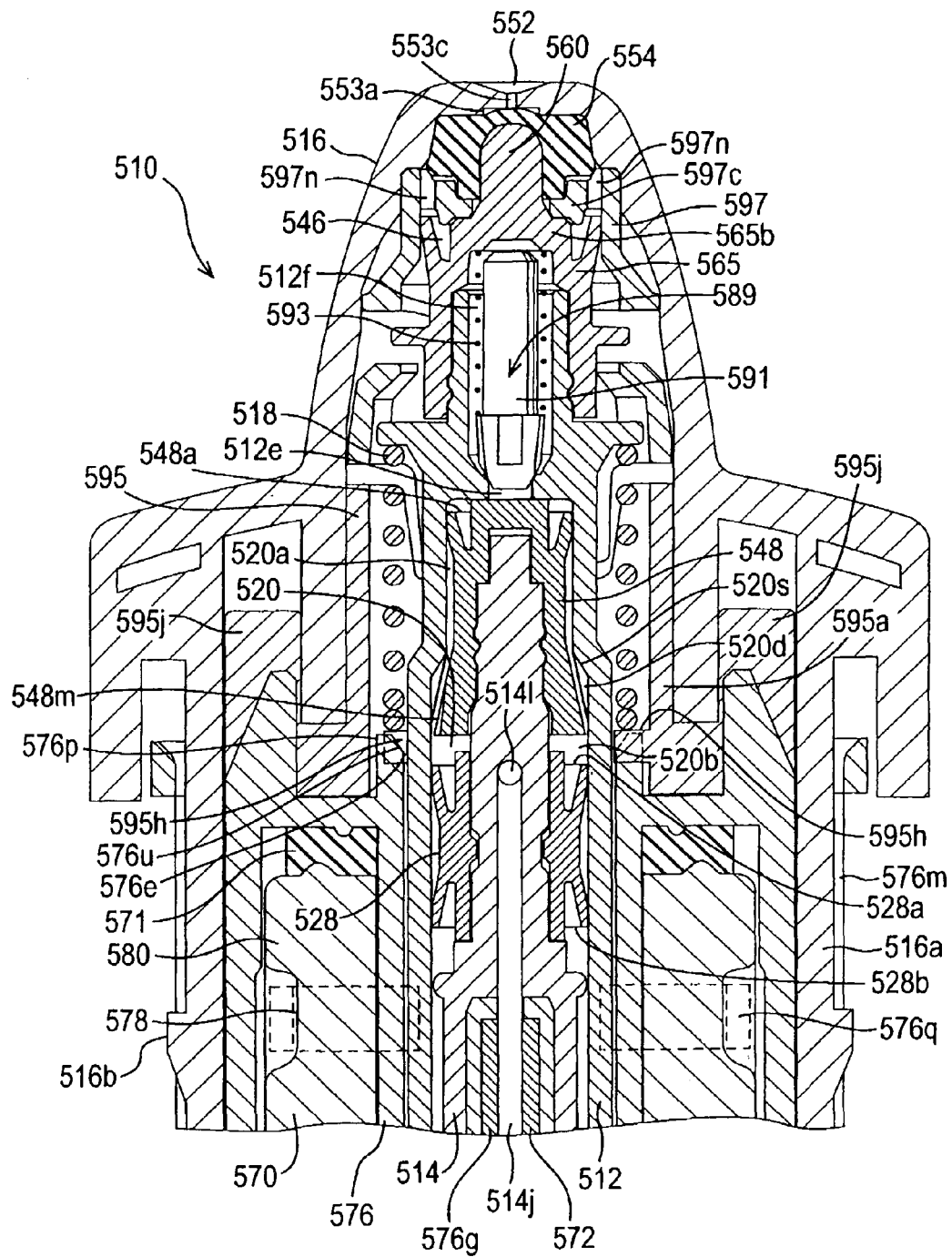
FIG. 33 is a cross-sectional side view of yet another modified version of the fluid dispenser of FIGS. 7 to 21 for use in the third to fifth fluid dispensing devices, shown in its fired position, but with the tip seal arrangement having reclosed at the end of dispensing.
Figure 33:
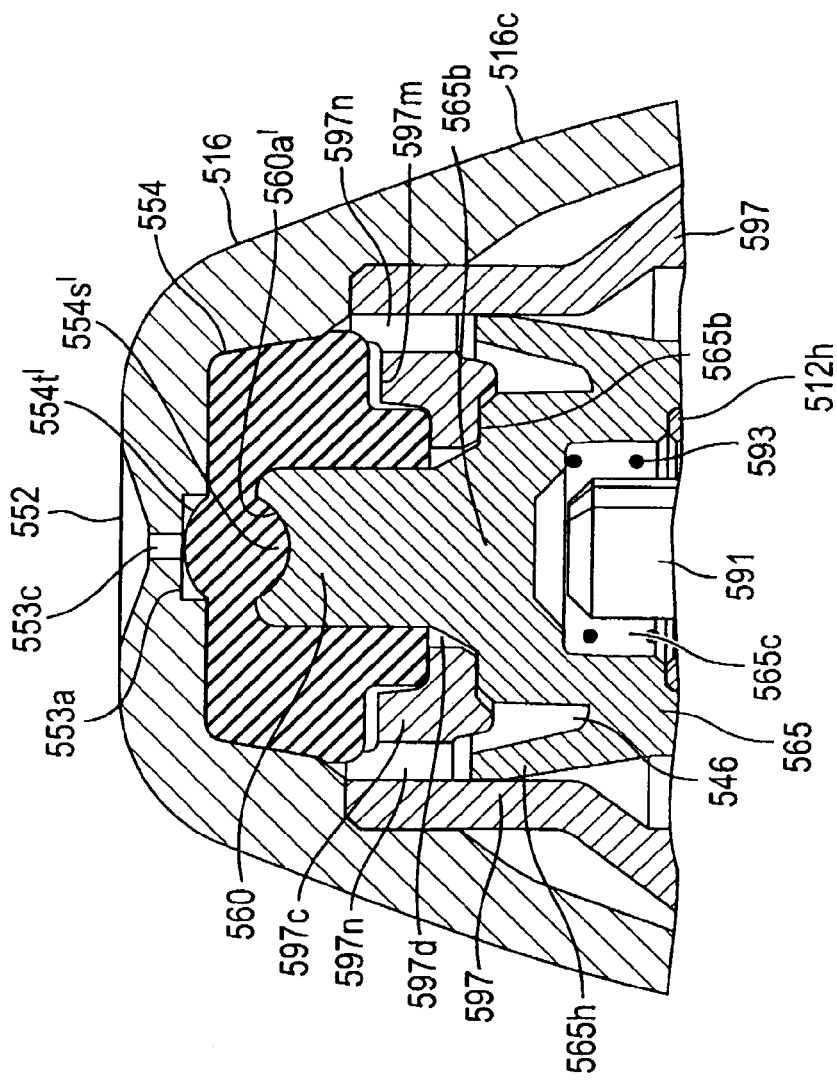

FIG. 33 shows another alternative fluid dispenser 510 which functions in the same way as the fluid dispenser 410 of FIG. 32, with like features being denoted by like reference numbers and the differences now being elaborated upon.

Figure 34:
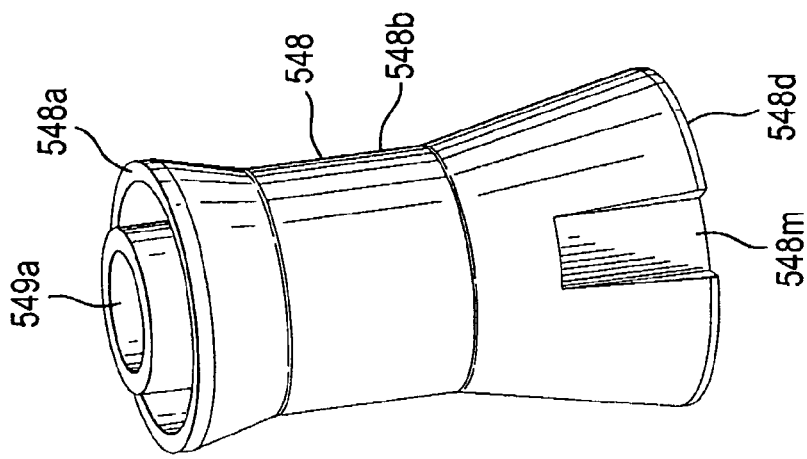
FIG. 34 is a perspective view of the forward sealing element of the fluid dispenser of FIG. 33.

Firstly, as also shown in FIG. 34, the forward sealing element 548 has a subtly different shape, being flared at its rear end 548d and provided with at least one axial groove or flute 548m in its outer peripheral surface which extends forwardly from the rear end 548d. The flared rear end 548d prevents the main housing 512 catching on the forward lip seal 528a of the rear sealing element 528 as it moves relatively rearwardly over the piston member 514 in assembly of the fluid dispenser 510. In this regard, the forward lip seal 528a of the rear sealing element 528 is provided with a rounded lip (not shown). The outer diameter of the rear end 548d of the forward sealing element 548 is at least the same as the inner diameter of the forward lip seal 528a of the rear sealing element 528. Thus, when the main housing 512 slides relatively rearwardly over the piston member 514 in assembly, the rear end 548d of the forward sealing element 548 guides the rear end of the main housing 512 onto the rounded surface of the forward lip seal 528a of the rear sealing element 528, which in turn guides the rear end of the main housing 512 to slide thereover.

The rear lip seal 528b may also be provided with a rounded lip to form a symmetrical rear sealing element 528 which may be mounted on the piston member 114 either way round for simplifying assembly. Alternatively, just the forward lip seal 528a may have a rounded lip, with the rear lip seal 528a being, e.g., square cut.

Although the rear end 548*d* of the forward sealing element 548 is still spaced from the inner circumferential surface of the dosing chamber 520, as shown in FIG. 33, albeit less than in the hitherto described embodiments, the axial flute 548*m* reduces the resistance to fluid flow around the rear end 548*d* of the forward sealing element 548 on movement of the piston member 514 in the dosing chamber 520.

Notwithstanding these structural difference's, the rear and forward sealing elements 528, 548 still function in the same way as their counterparts in the fluid dispenser 410 of FIG. 32.

Secondly, the stopper portion 576 has a series of minor protrusions 576*p* which, unlike the minor roof protrusions of the fluid dispenser 410 (see FIGS. 15A and 15B), form extensions of the roof opening 576*e* and have a tapered lead-in surface 576*u* to guide the main housing 512 into the roof opening 576*e* in assembly of the fluid dispenser 510.

Thirdly, the carrier member 595 for the return spring 518 has a series of radially inwardly-directed protrusions 595*h* at the rear end of the annular body 595*a* which interfit with the stopper portion minor protrusions 576*p* to prevent rotation of the carrier member 512 relative to the stopper portion 576 and also to align the carrier member 595 in the correct angular orientation so that the clips thereof (not shown) will clip into the T-shaped tracks (not shown) in the nozzle 516, as previously described for the fluid dispenser 110 of FIGS. 7 to 21. Conveniently, there are twice as many carrier member protrusions 595*h* as stopper portion minor protrusions 576*p*, with the carrier member protrusions 595*h* arranged into pairs. The carrier member protrusions 595*h* in each pair are located on opposing sides of one of the stopper portion minor protrusions 576*p*. As shown, the return spring 518 is supported on top of the carrier member protrusions 595*h*.

The carrier member 595 further has a pair of diametrically opposed arms 595*j* extending radially outwardly from the annular body 595*a* at its rear end.

Fourthly, the forward end wall 597*c* of the nozzle 597 has a subtly different geometry to reduce the dead volume in the dispenser 510, in particular in the fluid dispensement chamber 546.

Fifthly, the at least one axial flute 520*d* has a different geometry than that in FIG. 32 (which in turn corresponds to that in FIGS. 7 to 21 and 22). In this embodiment, the at least one flute 520*d* is arranged such that, when the dispenser 510 is at rest, the forward lip seal 548*a* is located adjacent the at least one flute 520*d*, but spaced away therefrom; i.e. there is an annular space around the lip seal 548*a* when it is at its rest, rearward position in the dosing chamber 520. In this way, the potential for creep of the forward lip seal 548*a* into the at least one flute 520*d* is avoided.

In this embodiment, the sides edges of the at least one flute 520*d* are angled to the longitudinal axis, rather than stepped as in the previous embodiments. The side edges of the at least one flute 520*d* may form an acute angle to the longitudinal axis, for instance in the range of 8° to 12°, such as 10°, and provide a lead-in surface to guide movement of the forward lip seal 548*a* into the forward dosing chamber section 520*a* on the forward stroke of the piston member 514. The floor of the at least one flute 520*d* may form a steeper acute angle to the longitudinal axis, for instance in the range of 15° to 25°, such as 20°.

FIG. 35 shows an alternative tip seal arrangement for the fluid dispenser 510. Like the dispenser 110 of FIGS. 7 to 21, the extent to which the sealing tip 560 of the cap 565 presses against the sealing member 554 is controlled through the inter-engagement of the forward end wall 565*b* with the rear side of the end wall 597*c* of the nozzle insert 597.

It will be observed that the sealing tip 560 in this embodiment has a concave form through provision of a recess 560*a'* therein. The sealing member 554 is formed (e.g. moulded) with a rear bulge 554*s'* on its rear side to fit in the recess 560*a'*. Moreover, the sealing member 554 is formed (e.g. moulded) with a forward bulge 554*t'* on its forward side to close the fluid outlet 552. When the fluid dispenser 510 is in its normal, rest state, the forward bulge 554*t'* is forced to seal against the fluid outlet passageway 553*c* by the force applied by the sealing tip 560 to the rear bulge 554*s'*. However, when the sealing cap 560 is forced rearwardly by the increased fluid pressure created in the fluid dispensement chamber 546 as the piston member 514 pumps a metered volume of fluid through the one-way valve (see 589, FIG. 33), the force applied to the rear bulge 554*s'* is released therefore enabling the forward bulge 554*t'* to relax rearwardly and open the fluid outlet passageway 553*c*. In effect, in the normal, rest position the sealing tip 560 compresses the rear bulge 554*s'* and in so doing pushes the forward bulge 554*t'* outwardly. When the sealing tip 560 moves rearwardly, both bulges 554*s'*, 554*t'* are able to move back towards their rest state due to the inherent bias of the material (e.g. a thermoplastic elastomer, such as EPDM) from which the sealing member 554 is made, resulting in a space forming between the sealing member 554 and the fluid outlet passageway 553*c*, whereby a metered volume of fluid is able to be pumped from the fluid outlet 552, via the swirl chamber 553, as an atomised spray.

In yet another alternative tip seal arrangement, not shown, the rear bulge 554*s'* may be omitted and the sealing tip 560 used to push the forward bulge 554*t'* outwardly into sealing engagement with the fluid outlet passageway 553*c*. The sealing tip 560 in this case may also be modified to have a convex free end, such as in the fluid dispensers in FIGS. 7 to 33.

These arrangements using a forward bulge 554*t'* in the sealing member 554 concentrate the tip forces in the centre of the sealing member 554, where the sealing of the fluid outlet passageway 553*c* is needed, and reduce the tip forces applied to the sealing member 554 over the swirl chamber feed channels, thereby reducing the likelihood of these channels being occluded (e.g. by creep of the sealing member 554).

In FIGS. 36A and 36B there is shown a modified stopper portion 676 for use in the afore-described fluid dispensers. This stopper portion 676 corresponds closely to that of FIGS. 15A and 15B, but is provided with just two minor protrusions 676*p*, each forming a radial extension from one of the main protrusions 676*n*.

Figure 37:
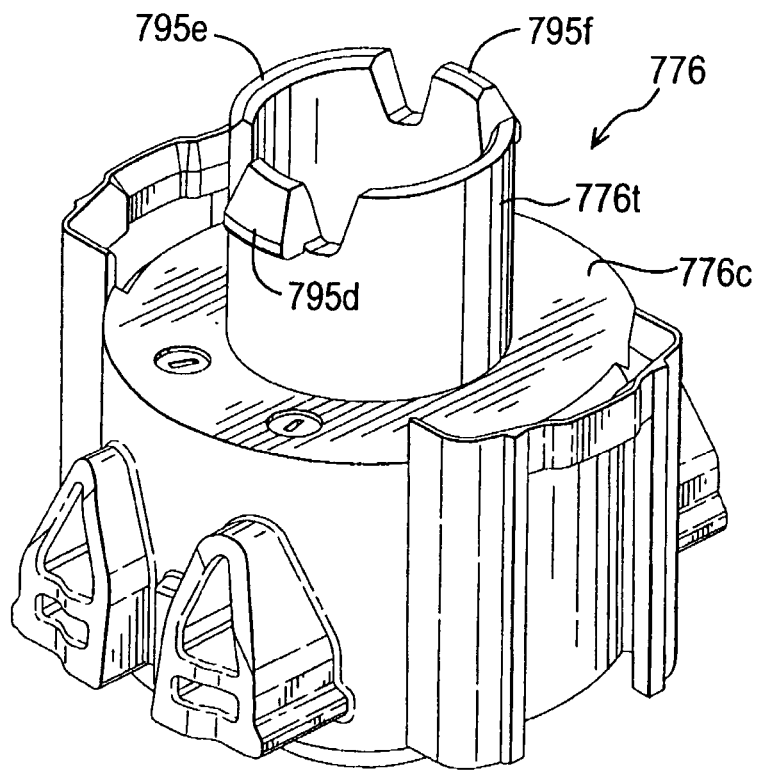
FIG. 37 is a perspective view of a second alternative stopper portion.

FIG. 37 shows a further modified stopper portion 776 for the afore-described fluid dispensers in which the carrier member for the return spring is formed as an integral part 776*t* of the stopper portion 776, preferably integrally formed therewith. It will be appreciated that use of such a stopper portion 776 precludes the associated fluid dispenser having the open (fully extended) position achieved with a separate carrier member, as in, for example, the fluid dispenser 110 of FIGS. 7 to 21.

Figure 39:
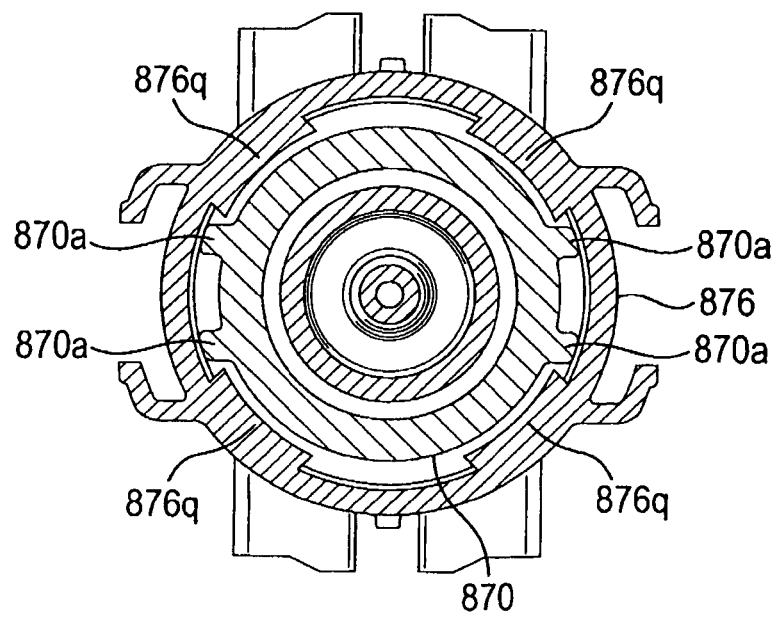
FIG. 39 is a sectional plan view of the bottle of FIG. 38 in a stopper portion.
Figure 38:
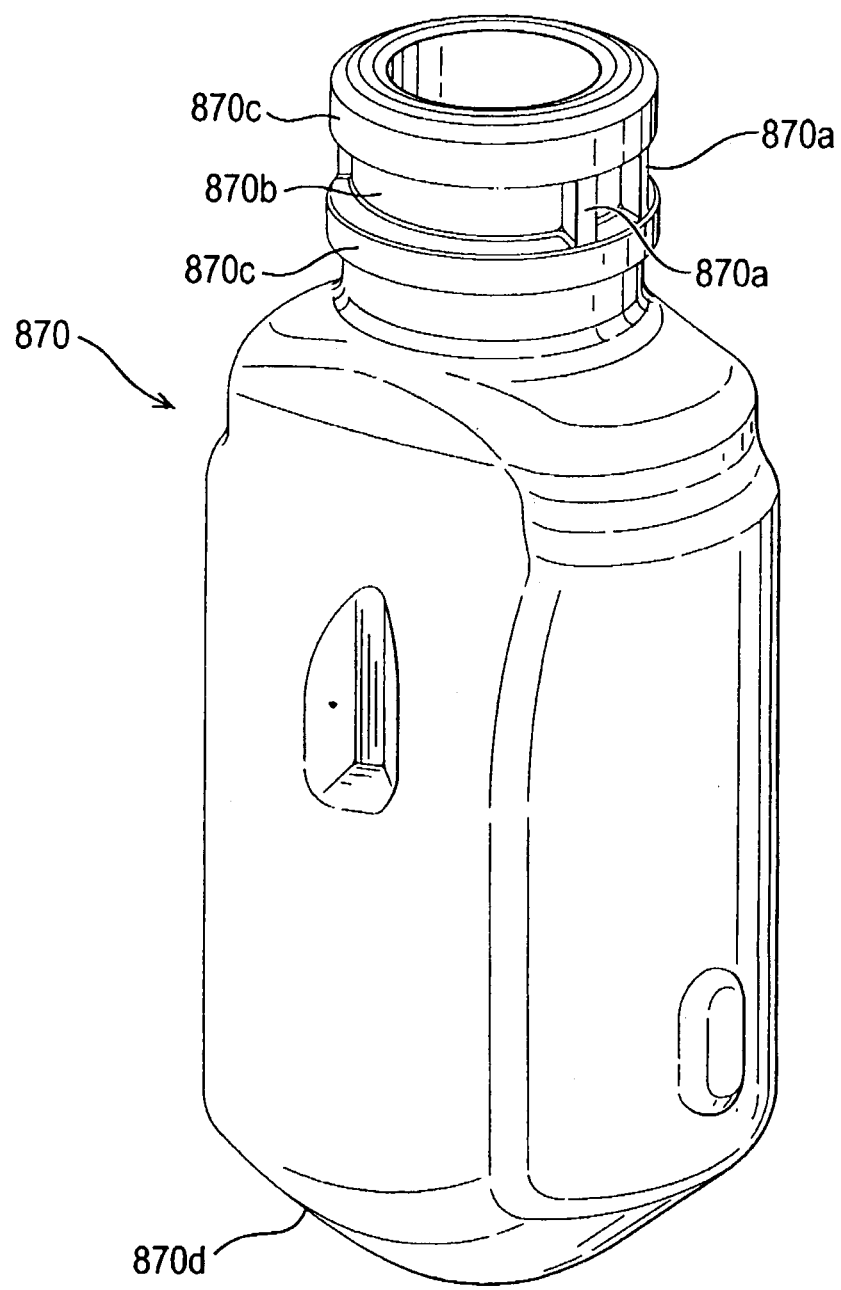
FIG. 38 is a perspective view of a bottle for use in the fluid dispensers herein.

FIGS. 38 and 39 show a bottle 870, preferably of plastic, for use in any of the foregoing fluid dispensers. The bottle 870 is provided with anti-rotational features, here two diametrically-opposed pairs of axial ribs 870*a* which are located in a groove 870*b* defined between a pair of axially spaced-apart circumferential beads 870*c*, to prevent rotation of the bottle 870 in the stopper portion 876 mounted thereon. As shown in FIG. 39, the internal surface of the stopper portion 876 is also provided with anti-rotational features, here the angular segments of the circumferentially-oriented bead 876*q*, which co-operate with the bottle anti-rotational features 870*a* to prevent relative rotation therebetween. Thus, the angular orientation of the bottle 870 relative to the features of the stopper portion 870 can be pre-set in the assembly of the fluid dispenser. It will also be appreciated that the annular segments 876*q* fit into the circumferential groove 870*b* to axially locate the bottle 870 relative to the stopper portion 876.

It will be noted that the bottle 870 has a tapered bottom 870*d*, here of V-section, into which the inlet of the supply tube (not shown) extends. In this way, all or substantially all of the fluid will be drawn from the bottle 870, unlike the case where the bottle has a flat bottom. A clip-on carrier (not shown) may be provided to allow the bottle 870 to stand upright on a production line.

In a modification to the above-described embodiments, not shown, the bottle seal may be omitted and a bore seal formed between the bottle neck and the inner annular skirt of the stopper portion.

In another modification to the above-described embodiments, not shown, the rear open end of the nozzle may be chamfered to provide a lead-in or guide surface for guiding insertion of the dispenser components thereinto.

In another modification to the above-described embodiments, not shown, the sealing cap (e.g. the sealing tip) may be connected to the sealing member so that when the sealing tip is moved rearwardly relative to the nozzle insert, at least the central portion of the sealing member sealing the fluid outlet is pulled rearwardly therewith to open the fluid outlet for dispensement of the metered volume of fluid.

Figure 40:
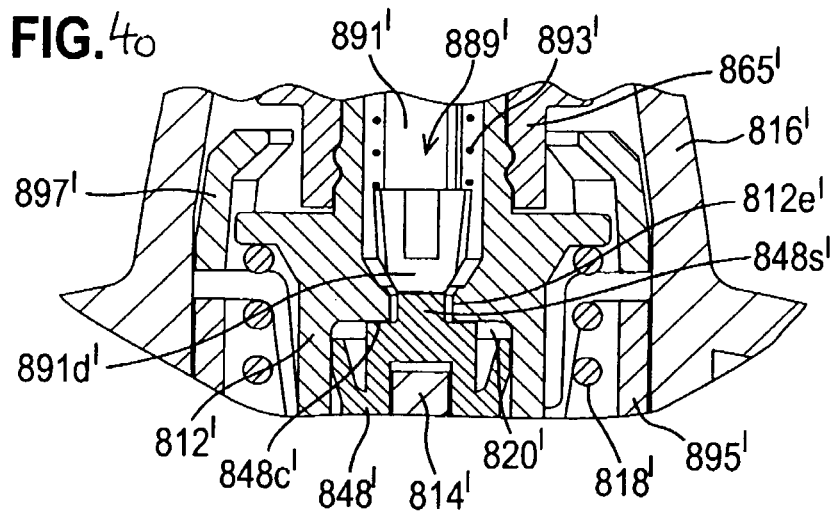
FIG. 40 is a fragmentary view showing an alternative configuration for the piston member and valve element of the fluid dispenser of FIGS. 6 to 21, 22, 32 or 33.
Figure 41:
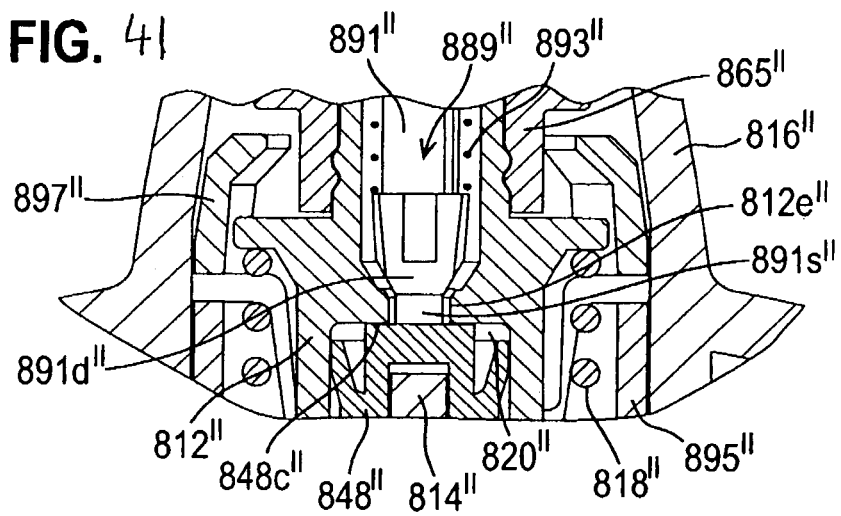
FIG. 41 is a fragmentary view showing another alternative configuration for the piston member and valve element of the fluid dispenser of FIGS. 7 to 21, 22, 32 or 33.

FIG. 40 shows a further modification for any of the previously described fluid dispensers 110; 310; 410; etc. in which the forward end 848*c*' of the forward sealing element 848' has a forwardly extending projection or spigot 848*s*' of length to project into the restricted bore section 812*e*' in the main housing 812' when the piston member 814' is at its forwardmost position in the dosing chamber 820' and thereby prop up the valve member 891' so as to stop the one-way valve 889' reclosing under the action of the return spring 893' when the fluid pressure in front of the piston member 814' drops. In this way, the one-way valve 889' is only able to reclose once the piston member 814' has moved sufficiently rearwardly back towards its rest position to remove the spigot 848*s*' from the restricted bore section 812*e*', for instance rearward movement by 0.1-0.2 mm. By holding the one-way valve open 889' longer, it is believed this will prevent or inhibit the formation of fluid bubbles over the fluid outlet on the nozzle 816' after a dispensing cycle by giving time for pressure inside the dispenser to be relieved at the end of the forward stroke of the piston member. Of course, alternative ways of holding the one-way valve 889' open at the end of the forward stroke of the piston member 814' can be envisaged, for instance, as shown in FIG. 41, having a projection 891*s*''' on the rear end 891*d*''' of the valve member 891". Such a projection on the valve member may be instead of, or in addition to, a projection 848*s*' on the forward sealing element. The piston member could also carry a projection.

One of the benefits of the tip seal arrangements disclosed herein, additional to those previously documented, is that they provide a commitment feature to the fluid dispenser, in that a higher operating force (the "commitment force") is required at the start of the dispensing cycle to create the fluid pressure to overcome the sealing force applied to the sealing member by the sealing tip. Once the tip seal arrangement is opened, the commitment force is released to produce fast release of the fluid through the fluid outlet. This assists in providing accurate metering and reproducible fluid properties in each metered volume dispensed, such as droplet size distribution.

The afore-described fluid dispenser embodiments may be modified to include one or more of the components or features of the other embodiments. Moreover, the materials described for making a component of one embodiment may also be used for the corresponding component of the other embodiments.

The sealing arrangement at the fluid outlet 152; 352; 452 etc of the fluid dispensers 110; 310; 410 etc acts to prevent or inhibit the ingress of microbials and other contaminants into the dispenser 110; 310; 410 etc through the fluid outlet 152; 352; 452 etc, and hence into the dosing chamber 120; 320; 420 etc and ultimately the bottle/reservoir of the fluid. Where the fluid is a liquid medicament formulation, e.g. for nasal administration, this enables the formulation to be free of preservatives or, perhaps more likely, to be a preservative-sparing formulation. In addition, the seal acts to prevent the pending dose of the fluid in the dosing chamber from draining back into the supply or reservoir when the dispenser is in its rest configuration between actuations: This avoids or reduces the need for the dispenser to be primed for its next usage (priming then only effectively being required for the very first usage of the fluid dispenser so as to fill the dosing chamber, but not after the first usage).

In a modification of the fluid dispensers 110; 310; 410 etc herein, a sealing tubular sleeve, e.g. in the form of a gaiter, may be placed over the fluid dispenser so that it is sealed at one (rear) point (e.g. at or near a rear sleeve end) to the outer surface of the stopper portion 176; 376; 476 etc or fluid supply 170; 370; 470 etc and at another (forward) point (e.g. at or near a forward sleeve end) to the outer surface of the nozzle 116; 316; 416 etc. The material for the sealing sleeve is selected to be impervious to microbials and other contaminants, as are the seals formed between the sleeve and the dispenser parts. Suitable materials and seal techniques would be known to the skilled reader. Such a sealing sleeve would further protect the dispensers from microbial and other contaminant ingress thereinto. It would also allow the sealing tolerances inside the dispensers (i.e. other than the tip seal arrangement and the bottle seal 171; 371; 471 etc) to be reduced, since these seals (e.g. 128*a,b*/328*a,b*/428*a,b*; 165*h*; 365*h*/465*h*; 197*p* etc) would then be the second line of defense against ingress other than through the dispensing outlet 152; 352; 452 etc. The sleeve would need to accommodate the movement of the attached dispenser parts towards and away from one another, e.g. be expandable and/or contractible or have a length of sleeve material between the seal points at the maximum distance of separation thereof which is not stretching at that maximum distance, e.g. by having an excess length of sleeve material between the seal points. Slack in the sleeve material may therefore occur between the sleeve seal points when the dispenser parts are moved towards one another in the firing phase. The use of such a sealing sleeve would find use in other dispensers having one (e.g. rear) part which moves relative to another (e.g. forward) part to actuate the dispenser. The sealing sleeve would be sealed to each part.

The invention claimed is:

1. A device for dispensing a substance having:
   a dispensing outlet from which the substance is dispensable,
   a housing in which a dispensing member is able to be mounted for movement in a dispensing direction from a first position to a second position, said movement, in use, causing the substance to be dispensed from the dispensing outlet, and
   an actuator mechanism for moving the dispensing member, when present, from the first position to the second position, said actuator mechanism having:

a first member mounted for movement in a predetermined direction, and a second member pivotally mounted on the first member for pivotal movement in a predetermined pivotal sense, wherein the second member has plural pairs of arms extending therefrom, wherein the actuator mechanism is adapted such that:

movement of the first member in the predetermined direction results in the second member moving with the first member and one arm of each pair of arms engaging with a pusher surface so as to effect the pivotal movement of the second member in the predetermined pivotal sense, and said pivotal movement of the second member in the predetermined pivotal sense results in the dispensing member, when present, moving from the first position to the second position.

2. The device of claim 1, wherein the dispensing member is a dispensing container for containing a supply of the substance.

3. The device of claim 1, wherein the dispensing outlet is co-axially arranged with the dispensing direction.

4. The device of claim 1, wherein the dispensing member has a dispensing mechanism which is adapted to deliver a dose of the substance from the dispensing outlet in response to the dispensing member being moved from the first position to the second position by the actuator mechanism.

5. The device of claim 1, wherein the dispensing outlet is in a nozzle sized and shaped for insertion into a nostril of a human or animal body.

6. The device of claim 1, wherein the dispensing outlet is part of a housing, the housing adapted to receive therein the dispensing member.

7. The device of claim 1, wherein the second member is a rigid member.

8. The device of claim 1, wherein the arms extend in different directions.

9. The device of claim 1, wherein the angle formed between the arms is no greater than 90 degrees.

10. The device of claim 1, wherein one of the arms of each pair of arms of the second member is a carrier arm for carrying the dispensing member from the first position to the second position when the second member pivots in the predetermined sense.

11. The device of claim 1, wherein the second member is a bell crank.

12. The device of claim 1, wherein the actuator mechanism comprises a biasing force for biasing the second member to pivot in an opposite sense to the predetermined pivotal sense.

13. The device of claim 12, comprising a spring element to provide the biasing force.

14. The device of claim 13, wherein the spring element is comprised in the second member.

15. The device of claim 14, wherein the spring element is an integrally formed part of the second member.

16. The device of claim 14, wherein the spring element is disposed on a mounting section of the second member which is pivotally mounted to the first member.

17. The device of claim 1, for dispensing a pharmaceutical substance.

18. The device of claim 1, wherein the dispensing direction is along an axis and the predetermined direction is generally transverse to the axis.

19. The device of claim 18, wherein the predetermined pivotal sense is about a pivot axis which is generally normal to the axis.

20. The device of claim 1, wherein the first member is pivotally mounted in the device.

21. The device of claim 20, wherein the or each pusher surface is provided by a housing of the device on which the first member is mounted.

22. The device of claim 20, wherein the first member is pivotally movable in the predetermined direction in a sense which is opposite to the predetermined pivotal sense.

23. The device of claim 1, wherein the or each pusher surface is provided by a housing of the device on which the first member is mounted.

24. The device of claim 23, wherein the predetermined direction is a movement of the first member into the housing.

25. The device of claim 1, including a housing and a dispensing member mounted in the housing for movement in the dispensing direction.

26. The device of claim 1, wherein the actuator mechanism is finger-operable.

27. The device of claim 1, wherein the other arm of each pair of arms of the second member is a carrier arm for carrying the dispensing member from the first position to the second position when the second member pivots in the predetermined sense.

28. The device of claim 1, comprising another first member and second member.

29. A device for dispensing a substance having:

a dispensing outlet from which the substance is dispensable, a dispensing member mounted for movement in a dispensing direction from a first position to a second position, said movement, in use, causing the substance to be dispensed from the dispensing outlet, and an actuator mechanism for moving the dispensing member from the first position to the second position, said actuator mechanism having:

a first member mounted for movement in a predetermined direction, and a second member pivotally mounted on the first member for pivotal movement in a predetermined pivotal sense, wherein the actuator mechanism is adapted such that:

movement of the first member in the predetermined direction results in the second member moving therewith and pivoting in the predetermined pivotal sense, and said pivotal movement of the second member in the predetermined pivotal sense results in the dispensing member moving from the first position to the second position, and wherein the actuator mechanism comprises a biasing force for biasing the second member to pivot in an opposite sense to the predetermined pivotal sense; and comprising a spring element to provide the biasing force.

30. The device of claim 29, wherein the first member is a finger-operable actuator member.

31. The device of claim 30, wherein the finger-operable actuator member is the sole actuator member.

32. The device of claim 29, wherein the first member is mounted for pivotal movement in the predetermined direction.

33. The device of claim 32, wherein the first member is pivotally movable in the predetermined direction in a sense which is opposite to the predetermined pivotal sense.

34. The device of claim 29, wherein the second member has at least one surface which when pivoting in the predetermined pivotal sense comes into contact with at least one surface of the dispensing member to cause the dispensing member to move from the first position to the second position.

35. The device of claim 29, wherein the actuator mechanism is adapted in use to provide for relative movement between the first member and the second member, on the one hand, and a pusher surface, on the other hand, said relative movement bringing the pusher surface into pushing engagement with the second member for pivoting the second member in the predetermined pivotal sense.

36. The device of claim 35, wherein the pusher surface is presented by a housing of the device.

37. The device of claim 35, wherein the pusher surface is a static surface of the device.

38. The device of claim 29, wherein the actuator mechanism has a pusher surface adapted to engage the second member as the first member moves in the predetermined direction and to cause the second member to pivot in the predetermined pivotal sense.

39. The device of claim 29, wherein the second member has a pair of arms extending therefrom.

40. The device of claim 39,
wherein the actuator mechanism is adapted in use to provide for relative movement between the first member and the second member, on the one hand, and a pusher surface, on the other hand, said relative movement bringing the pusher surface into pushing engagement with the second member for pivoting the second member in the predetermined pivotal sense, and
wherein one of the arms of the second member is adapted in use to engage with the pusher surface to pivot the second member in the predetermined pivotal sense.

41. The device of claim 39, wherein the arms are different lengths.

42. The device of claim 39, wherein the second member has plural such pairs of arms.

43. The device of claim 29, further comprising a surface of, or associable with, the dispensing member of the device which is adapted for engagement by the second member, as the first member moves in the predetermined direction, so as to move the dispensing member from the first position to the second position.

44. The device of claim 43, wherein the surface is provided by a component part for the dispensing member.

45. The device of claim 44, wherein the component part is an accessory for the dispensing member.

46. The device of claim 29, wherein the first member is a lever.

47. The device of claim 29, wherein the spring element is comprised in the second member.

48. The device of claim 47, wherein the spring element is an integrally formed part of the second member.

49. The device of claim 47, wherein the spring element is disposed on a mounting section of the second member which is pivotally mounted to the first member.

50. The device of claim 29 comprising another first member and second member.

51. The device of claim 29, wherein the second member is a bell crank.

52. The device of claim 29, wherein the dispensing direction is along an axis and the predetermined direction is generally transverse to the axis.

53. The device of claim 29, wherein the dispensing member is a dispensing container for containing a supply of the substance.

54. The device of claim 29, wherein the dispensing outlet is co-axially arranged with the dispensing direction.

55. The device of claim 29, wherein the dispensing member has a dispensing mechanism which is adapted to deliver a dose of the substance from the dispensing outlet in response to the dispensing member being moved from the first position to the second position by the actuator mechanism.

56. The device of claim 29, wherein the dispensing outlet is in a nozzle sized and shaped for insertion into a nostril of a human or animal body.

57. The device of claim 29, wherein the dispensing outlet is part of a housing, the housing adapted to receive therein the dispensing member.

* * * * *